(12) United States Patent
Kasibhatla et al.

(10) Patent No.: US 7,241,890 B2
(45) Date of Patent: Jul. 10, 2007

(54) PURINE ANALOGS HAVING HSP90-INHIBITING ACTIVITY

(75) Inventors: Srinivas Rao Kasibhatla, San Diego, CA (US); Kevin Hong, San Diego, CA (US); Lin Zhang, San Diego, CA (US); Marco Antonio Biamonte, San Diego, CA (US); Marcus F. Boehm, San Diego, CA (US); Jiandong Shi, San Diego, CA (US); Junhua Fan, San Diego, CA (US)

(73) Assignee: Conforma Therapeutics Corporation, San Diego, CA (US)

( * ) Notice: Subject to any disclaimer, the term of this patent is extended or adjusted under 35 U.S.C. 154(b) by 0 days.

(21) Appl. No.: 10/494,414

(22) PCT Filed: Oct. 30, 2002

(86) PCT No.: PCT/US02/35069

§ 371 (c)(1), (2), (4) Date: Oct. 4, 2004

(87) PCT Pub. No.: WO03/037860

PCT Pub. Date: May 8, 2003

(65) Prior Publication Data

US 2005/0049263 A1    Mar. 3, 2005

Related U.S. Application Data

(60) Provisional application No. 60/335,391, filed on Oct. 30, 2001.

(51) Int. Cl.
- *C07D 473/40* (2006.01)
- *C07D 473/24* (2006.01)
- *C07D 473/34* (2006.01)
- *A61K 31/52* (2006.01)
- *A61P 35/00* (2006.01)

(52) U.S. Cl. ............... 544/276; 544/265; 544/277
(58) Field of Classification Search .......... 544/265, 544/266, 276; 514/263.3, 263.37, 263.33, 514/263.32, 263.31, 263.23, 263.2, 263.21, 514/263.38

See application file for complete search history.

(56) References Cited

U.S. PATENT DOCUMENTS

| | | | |
|---|---|---|---|
| 4,495,190 A | 1/1985 | Hagberg et al. | |
| 4,547,573 A | 10/1985 | Jung et al. | |
| 4,617,304 A | 10/1986 | Ashton et al. | |
| 4,699,877 A | 10/1987 | Cline et al. | |
| 4,748,177 A | 5/1988 | Sircar et al. | |
| 4,772,606 A | 9/1988 | Sircar et al. | |
| 4,774,325 A | 9/1988 | Casadio et al. | |
| 4,806,642 A | 2/1989 | Sircar et al. | |
| 4,918,162 A | 4/1990 | Slamon et al. | |
| 4,921,859 A | 5/1990 | Sircar et al. | |
| 4,923,885 A | 5/1990 | Hupe et al. | |
| 4,968,603 A | 11/1990 | Slamon et al. | |
| 5,002,950 A | 3/1991 | Malone et al. | |
| 5,098,906 A | 3/1992 | Sircar et al. | |
| 5,110,818 A | 5/1992 | Allgeier | |
| 5,204,353 A | 4/1993 | Meier | |
| 5,217,866 A | 6/1993 | Summerton et al. | |
| 5,332,744 A * | 7/1994 | Chakravarty et al. | 514/263.2 |
| 5,602,156 A | 2/1997 | Kohn et al. | |
| 5,656,629 A | 8/1997 | Bacon et al. | |
| 5,789,394 A | 8/1998 | Nguyen-Ba et al. | |
| 5,846,749 A | 12/1998 | Slamon et al. | |
| 5,861,503 A | 1/1999 | Barrio et al. | |
| 5,917,042 A | 6/1999 | Daluge et al. | |
| 5,955,610 A | 9/1999 | Nguyen-Ba et al. | |
| 5,994,361 A * | 11/1999 | Penney et al. | 514/263.4 |
| 6,005,107 A | 12/1999 | Nguyen-Ba et al. | |
| 6,143,743 A * | 11/2000 | Wilde et al. | 514/234.2 |

(Continued)

FOREIGN PATENT DOCUMENTS

EP    55239 B1    6/1982

(Continued)

OTHER PUBLICATIONS

Janeba, Zlatko, Collection of Czechoslovak Chemical Communications 66(9), 1393-1406 (Sep. 2001).*

(Continued)

*Primary Examiner*—Mark L. Berch
(74) *Attorney, Agent, or Firm*—Wilson Sonsini Goodrich & Rosati

(57) ABSTRACT

Novel purine compounds of Formula I.

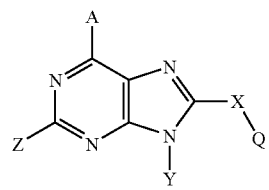

and tautomers, pharmaceutically acceptable salts, and prodrugs thereof, wherein X is S, S(O), or S(O)$_2$; and Q is selected from alkyl, cycloalkyl, arylalkyl, aryl, heteroaryl, and heterocyclic, all optionally substituted, are described, as are pharmaceutical compositions comprising the same, complexes comprising the same, e.g., HSP90 complexes, and methods of using the same.

5 Claims, 2 Drawing Sheets

U.S. PATENT DOCUMENTS

| | | | |
|---|---|---|---|
| 6,174,875 B1 | 1/2001 | DeFranco et al. | |
| 6,210,974 B1 | 4/2001 | Gold | |
| 6,262,254 B1 | 7/2001 | Barrio et al. | |
| 6,333,331 B1* | 12/2001 | Moschel et al. | 514/263.3 |
| 6,369,092 B1 | 4/2002 | Pamukcu et al. | |
| 6,723,727 B1* | 4/2004 | Peyman et al. | 514/263.21 |
| 2002/0156277 A1 | 10/2002 | Fick et al. | |
| 2002/0161014 A1 | 10/2002 | Sadhu et al. | |
| 2003/0022864 A1 | 1/2003 | Ishaq et al. | |
| 2003/0078413 A1 | 4/2003 | Dempcy et al. | |
| 2005/0107343 A1 | 5/2005 | Kasibhatla et al. | |
| 2005/0113339 A1 | 5/2005 | Kasibhatla et al. | |
| 2005/0113340 A1 | 5/2005 | Kasibhatla et al. | |
| 2005/0119282 A1 | 6/2005 | Kasibhatla et al. | |

FOREIGN PATENT DOCUMENTS

| | | |
|---|---|---|
| EP | 156559 B1 | 10/1985 |
| EP | 159264 B1 | 10/1985 |
| EP | 178178 A2 | 4/1986 |
| EP | 206415 B1 | 12/1986 |
| EP | 0184322 B1 | 12/1989 |
| EP | 363320 A2 | 4/1990 |
| EP | 151528 B1 | 7/1990 |
| EP | 465297 B1 | 1/1992 |
| EP | 502690 B1 | 9/1992 |
| EP | 565377 B1 | 10/1993 |
| EP | 675123 A1 | 10/1995 |
| JP | 06080670 A2 | 3/1994 |
| JP | 08041035 A2 | 2/1996 |
| JP | 08208687 A2 | 8/1996 |
| JP | 09020776 A2 | 1/1997 |
| JP | 09169758 2 | 6/1997 |
| JP | 10025294 A2 | 1/1998 |
| JP | 2000-072773 A2 | 3/2000 |
| WO | WO-86/05518 A1 | 9/1986 |
| WO | WO-89/10923 A1 | 11/1989 |
| WO | WO-92/05180 A1 | 4/1992 |
| WO | WO-95/07695 A1 | 3/1995 |
| WO | WO-95/08327 A1 | 3/1995 |
| WO | WO-98/01448 A1 | 1/1998 |
| WO | WO-98/39344 A1 | 9/1998 |
| WO | WO-98/51702 A1 | 11/1998 |
| WO | WO-99/01454 A1 | 1/1999 |
| WO | WO-99/02162 A1 | 1/1999 |
| WO | WO-99/12927 A1 | 3/1999 |
| WO | WO-99/24432 A1 | 5/1999 |
| WO | WO-99/32122 A1 | 7/1999 |
| WO | WO-99/51223 A1 | 10/1999 |
| WO | WO-00/43394 A1 | 7/2000 |
| WO | WO-00/44750 A1 | 8/2000 |
| WO | WO-00/53394 A1 | 9/2000 |
| WO | WO-00/68230 A1 | 11/2000 |
| WO | WO-01/38584 A2 | 5/2001 |
| WO | WO 02/36075 A | 5/2002 |
| WO | WO-02/055521 A1 | 7/2002 |
| WO | WO-02/057288 A1 | 7/2002 |
| WO | WO-02/069900 A2 | 9/2002 |
| WO | WO-02/085905 A1 | 10/2002 |
| WO | WO-02/088079 A2 | 11/2002 |
| WO | WO-02/088080 A2 | 11/2002 |
| WO | WO-02/094196 A2 | 11/2002 |
| WO | WO-02/102314 A2 | 12/2002 |
| WO | WO-03/000200 A2 | 1/2003 |
| WO | WO-03/002565 A1 | 1/2003 |
| WO | WO-03/026571 A2 | 4/2003 |
| WO | WO-03/037860 A2 | 5/2003 |

OTHER PUBLICATIONS

Panouse, Annales Pharma. Francaises 2000 58(5) 291-302.*

Baker et al. "Irreversible Enzyme Inhibitors. XCV. 8-(m-Bromoacetamidobenzylthio) hypoxanthine, and Active-Site-Directed Irreversible Inhibitor of Xanthine Oxidase" J. Medicinal Chemistry 10(4), 682 (1967). See compounds 6, 8a, 12, 14, 15, 17.

Kos et al. "Deamination of 6-Amino-and 6-(Alkylamino)-9-alkylpurines and Demethylation of Methylthiopurines by Sodium in Liquid Ammonia", J. Org. Chem. 1981, 46, 5000-5003. See Table 1, last 2 compounds.

Noelle et al. "Potential Purine Antagonists. XX. The Preparation and Reactions of Some Methylthiopurines" J. American Chemical Society 81, 5997-6007 (1959). See species of Tables II-IV, Scheme IV.

Van Calenbergh et al. Synthesis and Structure-Activity Relationships of Analogs of 2'-Deoxy-2'-(3-methoxybenzamido)adenosine, a Selective Inhibitor of Trypanosomal Glycosomal Glyceraldehyde-3-phosphate Dehydrogenase J. Med. Chem. 1995, 38, 3838-3849, 1995. See 35a-35b.

U.S. Appl. No. 60/128,593, filed Apr. 9, 1999, Neal Rosen.

U.S. Appl. No. 60/293,246, filed May 23, 2001, Neal Rosen.

U.S. Appl. No. 60/335,391, filed Oct. 30, 2001, Srinivas Kasibhatla.

U.S. Appl. No. 60/371,668, Ulm et al.

Abblard, J. et al., "Preparation et determination de structure de nouvelles pyridines halogenees Mecanisme de l'halagenation," Bull. Soc. Chim. Fr. 1972, 2466.

Abramovitch Pyridine and its derivatives, Supp. Part 2, Wiley & Sons, 1974, pp. 1-2.

Alhede, J., "A Simple and Efficient Synthesis of 9-Substituted Guanines. Cyclodesulfurization of 1-Substituted-5;[(Thiocarbamoyl)amino]imidazole-4-carboxamides under Aqueous Basic Conditions," Org. Chem. 1991, 2139.

Andricopulo, A.D. and Yunes, R.A., "Structure-activity relationships for a collection of structurally diverse inhibitors of purine nucleoside phosphorylase," Chem. & Pharm. Bull. 49(1), 10-17 (2001).

Ashton, W.T. et al., "Synthesis and Antiherpetic Activity of (±)-9-[[(Z)-2-(Hydroxymethyl)cyclopropyl]methyl]guanine and Related Compounds," J. Med. Chem. 1988, 31, 2304-2315.

Ashwell, M. et al., "An improved route to guanines substituted at N-9," J. of the Chem. Soc., Chem. Comm. (14), 955-6 (1990).

Bakkestuen, A. K., et al., "9-Benzylpurines with inhibitory activity against Mycobacterium tuberculosis," Biorg. & Med. Chem. Ltrs., 10(11), 1207-1210 (2000).

Balo, M.C. et al, "Synthesis of novel carbocyclic nucleosides with a cyclopentenyl ring: homocarbovir and analogs," Tetrahedron 54(12), 2833-2842 (1998).

Balo, M.C. et al, "Synthesis and antiviral activies of some novel carbocyclic nucleosides," Nucleosides & Nucleotides 15(7&8), 1335-1346 (1996).

Bedard, J. et al., "Comparative study of the anti-human cytomegalovirus activities and toxicities of a tetrahydrofuran phosphonate analog of guanosine and cidofovir," Antimocrobial Agents & Chemo. 43(3), 557-567 (1999).

Bennett, L.L., et al., "Mode of action of 2-amino-6-chloro-1-deazapurine," Biochem. Pharmacol. 33(2), 261-71 (1984).

Bennett, S.M., "Synthesis and Antiviral Acitivity of Some Acyclic and C-Acyclic Pyrrolo[2,3-d]pyrimidine Nucleoside Analogues," J. Med. Chem. 1990, 33, 2162.

Berge et al., "Pharmaceutical Salts," J. Pharm. Sci. 1977, 66:1-19.

Blanco, J.M. et al., "Synthesis and antiviral and antineoplastic activities of some novel carbocyclic guanosine analogs with a cyclobutane ring," Chem. & Pharm. Bulletin, 47(9), 1314-1317, (1999).

Blanco, J.M. et al., "Synthesis and antiviral and cytostatic activities of carbocyclic nucleosides ncorporating a modified cyclopentane ring. 1. Guanosine analogs.," Nucleosides & Nucleotides 16(1&2), 159-171 (1997).

Blanz, E.J. et al., "Carcinostatic Activity of Thiosemicarbazones of Formyl Heteroaromatic Compounds. VII. 2-Formylpyridine Derivatives Bearing Additional Ring Sustituents," J. Med. Chem. 1970, 13, 1124-1130.

Buchner, J., "Hsp90 & Co.-a holding for folding," TIBS, Apr. 1999, 24:136-141.

Buchwald, H. et al., "Long-term, continuous intravenous heparin administration by an implantable infusion pump in ambulatory patients with recurrent venou thrombosis," Surgery, 1980, 88, 507.

Bundgaard, H., "Design of Prodrugs," Textbook of Drug Design and Development, Krosgaard-Larsen and H. Bundgaard, Ed., 1991, Ch. 5, pp. 113-191.

Bundgaard, H., Advanced Drug Delivery Review, 1992, 8, 1-38.

Burger, A. et al., "Synthesis of 8-(O-Hydroxyalkyl)-, 8-(o-Hydroxyalk-1-enyl)-, and 8-(o-Hydroxyalk-1-ynyl)adenines Using the tert-Butyldimethylsilyloxymethyl Group, a New and Versatile Protecting Group of Adenine," J. Org. Chem. 2000, 65, 7825-7832.

Caamano, O. et al, "Carbocyclic nucleosides with a modified cyclopentane skeleton," Nucleosides & Nucleotides 14(3-5), 295-7 (1995).

Caplan, A., "Hsp90's secrets unfold: new insights from structural and functional studies," Trends in Cell Biol. 1999, 9:262-268.

Cheng, C.C. et al., "Rearrangement of 4-Amino-6-chloro-1-methylpyrazolo (3,4-d)pyrimidine in Basic Solution," J. Org. Chem. 1959, vol. 24, pp. 1570-1571.

Chern, J.W. et al., "Certain 8-Amino-9-(benzul)guanines as potential purine nucleoside phosphorylase inhibitors," Eur. J. Med. Chem. 1994, 29(1), 3-9.

Chiosis et al., A Small Molecule Designed to Bind to the Adenine Nucleotide Picket of HSP90 Causes HER2 Degradation and the Growth Arrest and Differentiation of Breast Cancer Cells, Chem. & Biol. 8, 289-299 (2001).

Choi, B.G. et al, "Synthesis and antiviral activity of novel exomethylene cyclopropyl nucleosides," Nucleosides, Nucleotides & Nucleic Acids 20(4-7), 1059-1062 (2001).

Chowdhury, S.F. et al., "Design, Synthesis, and Evaluation of Inhibitors of Trypanosomal and Leishmanial Dihtdorofolate Reductase," J. Med. Chem. 1999, 42, 4300-4312.

Cory, A. et al., "Use of an aqueous soluble tetrazolium/formazan assay for cell growth assays in culture," Cancer Comm. 1991, 3, 207-212.

Dai et al., "Physical interaction of mammalian CDC37 with CDK4," J. Biol. Chem. 1996, 271:22030-22034.

De Cat, A., "Synthetic Applications of Difluorocarbene," Bull. Soc. Chim. Belg. 1965, 74, 270-280.

De La Torre-Bueno, J. et al., Modern Pathology 2000, 13, 221A #1301.

De Napoli, L., "Reaction of 3',4'-Di-O-acetyl-2'-deoxyinosine with the Chlorinating Agent PPh3-CCI4: Synthesis of the 6-chloroderivative and of a new base linked dimmer, useful intermediate to 15N-1-labelled 2'-deoxyinosine," J. Chem. Soc., Perkin Trans 1, 1994, pp. 923-925.

Deng, H.F., "Study on the synthesis of N6 aromatic heterocyclic methyl substituted adenosine and adenine by Dimroth rearrangement reaction," Chinese Chem. Ltrs. 5(4), 271-4 (1994).

Erion, M.D. et al., Structure-based design of inhibitors of purine nucleoside phophorylase.3. 9-arylmethyl derivatives of 9-deazaguanine substituted on the arylmethyl group. J. of Med. Chem. 37(7), 1034 (1994).

Erion M.D. et al., "Structure-Based Design of Inhibitors of Purine Nucleoside Phosphorylase. 3. 9-Arylmethyl Derivatives of 9-Deazaguanine Substituted on the Methylene Group," J. Med. Chem. 1993, 36, 3771-3783.

Erlichman, C. et al., "A Phase I Trial of 17-Allyl-Amino-Geldanamycin in Patients with Advanced Cancer," Proc. AACR (2001), 42, Abstract 4474.

Fisher, B.E. et al., "The Structure of Isomaltol," J. Org. Chem. 1964, 29, 776.

Gangjee et al., "Design, Synthesis and X-ray Crystal Structure of a Potent Dual Inhibitor of Thymidylate Synthase and Dihydrofolate Reductase as an Antitumor Agent," J. Am. Chem. Soc. 2000, vol. 43, No. 21, pp. 3837-3851.

Goodson, J., "Medical Applications of Controlled Release," 1984, vol. 2, pp. 115-138.

Grenert et al., "The amino-terminal domain of heat shock protein 90 (hsp90) that binds geldanamycin is an ATP/ADP switch domain that regulates hsp90 conformation," J. Biol. Chem. 1997, 272::23843-23850.

Halazy, S. et al., Fluorophosphonate derivatives of N9-benzylguanine as potent slow-binding multisubstrate analog inhibitors of purine nucleoside phosphorylase, Tetrahedron, 52(1), 177-84 (1996).

Halazy, S. et al., "Phosphonate derivatives of N9-benzylguanine: a new class of potent purine nucleoside phosphorylase inhibitors," Biorg. & Med. Chem. Ltrs. 2(5), 407-10 (1992).

Halbfinger, E. et al., "Molecular Recognition of Modified Nucleotides by the P2Y1-Receptor. 1. A Synthetic, Biochemical, and NMR Approach," J. Med. Chem. 1999, 42, 5325-5337.

Han, M.J. et al., "Polynucleotide analogs. VI. Synthesis and characterization of alternating copolymers of maleic anhydride and dihydropyran-containing guanine derivatives," J. of Polymer Science, Part A: Polymer Chemistry 33(11), 1829-39 (1995).

Hartmann et al., "Effects of the tyrosine-kinase inhibitor gelanamycin on ligand-induced her-2/heu activation, receptor expression and proliferation of her-2-positive malignant cell lines," Int. J. Cancer, 1997, 70:221-229.

Herdewijn, P. et al., "Synthesis and Structure-Activity Relationships o Analogs of 2'-Deoxy-2'-(3-mehoxybenzamido)adenosine, a Selective Inhibitor of Trypanosomal Glycosomal lyceraldehyde-3-phosphate Dehydrogenase," J. Med. Chem. 1995, 38, 3838-3849.

Holy, A. et al., "Structure-Antiviral Activity Relationship in the Series of Pyrimidine and Purine N-[2-(2-Phosphonomethoxy)ethyl] Nucleotide Analogues. 1. Derivatives Substituted at the Carbon Atoms of the Base," J. Med. Chem. 1999, 42, 2064-2086.

Holy, A. et al., "Acyclic nucleotide analogs. VI. Synthesis of (3-hydroxy-2-phosphonylmethoxypropyl) derivatives of heterocyclic bases," Collection of Czechoslovak Chemical Communications 54(9), 2470-501 (1989).

Hossain, N. et al., "Synthesis of homo-N-nucleosides, a series of C1' branched-chain nucleosides," Tetrahedron 52(15), 5563-78 (1996).

Hotoda, H. et al., "Biologically active oligodeoxyribonucleotides. X. Anti-HIV-1 activity and stability of modified hexanucleotides containing glycerl-skeleton," Nucleosides & Nucleotides 17(1-3), 243-252 (1998).

Houlton, A. et al, "Synthesis, structure and redox properties of ferrocenylmethylnucleobases," J. of the Chem Society, Dalton Transactions: Inorganic Chem. 1999, 18, 3229-3234.

Jacobson, K. A. et al., "Structure-Activity Relationships of Bisphosphate Nucleotide Derivatives as P2Y, Receptor Antanonists and Partial Agonists," J. Med. Chem. 1999, 42, 1625-1638.

Jeromin, G.E. et al., "Seitenkettenchlorierungen von N-Heterocyclen mit Trichlorisocyanursaure (TCC)," Chem. Ber. 1987, 120, 649-651.

Kanth et al., "Selective Reduction of Carboxylic Acids into Alcohols Using NaBH4 and 12", J. Org. Chem. 1991, 56, 5964-5965.

Kelley, J.L. et al., "6-(Alkylamino)-9-alkylpurines. A New Class of Potential Antipsychotic Agents," J. Med. Chem. 1997, 40, 3207-3216.

Kelley, J.L. et al., "9-[Phosphonoalkyl)benzyl]guanines. Multisubstrate Analogue Inhibitors of Human Erythrocyte Purine Nucleoside Phosphorylase," J. Med. Chem. 1993, 36, 3455-3463.

Kelley, J.L. et al., "Synthesis and Structure-Activity Relationships of 2-Substitued-6-(dimethylamino)-9-(4-methylbenzyl)-9H-purines with Antirhinovirus Activity," J. Med. Chem. 1989. 32, 218-224.

Kim, K. and McComas, W., "Chemoselective high-throughput purification mediated by solid-supported reagents: Its application to the first 6,9-disubstituted purine library synthesis," Cominatorial Chem. & High Throughput Screening, 3(2), 125-129 (2000).

Kim, D.K., et al., "Synthesis and evaluation of 2-amino-6-fluoro-9-(2-hydroxyethoxymethyl)purine esters as potential prodrugs of acyclovir," Bioorg. Med. Chem. 6(12), 2525-30 (1998).

Kjellberg, J. and Johansson, N.G., "Studies on the Alkylation of Derivatives of Guanine," Nucelosides & Nucleotides, 8(2), 225-256 (1989).

Kjellberg, J. and Johansson, N.G., "Characterization of N-7 and N-9 alkylated purines analogs by proton and carbon-13 NMR," Tetrahydron 42(23), 6541-44 (1985).

Kotra, L.P. et al., "Structure-Activity Relationships of 2'-2'-difluoro-1-erythro-pentofuranosyl Nucleosides," J. Med. Chem. 40, 3635-3644 (1997).

Kozai, S. and Maruyama, T., "Synthesis and biological activity of 9-(2,6-difluorobenzyl)-9H-purines bearing chlorine," Chem. & Pharm. Bulletin, 47(4), 574-575 (1999).

Kurokawa,H. et al., "Inhibition of HER2/neu(erbB-2) and Mitogen-activated Protein Kinases Enhances Tamoxifen Action against HER2-overexpressing, Tamoxifen-resistant Breast Cancer Cells," Cancer Res. 2000, 60, 5887-5894.

Kusmierek, J.T. et al., "Preparative electrochemical reduction of 2-amino-6-chloropurine and synthesis of 6-deoxyacyclovir, a fluorescent substrate of xanthine oxidase and a prodrug of acyclovir," Acta Chem Scan B 41(10), 701-7 (1987).

Kwak, E.Y. et al, "Synthesis and antiviral activity of novel methylene cyclopropyl nucleosides," Archives of Pharm. Res. 23(6), 559-563 (2000).

Langer, R., "New Methods of Drug Delivery," Science 1990, 249:1527-1533.

Langli, G. et al., "Regiochemistry in Stille couplings in 2,6-dihalopurines," Tetrahedron, 52(15), 5625-38 (1996).

Lee, Y.R. et al., "Design and synthesis of novel fluorocyclopropanoid nucleosides," Nucleosides, Nucleotides & Nucleic Acids 20(4-7), 677-679 (2001).

Legraverend, M. et al., "Synthesis and in vitro evaluation of novel 2,6,9-trisubstituted purines acting as cyclin-dependent kinase inhibitors," Biorg. & Med. Chem. 7(7), 1281-1293 (1999).

Lin, X. and Robins, M., "Mild and Efficient Functionalization at C6 of Purine 2'-Deoxynucleosides and Ribonucleosides," Org. Letters 2000, 2, 3497-3499.

Linn, J.A. et al., "1,4-Diazabicyclo[2.2.2.]octane (DABCO)-catalyzed hydrolysis and alcoholysis reactions of 2-amino-9-benzyl-6-chloro-9H-purine," J. of the Chem. Soc., Chem. Comm. (8), 913-914 (1994).

Liu, F. et al., "Addition and cycloaddition to 2-and 8-vinylpurines," Acta CXhemica Scandinavica, 53(4), 269-279 (1999).

Looker, J.H. et al., "Bromomaltol: Structure and Conversion to Novel Pyridone and Pyridine Derivatives," J. Org. Chem. 1979, 44, 3408-3410.

Mallory et al., "Pyrimido[4,5-c]pyridazines. 3. Preferential formation of 8-amino-1H-pyrimido[4,5-c]-1,2-diazepin-6(7H)-ones by cyclizations with .alpha., .gamma..-dioxoesters," J. Org. Chem. 1982, vol. 47, pp. 667-674.

Meegalla, S. et al., "Synthesis of 1-quinolyl derivatives of adenine and guanine," Synlett (1), 61-2 (1993).

Miller et al., "Depletion of the erbB-2-gene product p185 by benzoquinoid anasymcins," Cancer Res. 1994, 54:2724-2730.

Mimnaugh et al., "Polyubiquitination and proteaseomal degradation of the p185c-erbB-2 receptor protein-tyrosine kinase induced by geldanamycin," J. Biol. Chem. 1996, 271:22796-22801.

Mitchell, M.S. and Press, M. F., "The Role of Immunohistochemistry and Fluorescence in Situ Hybridization for HER-2/neu in Assessing the Prognosis of Breast Cancer," Oncol. Supp. 1999, 12, 108-116.

Montgomery, J.A. et al., "Synthesis of potential anticancer agents. XXX. (1-Aziridinyl)purines," J. of Med. & Pharm. Chem. 5, 15-24 (1962).

Morisawa, Y. et al., "Studies on Anticoccidial Agents. 1. Synthesis and Antiococcidial Activity of 4-Deoxypyridoxol and Its Esters," J. Med. Chem. 1974, 17, 1083-1086.

Muise-Heimericks et al., "Cyclin D expression is controlled post-transcriptionally via a phosphatidylinositol 3-kinase/Akt-dependent pathway," J. Biol. Chem. 1998, 273(45):29864-29872.

Nguyen-Ba, P. et al., "Design and SAR study of a novel class of nucleoside analogues as potent anti-HCMV agents," Nucleosides & Nucleotides 18(4&5), 821-827 (1999).

Nguyen-Ba, P. et al., "Identification of novel nucleotide phosphonate analogs with potent anti-HCMV activity," Bioorg. & Med. Chem. Ltrs. 8(24), 3561-3566 (1998).

Nguyen-Ba, P. et al., "Design and synthesis of a novel class of nucleotide analogs with anti-HCMV activity," Bioorg. & Med. Chem. Ltrs. 8(24), 3555-3560 (1998).

Onishi, T. and Tsuji, T., "Synthesis of cyclobutane analogs of the antiviral cyclopropane nucleoside A-5021," Nucleosides, Nucleotides & Nucleic Acids 20(12), 1941-1948 (2001).

Onishi, T. et al., "A practical synthesis of antiviral cyclopropane nucleoside A-5021," Tetrahedron Ltrs. 40(50), 8845-8847 (1999).

Ozeki, N. et al., "A New Sandmeyer Iodination of 2-Aminopurines in Non-Aqueous Conditions: Combination of Alkali Metal Iodide and Iodine as Iodine Sources," Heterocycles, vol. 55, No. 3, pp. 461-464, 2001.

Panaretou et al., "ATP binding and hydrolysis are essential to the function of the Hsp90 moleular chaperone in vivo," Embo J. 1998, 17 (16):4829-4836.

Parkanyi, C. et al., "Synthesis of Acyclic Nuceloside Analogs of 6-Substitutred 2-Aminopurines and 2-Amino-8-azapurines," J. Het. Chem. 1990, 27(5), 1409-1413.

Peterson, M.L. and Vince. R., "Synthesis and biological evaluation of carbocyclic analogues of lyxofuranosides of 2-amino-t-substituted-purines and 2-amino-6-substituted-8-azapurines," J. Med. Chem. 33(4), 1214-9 (1990).

Pierra, C. et al., "Synthesis and antiviral activities of enantiomeric 1-[2-(hydroxymethyl)cyclopropyl] methyl nucleosides," Nucleosides, Nucleotides & Nucleic Acids 19 (1&2), 253-268 (2000).

Press, M. et al., Modern Pathology 2000, 13 225A.

Prodromou, C. et al., "Identification and Structural Characterization of the ATP/ADP-Binding Site in the Hsp90 Molecular Chaperone," Cell 90:1997, 65-75.

Qiu, Y. and Zemlicka, J., "Synthesis of new nucleoside analogues comprising a geminal difluorocyclopropane moiety as potential antiviral/antitumor agents," Nucleosides & Nucleotides 18(10), 2285-2300 (1999).

Quintela et al., "Pyrazolopyrimidines: synthesis, effect on histamine release from rat peritoneal mast cells and cytotoxic activity," Eur. J. Med. Chem. 2001, vol. 36, pp. 321-332.

Robins, M.J. and Basom, G.L., "Nucleic Acid Related Compounds. 8. Direct Conversion f2'-Deoxyinosine to 6-Chloropurine 2'-Deoxyriboside and Selected 6-Substituted Deoxynucleosides and Their Evaluation as Substrates of Adenosine Deaminse," Can. J. Chem. 1973, 12, 3161-3169.

Santana, L. et al., "Synthesis of 1,2-disubstituted carbocyclic analogs of pyrimidine and purine nucleosides," Synthesis 10, 1532-1538 (2001).

Santana, L. et al., "Synthesis and biological activity of some 2-aminopurine carbonucleosides," Nucleosides & Nucleotides 16(7-9), 1337-1339 (1997).

Saudek, et al., "A Preliminary Trial of the Programmable Implantable Medication System for Insulin Delivery," N. Eng. J. Med. 1989, 321, 574-579.

Scheibel et al., "The charged region of Hsp90 modulates the function of the N-terminal domain," PNAS USA 1999, 96:1297-1302.

Schneider et al., "Pharmacologic shifting of a balance between protein refolding and degradation mediated by Hsp90," PNAS USA 1996, 93:14536-14541.

Schnur et al., "Inhibition of the oncogene product p185 in vitro in vivo by geldanamycin and dihydrogeldanamycin deriviates," J. Med. Chem. 1995, 38:3806-3812.

Schulte et al., "Disruption of the Raf-1-Hsp90 molecular complex results in destabilization of Raf-1 and loss of Raf-1-Ras assocation," J. Biol. Chem. 1995, 270:24585-24588.

Schulte et al., "Geldanamycin-induced destabiliztion of Raf-1 involves the proteasome," Biochem. Biophys. Res. Commun. 1997, 239:655-659.

Seela, F., "7-Desaza-Isostere von 2'-Desoxyxanthosin und 2'-Desoxyspongosin-Synthese via Glycoslierung von 2,3-Dichlor-7H-pyrrolo[2,3-d] pyrmidin," Liebigs. Ann. Chem, 1985, 312-320.

Sefton, M.V., "Implantable Pumps," 1987, CRC Crit. Ref. Biomed. Eng. 14:201.

Segnitz et al., "The function of steroid hormone receptors is inhibited by the hsp90-specific compound geldanamycin," J. Biol Chem. 1997, 272:18694-18701.

Sekiyama, T. et al., "Synthesis and Antiviral Activity of Novel Acyclic Nucleosides: Discovery of a Cyclopropyl Nucleoside with Potent Inhibitory Activity against Herpesviruses," J. Med. Chem. 1998, 41, 1284-1298.

Sen, A.K. et al., "Synthesis of compounds related to 4(5)-aminoimidazole-5(4)-carboxamides: part VI—synthesis of 3-(6-methoxyl-8-quinolyl)-7-methylpurin-6(3H)-one," Indian J. of Chem., Sect. B: Org. Chem. Including Medicinal Chem. 23B(9), 870-3 (1984).

Sepp-Lorenzo et al., "Herbimycin A indues the 20 S proteasome- and Ubiquitin-dependent degradation of receptor tyrosin kinases," J. Biol Chem. 1995, 270:1658-16587.

Shealy, Y.F. et al., "Synthesis and antiviral evaluation of carbocyclic analogues of 2-amino-6-substituted-purine 3'-deoxyribofuranosides," J. Med. Chem. 30(6), 1090-4 (1987).

Shealy, Y.F. et al., "Synthesis and antiviral evaluation of carbocyclic analogues of ribofuranosides of 2-amino-6-substituted-purines and of 2-amino-t-substituted-8-azapurines," J. Med. Chem., 27(5), 670-4 (1984).

Sircar, J.C., "8-amino-9-substituted guanines: potent purine nucleoside phosphorylase (PNP) inhibitors," Agents and Actions 21 (3-4), 253-6 (1987).

Smith et al., "Progesterone receptor structure and function altered by Geldanamycin, an hsp90-binding agent," Mol. Cell. Biol. 1995, 15:6804-6812.

Smith, E.M., "Pyridine-1-oxide in Pyridine and its Derivatives," from The Chemistry of Heterocyclic Compounds (Incomplete Cite).

Stebbins et al, "Crystal structure of an Hsp90-geldanamycin complex;targeting of a protein chaperone by an antitumor agent," Cell, 1997, 89:239-250.

Stepanova et al, "Mammalian p50cdc37 is a protein kinase-targeting subunit of HSP90 that binds and stabilizes Cdk4," Genes Dev. 1996, 10:1491-1502.

Terry, B.J. et al., "Broad-spectrum antiviral activity of the acyclic guanosine phosphonate (R,S)-HPMPG," Antiviral Res. 10(4-5), 235-51 (1988).

Tohidi, M. and Orgel, L.E., "Some acyclic analogs of nucleotides and their template-directed reactions," J. of Mol. Evolution 28(5), 367-373 (1989).

Toyota, A. et al., "Synthesis of nucleosides and related compounds. 31. The alkylation of 2-amino-6-chloropurines with alcohols by Mitsunobu reaction for a synthesis of carbocyclic guanosine analogs," Heterocycles 36(7), 1625-30 (1993).

Treat et al., "Liposomes in the Therapy of Infectious Disease and Cancer," Lopez-Bernstein and Fidler, Ed., Liss, NY, pp. 353-365, 1989.

Ugarkar, B.G., "Adenosine Kinase Inhibitors.. 1. Synthesis, Enzyme Inhibition and Antiseizure Activity of 5-Iodotubercidin Analogues," J. Med. Chem. 2000, 43, 2883-2893.

Ugarkar, B.G., "Adenosine Kinase Inhibitors. 2. Synthesis, Enzyme Inhibition and Antiseizure Activity of Diaryltubercidin Analogues," J. Med. Chem. 2000, 43, 2894-2905.

Vasilevskaya et al., "Effects of geldanamycin on signaling through activator-protein I inhypoxic HT29 human colon adenocarcinoma cells," Cancer Res. 1999, 59:3935-3940.

Veliz, E.A., C6 substitution of inosine using hexamethylphosphorous triamide in conjunction with carbon tetrahalide or N-halosuccinimide, Tetrahedron Lett. 2000, 41, 1695-1697.

Wang, R et al., "Methylene-*gem*-Difluorocyclopropane Analogues of Nucleosides: Synthesis, Cyclopropene-Methylenecyclopropane Rearrangment, and Biological Acitivity," J. Med. Chem. 2001, 44, 4019-4022.

Weidmann, K. et al., "24(2-Pyridylmethyl)sylfinyl]-1H-theino[3,4-d]imidazoles. A Novel Class of Gastric H+/K=-ATPase Inhibitors," J. Med. Chem. 1992, 35, 438-450.

Whitesell et al., "Inhibition of heat shock protein HSP90-pp60v-src heteroprotein complex formation by benzoquinone ansamycins: essential role for stress proteins in oncogenic transformation," PNAS USA 1994, 91:8324-8328.

Wong, C. et al., "Synthesis and Evaluation of HomoazaSugars as Glycosidase Inhibitors," J. Org. Chem. 1995, 60, 1492-1501.

Yokomatsu, T. et al., "Synthesis of 1,1-difluoro-5-(1H-9-purinyl)-2-pentenylphosphonic acids and the related methano analoges. Remarkable effect of the nucleobases and the cyclopropane rings on inhibitory activity toward purine nucleoside phosphorylase," Biorg. & Med. Chem. 6(12), 2495-2505 (1998).

Yokomatsu, T. et al., "Synthesis of (2'S,3'S)-9-(4-phosphono-4',4'-difluoro-2',3'-methanobutyl)guanine and its enantiomer. Evaluation of the inhibitory activity for purine nucleoside phosphorylase," Tetrahedron 53(33), 11297-11306(1997).

Zemlicka, J., "Synthesis and biological properties of 9-(2,4-dihydroxybutyl)adenine and guanine: new analogs of 9-(2,3-dihydroxypropyl)adenine (DHPA) and 9-(2-hydroxyethoxymethyl)guanine (acyclovir)," Nucleosides & Nucleotides 3(3), 245-64 (1984).

* cited by examiner

US 7,241,890 B2

PURINE ANALOGS HAVING HSP90-INHIBITING ACTIVITY

RELATED APPLICATIONS

This application claims priority to and incorporates by reference in its entirety Kasibhatla et al., U.S. Provisional Patent Application Ser. No. 60/335,391, entitled PURINE ANALOGS HAVING HSP90-INHIBITING ACTIVITY, filed Oct. 30, 2001.

FIELD OF THE INVENTION

The invention relates in general to purine analogs and their use in inhibiting heat shock protein 90's (HSP90's) to thereby treat or prevent HSP90-dependent diseases, e.g., proliferative disorders such as breast cancer.

BACKGROUND

The following description includes information that may be useful in understanding the present invention. It is not an admission that any of the information provided herein is prior art or relevant to the presently claimed inventions, or that any publication specifically or implicitly referenced is prior art.

HSP90s are ubiquitous chaperone proteins that are involved in folding, activation and assembly of a wide range of proteins, including key proteins involved in signal transduction, cell cycle control and transcriptional regulation. Researchers have reported that HSP90 chaperone proteins are associated with important signaling proteins, such as steroid hormone receptors and protein kinases, including, e.g., Raf-1, EGFR, v-Src family kinases, Cdk4, and ErbB-2 (Buchner J., 1999, TIBS, 24:136-141; Stepanova, L. et al., 1996, Genes Dev. 10:1491-502; Dai, K. et al., 1996, J. Biol. Chem. 271:22030-4). Studies further indicate that certain co-chaperones, e.g., Hsp70, p60/Hop/Sti1, Hip, Bag1, HSP40/Hdj2/Hsj1, immunophilins, p23, and p50, may assist HSP90 in its function (see, e.g., Caplan, A., Trends in Cell Biol., 9: 262-68 (1999).

Ansamycin antibiotics, e.g., herbimycin A (HA), geldanamycin (GM), and 17-AAG are thought to exert their anticancerous effects by tight binding of the N-terminus pocket of HSP90, thereby destabilizing substrates that normally interact with HSP90 (Stebbins, C. et al., 1997, Cell, 89:239-250). This pocket is highly conserved and has weak homology to the ATP-binding site of DNA gyrase (Stebbins, C. et al., supra; Grenert, J. P. et al., 1997, J. Biol. Chem., 272: 23843-50). Further, ATP and ADP have both been shown to bind this pocket with low affinity and to have weak ATPase activity (Proromou, C. et al., 1997, Cell, 90: 65-75; Panaretou, B. et al., 1998, EMBO J., 17: 4829-36). In vitro and in vivo studies have demonstrated that occupancy of this N-terminal pocket by ansamycins and other HSP90 inhibitors alters HSP90 function and inhibits protein folding. At high concentrations, ansamycins and other HSP90 inhibitors have been shown to prevent binding of protein substrates to HSP90 (Scheibel, T., H. et al., 1999, Proc. Natl. Acad. Sci. USA 96:1297-302; Schulte, T. W. et al., 1995, J. Biol. Chem. 270:24585-8; Whitesell, L., et al., 1994, Proc. Natl. Acad. Sci. USA 91:8324-8328). Ansamycins have also been demonstrated to inhibit the ATP-dependent release of chaperone-associated protein substrates (Schneider, C., L. et al., 1996, Proc. Natl. Acad. Sci. USA, 93:14536-41; Sepp-Lorenzino et al., 1995, J. Biol. Chem. 270:16580-16587). In either event, the substrates are degraded by a ubiquitin-dependent process in the proteasome (Schneider, C., L., supra; Sepp-Lorenzino, L., et al., 1995, J. Biol. Chem., 270:16580-16587; Whitesell, L. et al., 1994, Proc. Natl. Acad. Sci. USA, 91: 8324-8328).

HSP90 substrate destabilization occurs in tumor and non-transformed cells alike and has been shown to be especially effective on a subset of signaling regulators, e.g., Raf (Schulte, T. W. et al., 1997, Biochem. Biophys. Res. Commun. 239:655-9; Schulte, T. W., et al., 1995, J. Biol. Chem. 270:24585-8), nuclear steroid receptors (Segnitz, B., and U. Gehring. 1997, J. Biol. Chem. 272:18694-18701; Smith, D. F. et al., 1995, Mol. Cell. Biol. 15:6804-12), v-src (Whitesell, L., et al., 1994, Proc. Natl. Acad. Sci. USA 91:8324-8328) and certain transmembrane tyrosine kinases (Sepp-Lorenzino, L. et al., 1995, J. Biol. Chem. 270:16580-16587) such as EGF receptor (EGFR) and Her2/Neu (Hartmann, F., et al., 1997, Int. J. Cancer 70:221-9; Miller, P. et al., 1994, Cancer Res. 54:2724-2730; Mimnaugh, E. G., et al., 1996, J. Biol. Chem. 271:22796-801; Schnur, R. et al., 1995, J. Med. Chem. 38:3806-3812), CDK4, and mutant p53. Erlichman et al., Proc. AACR (2001), 42, abstract 4474. The ansamycin-induced loss of these proteins leads to the selective disruption of certain regulatory pathways and results in growth arrest at specific phases of the cell cycle (Muise-Heimericks, R. C. et al., 1998, J. Biol. Chem. 273:29864-72), and apoptosis, and/or differentiation of cells so treated (Vasilevskaya, A. et al., 1999, Cancer Res., 59:3935-40).

In addition to anti-cancer and antitumorgenic activity, HSP90 inhibitors have also been implicated in a wide variety of other utilities, including use as anti-inflammation agents, anti-infectious disease agents, agents for treating autoimmunity, agents for treating ischemia, and agents useful in promoting nerve regeneration (See, e.g., Rosen et al., WO 02/09696; PCT/US01/23640; Degranco et al., WO 99/51223; PCT/US99/07242; Gold, U.S. Pat. No. 6,210,974 B1). There are reports in the literature that fibrogenic disorders including but not limited to scleroderma, polymyositis, systemic lupus, rheumatoid arthritis, liver cirrhosis, keloid formation, interstitial nephritis, and pulmonary fibrosis may be treatable. (Strehlow, WO 02/02123; PCT/US01/20578).

Ansamycins and other HSP90 inhibitors thus hold great promise for the treatment and/or prevention of many types of disorders. However, their relative insolubility makes them difficult to formulate and administer, and they are not easily synthesized and currently must, at least in part, be generated through fermentation. Further, the dose limiting toxicity of ansamycins is hepatic. Despite the potential of ansamycins, alternative HSP90 inhibitors are therefore needed.

Recently, Chiosis et al. described the design and synthesis of purine analogs that mimic geldanamycin and other ansamycins in their ability to bind the ATP binding pocket of, and thus inhibit, HSP90. See International Patent Application PCT/US01/46303 (WO 02/36075; Chemistry & Biology 8:289-299 (2001). The specific compounds that Chiosis et al. described included a trimethoxybenzyl entity substituted at positions 3,4, and 5. Using gel-binding assays, these were shown to bind HSP90 approximately 20-fold less avidly than the benzoquinone ansamycin, 17-AAG. Chiosis et al. did not attempt a quinone mimic for the methoxybenzyl entity, speculating that to do so would lead to hepatoxicity. Id., pg. 290, col. 1, ¶ 4. Nor did Chiosis et al. teach, suggest, or otherwise report the use of sulfides, sulfoxides, and sulfones as described herein.

SUMMARY OF THE INVENTION

Applicants herein describe a set of purine-based compounds that have utility in inhibiting HSP90 and diseases that are HSP90-dependent, e.g., a variety of carcinomas, such as melanoma, breast cancer, etc.

In one embodiment, the purine or purine analog has structure I, II, III, or IV:

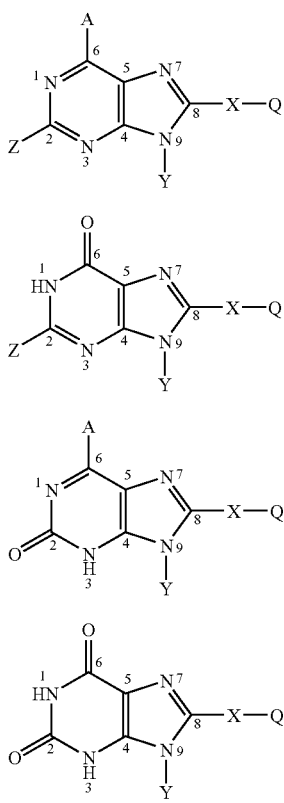

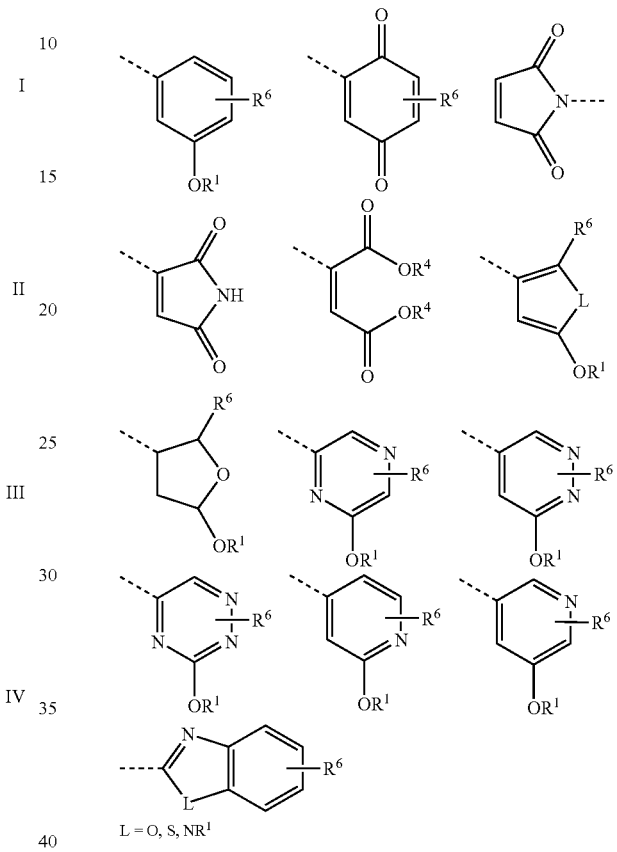

L = O, S, NR$^1$ wherein A is selected from NR$^1{}_2$, NR$^1$SO$_2$R$^2$, NR$^1$NR$^1{}_2$, NR$^1$OR$^4$, OR$^3$, SR$^3$, optionally substituted lower alkyl, optionally substituted cycloalkyl, C(O)N(R$^4$)$_2$, guanidiyl, amidinyl, H, halogen, CN, N$_3$ and perhaloalkyl;

wherein X is a 1 carbon, 2 carbon, or 3 carbon optionally substituted structure (C1-C3), or else NR$^1$, S, S(O), S(O)$_2$, O, or C(O). For carbon linkers having more than 1 carbon, these may have single, double, or triple bonds between them.

wherein Y is selected from the group consisting of H, optionally substituted alkyl, optionally substituted alkenyl, optionally substituted alkynyl, optionally substituted aryl, optionally substituted alicyclic, optionally substituted araalkyl, optionally substituted aryloxyalkyl, optionally substituted alkoxyalkyl, alkylaminoalkyl, alkylcarbonylaminoalkyl (—(CH$_2$)$_n$—C(O)—NR—(CH$_2$)$_n$), alkylcarbonyloxylalkyl (—(CH$_2$)$_n$—C(O)—O—(CH$_2$)$_n$), optionally substituted heterocyclic, hydroxyalkyl, haloalkyl, perhaloalkyl, C(O)R$^2$, S(O)$_2$R$^2$, C(O)NHR$^2$, and C(O)OR$^2$;

wherein Z is selected from the group consisting of H, halogen, CN, OR$^3$, SR$^3$, perhaloalkyl, optionally substituted alkyl, optionally substituted alkenyl, optionally substituted alkynyl, optionally substituted aryl, optionally substituted alicyclic, optionally substituted araalkyl, optionally substituted aryloxyalkyl, optionally substituted alkoxyalkyl, optionally substituted heterocyclic, C(O)R$^2$, —S(O)$_2$R$^2$, NHOR$^4$, and C(O)NR$^4{}_2$;

Q is selected from the group consisting of alkyl, cycloalkyl, arylalkyl, aryl, heteroaryl, and heterocyclic, all optionally substituted; e.g., R$^1$ is independently selected from H, optionally substituted alkyl, optionally substituted cycloalkyl, optionally substituted aryl, optionally substituted heterocyclic, C(O)R$^2$, —C(O)OR$^2$, C(O)NR$^4{}_2$, C(S)OR$^2$, C(S)NR$^4{}_2$, and SO$_2$R$^2$;

R$^2$ is independently selected from the group of C$_1$-C$_6$, C$_3$-C$_{10}$ cycloalkyl, heterocyclic, heteroaryl, and aryl, all optionally substituted;

R$^3$ is selected from H, optionally substituted alkyl, optionally substituted cycloalkyl, optionally substituted heteroalkyl, optionally substituted aryl, optionally substituted heterocyclic and C(O)NR$^4{}_2$; and wherein R$^4$ is selected from either H or from alkyl, cycloalkyl, heteroalkyl, aryl, and heterocyclic, all optionally substituted;

wherein R$^5$ is selected from H, OH, and optionally substituted alkyl; and wherein R$^6$ is independently selected from H, optionally substituted alkyl, OR$^3$, SR$^3$, NHR$_3$, C(O)R$^5$, NO$_2$, CN, halogen, and S(O)$_2$R$^2$. In some embodiments, the alkyl, alkenyl, and alkynyl substituent are 1 to 8 carbon atoms in length, more preferably 1 to 6 carbon atoms in length, and optionally substituted.

The subscript "n" can be 1 to 10 inclusive, with 3 or less being preferred.

Other compounds of the invention are based on the following formula, having illustrative species as described in Table 1:

TABLE 1

| No. | Ex. | W | X | Y | Z |
|---|---|---|---|---|---|
| 1 | 3.2 | 2,5-dimethoxy | CH₂ | pent-4-ynyl-(CH₂)₃CCH | H |
| 2 | | 2,3,5-trimethoxy | CH₂ | pent-4-ynyl | H |
| 3 | | 3,4,5-trimethoxy | CH₂ | pent-4-ynyl | H |
| 4 | 4.7 | 2-iodo, 5-methoxy | CH₂ | pent-4-ynyl | H |
| 5 | | 2-bromo, 5-methoxy | CH₂ | pent-4-ynyl | H |
| 6 | | 2-chloro, 5-methoxy | CH₂ | pent-4-ynyl | H |
| 7 | | 2,4-diiodo, 5-methoxy | CH₂ | pent-4-ynyl | H |
| 8 | | 2,5-diiodo | CH₂ | pent-4-ynyl | H |
| 9 | | 2,4-diiodo | CH₂ | pent-4-ynyl | H |
| 10 | | 2-iodo, 5-SCH₃ | CH₂ | pent-4-ynyl | H |
| 11 | | 2-iodo, 5-ethyl | CH₂ | pent-4-ynyl | H |
| 12 | | 2-iodo, 5-propyl | CH₂ | pent-4-ynyl | H |
| 13 | | 2-chloro, 5-SCH₃ | CH₂ | pent-4-ynyl | H |
| 14 | | 2-chloro, 5-ethyl | CH₂ | pent-4-ynyl | H |
| 15 | | 2-chloro, 5-propyl | CH₂ | pent-4-ynyl | H |
| 16 | | 2,5-SCH₃ | CH₂ | pent-4-ynyl | H |
| 17 | | 2-iodo, 4-fluoro, 5-methoxy | CH₂ | pent-4-ynyl | H |
| 18 | | 2-iodo, 3-fluoro, 5-methoxy | CH₂ | pent-4-ynyl | H |
| 19 | | 2-iodo, 6-fluoro, 5-methoxy | CH₂ | pent-4-ynyl | H |
| 20 | | 2-Chloro, 3-fluoro, 5-methoxy | CH₂ | pent-4-ynyl | H |
| 21 | | 2-Chloro, 4-fluoro, 5-methoxy | CH₂ | pent-4-ynyl | H |
| 22 | | 2-chloro-3,4,5-trimethoxy | CH₂ | pent-4-ynyl | H |
| 23 | | 2,3-diiodo, 5-methoxy | CH₂ | pent-4-ynyl | H |
| 24 | | 2,5-dichloro | CH₂ | pent-4-ynyl | H |
| 25 | | 2,5-dibromo | CH₂ | pent-4-ynyl | H |
| 26 | | 2-Iodo, 4-chloro, 5-methoxy | CH₂ | pent-4-ynyl | H |
| 27 | | 2-iodo, 4-bromo, 5-methoxy | CH₂ | pent-4-ynyl | H |
| 28 | | 2,5-dimethoxy | CH₂ | pent-4-ynyl | F |
| 29 | | 2,3,5-trimethoxy | CH₂ | pent-4-ynyl | F |
| 30 | | 3,4,5-trimethoxy | CH₂ | pent-4-ynyl | F |
| 31 | 4.10 | 2-iodo, 5-methoxy | CH₂ | pent-4-ynyl | F |
| 32 | | 2-bromo, 5-methoxy | CH₂ | pent-4-ynyl | F |
| 33 | | 2-chloro, 5-methoxy | CH₂ | pent-4-ynyl | F |
| 34 | | 2,4-diiodo, 5-methoxy | CH₂ | pent-4-ynyl | F |
| 35 | | 2,5-diiodo | CH₂ | pent-4-ynyl | F |
| 36 | | 2,4-diiodo | CH₂ | pent-4-ynyl | F |
| 37 | | 2-iodo, 5-SCH₃ | CH₂ | pent-4-ynyl | F |
| 38 | | 2-iodo, 5-ethyl | CH₂ | pent-4-ynyl | F |
| 39 | | 2-iodo, 5-propyl | CH₂ | pent-4-ynyl | F |
| 40 | | 2-chloro, 5-SCH₃ | CH₂ | pent-4-ynyl | F |
| 41 | | 2-chloro, 5-ethyl | CH₂ | pent-4-ynyl | F |
| 42 | | 2-chloro, 5-propyl | CH₂ | pent-4-ynyl | F |
| 43 | | 2,5-SCH₃ | CH₂ | pent-4-ynyl | F |
| 44 | | 2-iodo, 4-fluoro, 5-methoxy | CH₂ | pent-4-ynyl | F |
| 45 | | 2-iodo, 3-fluoro, 5-methoxy | CH₂ | pent-4-ynyl | F |
| 46 | | 2-iodo, 6-fluoro, 5-methoxy | CH₂ | pent-4-ynyl | F |
| 47 | | 2-Chloro, 3-fluoro, 5-methoxy | CH₂ | pent-4-ynyl | F |
| 48 | | 2-Chloro, 4-fluoro, 5-methoxy | CH₂ | pent-4-ynyl | F |

TABLE 1-continued

| No. | Ex. | W | X | Y | Z |
|---|---|---|---|---|---|
| 49 | | 2,3,4,5-tetraiodo | CH₂ | pent-4-ynyl | F |
| 50 | | 2,3-diiodo, 5-methoxy | CH₂ | pent-4-ynyl | F |
| 51 | | 2,5-dichloro | CH₂ | pent-4-ynyl | F |
| 52 | | 2,5-dibromo | CH₂ | pent-4-ynyl | F |
| 53 | | 2-Iodo, 4-chloro, 5-methoxy | CH₂ | pent-4-ynyl | F |
| 54 | | 2-iodo, 4-bromo, 5-methoxy | CH₂ | pent-4-ynyl | F |
| 55 | 3.4 | 2,5-dimethoxy | CH₂ | 4-methyl-pent-3-enyl-(CH₂)₂CHCMe₂ | H |
| 56 | | 2,3,5-trimethoxy | CH₂ | 4-methyl-pent-3-enyl | H |
| 57 | | 3,4,5-trimethoxy | CH₂ | 4-methyl-pent-3-enyl | H |
| 58 | 4.8 | 2-iodo, 5-methoxy | CH₂ | 4-methyl-pent-3-enyl | H |
| 59 | | 2-bromo, 5-methoxy | CH₂ | 4-methyl-pent-3-enyl | H |
| 60 | | 2-chloro, 5-methoxy | CH₂ | 4-methyl-pent-3-enyl | H |
| 61 | | 2,4-diiodo, 5-methoxy | CH₂ | 4-methyl-pent-3-enyl | H |
| 62 | | 2,5-diiodo | CH₂ | 4-methyl-pent-3-enyl | H |
| 63 | | 2,4-diiodo | CH₂ | 4-methyl-pent-3-enyl | H |
| 64 | | 2-iodo, 5-SCH₃ | CH₂ | 4-methyl-pent-3-enyl | H |
| 65 | | 2-iodo, 5-ethyl | CH₂ | 4-methyl-pent-3-enyl | H |
| 66 | | 2-iodo, 5-propyl | CH₂ | 4-methyl-pent-3-enyl | H |
| 67 | | 2-chloro, 5-SCH₃ | CH₂ | 4-methyl-pent-3-enyl | H |
| 68 | | 2-chloro, 5-ethyl | CH₂ | 4-methyl-pent-3-enyl | H |
| 69 | | 2-chloro, 5-propyl | CH₂ | 4-methyl-pent-3-enyl | H |
| 70 | | 2,5-SCH₃ | CH₂ | 4-methyl-pent-3-enyl | H |
| 71 | | 2-iodo, 4-fluoro, 5-methoxy | CH₂ | 4-methyl-pent-3-enyl | H |
| 72 | | 2-iodo, 3-fluoro, 5-methoxy | CH₂ | 4-methyl-pent-3-enyl | H |
| 73 | | 2-iodo, 6-fluoro, 5-methoxy | CH₂ | 4-methyl-pent-3-enyl | H |
| 74 | | 2-Chloro, 3-fluoro, 5-methoxy | CH₂ | 4-methyl-pent-3-enyl | H |
| 75 | | 2-Chloro, 4-fluoro, 5-methoxy | CH₂ | 4-methyl-pent-3-enyl | H |
| 76 | | 2-chloro-3,4,5-trimethoxy | CH₂ | 4-methyl-pent-3-enyl | H |
| 77 | | 2,3-diiodo, 5-methoxy | CH₂ | 4-methyl-pent-3-enyl | H |
| 78 | | 2,5-dichloro | CH₂ | 4-methyl-pent-3-enyl | H |
| 79 | | 2,5-dibromo | CH₂ | 4-methyl-pent-3-enyl | H |
| 80 | | 2-iodo, 4-chloro, 5-methoxy | CH₂ | 4-methyl-pent-3-enyl | H |
| 81 | | 2-iodo, 4-bromo, 5-methoxy | CH₂ | 4-methyl-pent-3-enyl | H |
| 82 | | 2,5-dimethoxy | CH₂ | 4-methyl-pent-3-enyl | F |

TABLE 1-continued

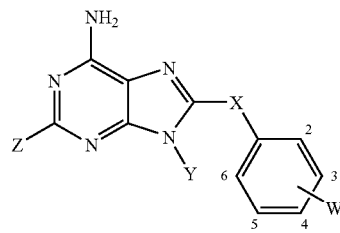

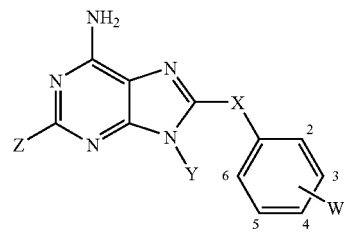

| No. | Ex. | W | X | Y | Z |
|---|---|---|---|---|---|
| 83 | | 2,3,5-trimethoxy | CH$_2$ | 4-methyl-pent-3-enyl | F |
| 84 | | 3,4,5-trimethoxy | CH$_2$ | 4-methyl-pent-3-enyl | F |
| 85 | 4.9 | 2-iodo, 5-methoxy | CH$_2$ | 4-methyl-pent-3-enyl | F |
| 86 | | 2-bromo, 5-methoxy | CH$_2$ | 4-methyl-pent-3-enyl | F |
| 87 | | 2-chloro, 5-methoxy | CH$_2$ | 4-methyl-pent-3-enyl | F |
| 88 | | 2,4-diiodo, 5-methoxy | CH$_2$ | 4-methyl-pent-3-enyl | F |
| 89 | | 2,5-diiodo | CH$_2$ | 4-methyl-pent-3-enyl | F |
| 90 | | 2,4-diiodo | CH$_2$ | 4-methyl-pent-3-enyl | F |
| 91 | | 2-iodo, 5-SCH$_3$ | CH$_2$ | 4-methyl-pent-3-enyl | F |
| 92 | | 2-iodo, 5-ethyl | CH$_2$ | 4-methyl-pent-3-enyl | F |
| 93 | | 2-iodo, 5-propyl | CH$_2$ | 4-methyl-pent-3-enyl | F |
| 94 | | 2-chloro, 5-SCH$_3$ | CH$_2$ | 4-methyl-pent-3-enyl | F |
| 95 | | 2-chloro, 5-ethyl | CH$_2$ | 4-methyl-pent-3-enyl | F |
| 96 | | 2-chloro, 5-propyl | CH$_2$ | 4-methyl-pent-3-enyl | F |
| 97 | | 2,5-SCH$_3$ | CH$_2$ | 4-methyl-pent-3-enyl | F |
| 98 | | 2-iodo, 4-fluoro, 5-methoxy | CH$_2$ | 4-methyl-pent-3-enyl | F |
| 99 | | 2-iodo, 3-fluoro, 5-methoxy | CH$_2$ | 4-methyl-pent-3-enyl | F |
| 100 | | 2-iodo, 6-fluoro, 5-methoxy | CH$_2$ | 4-methyl-pent-3-enyl | F |
| 101 | | 2-chloro, 3-fluoro, 5-methoxy | CH$_2$ | 4-methyl-pent-3-enyl | F |
| 102 | | 2-chloro, 4-fluoro, 5-methoxy | CH$_2$ | 4-methyl-pent-3-enyl | F |
| 103 | | 2-chloro-3,4,5-trimethoxy | CH$_2$ | 4-methyl-pent-3-enyl | F |
| 104 | | 2,3-diiodo, 5-methoxy | CH$_2$ | 4-methyl-pent-3-enyl | F |
| 105 | | 2,5-dichloro | CH$_2$ | 4-methyl-pent-3-enyl | F |
| 106 | | 2,5-dibromo | CH$_2$ | 4-methyl-pent-3-enyl | F |
| 107 | | 2-iodo, 4-chloro, 5-methoxy | CH$_2$ | 4-methyl-pent-3-enyl | F |
| 108 | | 2-iodo, 4-bromo, 5-methoxy | CH$_2$ | 4-methyl-pent-3-enyl | F |
| 109 | | 2,5-dimethoxy | S | pent-4-ynyl | H |
| 110 | | 2,3,5-trimethoxy | S | pent-4-ynyl | H |
| 112 | | 3,4,5-trimethoxy | S | pent-4-ynyl | H |
| 113 | 9.7 | 2-iodo, 5-methoxy | S | pent-4-ynyl | H |
| 114 | | 2-bromo, 5-methoxy | S | pent-4-ynyl | H |
| 115 | | 2-chloro, 5-methoxy | S | pent-4-ynyl | H |
| 116 | | 2,4-diiodo, 5-methoxy | S | pent-4-ynyl | H |
| 117 | | 2,5-diiodo | S | pent-4-ynyl | H |
| 118 | | 2,4-diiodo | S | pent-4-ynyl | H |
| 119 | | 2-iodo, 5-SCH$_3$ | S | pent-4-ynyl | H |
| 120 | | 2-iodo, 5-ethyl | S | pent-4-ynyl | H |
| 121 | | 2-iodo, 5-propyl | S | pent-4-ynyl | H |
| 122 | | 2-chloro, 5-SCH$_3$ | S | pent-4-ynyl | H |
| 123 | | 2-chloro, 5-ethyl | S | pent-4-ynyl | H |
| 124 | | 2-chloro, 5-propyl | S | pent-4-ynyl | H |
| 125 | | 2,5-SCH$_3$ | S | pent-4-ynyl | H |
| 126 | | 2-iodo, 4-fluoro, 5-methoxy | S | pent-4-ynyl | H |
| 127 | | 2-iodo, 3-fluoro, 5-methoxy | S | pent-4-ynyl | H |
| 128 | | 2-iodo, 6-fluoro, 5-methoxy | S | pent-4-ynyl | H |
| 129 | | 2-chloro, 3-fluoro, 5-methoxy | S | pent-4-ynyl | H |
| 130 | | 2-chloro, 4-fluoro, 5-methoxy | S | pent-4-ynyl | H |
| 131 | | 2-chloro-3,4,5-trimethoxy | S | pent-4-ynyl | H |
| 132 | | 2,3-diiodo, 5-methoxy | S | pent-4-ynyl | H |
| 133 | | 2,5-dichloro | S | pent-4-ynyl | H |
| 134 | | 2,5-dibromo | S | pent-4-ynyl | H |
| 135 | | 2-iodo, 4-chloro, 5-methoxy | S | pent-4-ynyl | H |
| 136 | | 2-iodo, 4-bromo, 5-methoxy | S | pent-4-ynyl | H |
| 137 | | 2,5-dimethoxy | S | pent-4-ynyl | F |
| 138 | | 2,3,5-trimethoxy | S | pent-4-ynyl | F |
| 139 | | 3,4,5-trimethoxy | S | pent-4-ynyl | F |
| 140 | | 2-iodo, 5-methoxy | S | pent-4-ynyl | F |
| 141 | | 2-bromo, 5-methoxy | S | pent-4-ynyl | F |
| 142 | | 2-chloro, 5-methoxy | S | pent-4-ynyl | F |
| 143 | | 2,4-diiodo, 5-methoxy | S | pent-4-ynyl | F |
| 144 | | 2,5-diiodo | S | pent-4-ynyl | F |
| 145 | | 2,4-diiodo | S | pent-4-ynyl | F |
| 146 | | 2-iodo, 5-SCH$_3$ | S | pent-4-ynyl | F |
| 147 | | 2-iodo, 5-ethyl | S | pent-4-ynyl | F |
| 148 | | 2-iodo, 5-propyl | S | pent-4-ynyl | F |
| 149 | | 2-chloro, 5-SCH$_3$ | S | pent-4-ynyl | F |
| 150 | | 2-chloro, 5-ethyl | S | pent-4-ynyl | F |
| 151 | | 2-chloro, 5-propyl | S | pent-4-ynyl | F |
| 152 | | 2,5-SCH$_3$ | S | pent-4-ynyl | F |
| 153 | | 2-iodo, 4-fluoro, 5-methoxy | S | pent-4-ynyl | F |
| 154 | | 2-iodo, 3-fluoro, 5-methoxy | S | pent-4-ynyl | F |
| 155 | | 2-iodo, 6-fluoro, 5-methoxy | S | pent-4-ynyl | F |
| 156 | | 2-chloro, 3-fluoro, 5-methoxy | S | pent-4-ynyl | F |
| 157 | | 2-chloro, 4-fluoro, 5-methoxy | S | pent-4-ynyl | F |
| 158 | | 2,3,4,5-tetraiodo | S | pent-4-ynyl | F |
| 159 | | 2,3-diiodo, 5-methoxy | S | pent-4-ynyl | F |
| 160 | | 2,5-dichloro | S | pent-4-ynyl | F |
| 161 | | 2,5-dibromo | S | pent-4-ynyl | F |
| 162 | | 2-iodo, 4-chloro, 5-methoxy | S | pent-4-ynyl | F |
| 163 | | 2-iodo, 4-bromo, 5-methoxy | S | pent-4-ynyl | F |
| 164 | | 2,5-dimethoxy | S | 4-methyl-pent-3-enyl | H |
| 165 | | 2,3,5-trimethoxy | S | 4-methyl-pent-3-enyl | H |
| 166 | | 3,4,5-trimethoxy | S | 4-methyl-pent-3-enyl | H |
| 167 | 9.6 | 2-iodo, 5-methoxy | S | 4-methyl-pent-3-enyl | H |

TABLE 1-continued

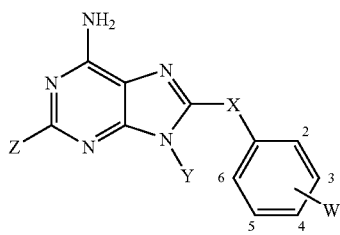

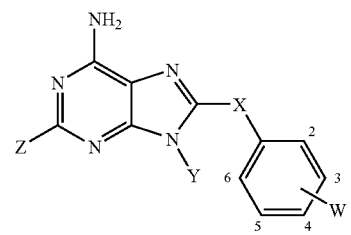

| No. | Ex. | W | X | Y | Z |
|---|---|---|---|---|---|
| 168 | | 2-bromo, 5-methoxy | S | 4-methyl-pent-3-enyl | H |
| 169 | | 2-chloro, 5-methoxy | S | 4-methyl-pent-3-enyl | H |
| 170 | | 2,4-diiodo, 5-methoxy | S | 4-methyl-pent-3-enyl | H |
| 171 | | 2,5-diiodo | S | 4-methyl-pent-3-enyl | H |
| 172 | | 2,4-diiodo | S | 4-methyl-pent-3-enyl | H |
| 173 | | 2-iodo, 5-SCH$_3$ | S | 4-methyl-pent-3-enyl | H |
| 174 | | 2-iodo, 5-ethyl | S | 4-methyl-pent-3-enyl | H |
| 175 | | 2-iodo, 5-propyl | S | 4-methyl-pent-3-enyl | H |
| 176 | | 2-chloro, 5-SCH$_3$ | S | 4-methyl-pent-3-enyl | H |
| 177 | | 2-chloro, 5-ethyl | S | 4-methyl-pent-3-enyl | H |
| 178 | | 2-chloro, 5-propyl | S | 4-methyl-pent-3-enyl | H |
| 179 | | 2,5-SCH$_3$ | S | 4-methyl-pent-3-enyl | H |
| 180 | | 2-iodo, 4-fluoro, 5-methoxy | S | 4-methyl-pent-3-enyl | H |
| 181 | | 2-iodo, 3-fluoro, 5-methoxy | S | 4-methyl-pent-3-enyl | H |
| 182 | | 2-iodo, 6-fluoro, 5-methoxy | S | 4-methyl-pent-3-enyl | H |
| 183 | | 2-chloro, 3-fluoro, 5-methoxy | S | 4-methyl-pent-3-enyl | H |
| 184 | | 2-chloro, 4-fluoro, 5-methoxy | S | 4-methyl-pent-3-enyl | H |
| 185 | | 2-chloro-3,4,5-trimethoxy | S | 4-methyl-pent-3-enyl | H |
| 186 | | 2,3-diiodo, 5-methoxy | S | 4-methyl-pent-3-enyl | H |
| 187 | | 2,5-dichloro | S | 4-methyl-pent-3-enyl | H |
| 188 | | 2,5-dibromo | S | 4-methyl-pent-3-enyl | H |
| 189 | | 2-iodo, 4-chloro, 5-methoxy | S | 4-methyl-pent-3-enyl | H |
| 190 | | 2-iodo, 4-bromo, 5-methoxy | S | 4-methyl-pent-3-enyl | H |
| 191 | | 2,5-dimethoxy | S | 4-methyl-pent-3-enyl | F |
| 192 | | 2,3,5-trimethoxy | S | 4-methyl-pent-3-enyl | F |
| 193 | | 3,4,5-trimethoxy | S | 4-methyl-pent-3-enyl | F |
| 194 | | 2-iodo, 5-methoxy | S | 4-methyl-pent-3-enyl | F |
| 195 | | 2-bromo, 5-methoxy | S | 4-methyl-pent-3-enyl | F |
| 196 | | 2-chloro, 5-methoxy | S | 4-methyl-pent-3-enyl | F |
| 197 | | 2,4-diiodo, 5-methoxy | S | 4-methyl-pent-3-enyl | F |
| 198 | | 2,5-diiodo | S | 4-methyl-pent-3-enyl | F |
| 199 | | 2,4-diiodo | S | 4-methyl-pent-3-enyl | F |
| 200 | | 2-iodo, 5-SCH$_3$ | S | 4-methyl-pent-3-enyl | F |
| 201 | | 2-iodo, 5-ethyl | S | 4-methyl-pent-3-enyl | F |
| 202 | | 2-iodo, 5-propyl | S | 4-methyl-pent-3-enyl | F |
| 203 | | 2-chloro, 5-SCH$_3$ | S | 4-methyl-pent-3-enyl | F |
| 204 | | 2-chloro, 5-ethyl | S | 4-methyl-pent-3-enyl | F |
| 205 | | 2-chloro, 5-propyl | S | 4-methyl-pent-3-enyl | F |
| 206 | | 2,5-SCH$_3$ | S | 4-methyl-pent-3-enyl | F |
| 207 | | 2-iodo, 4-fluoro, 5-methoxy | S | 4-methyl-pent-3-enyl | F |
| 208 | | 2-iodo, 3-fluoro, 5-methoxy | S | 4-methyl-pent-3-enyl | F |
| 209 | | 2-iodo, 6-fluoro, 5-methoxy | S | 4-methyl-pent-3-enyl | F |
| 210 | | 2-chloro, 3-fluoro, 5-methoxy | S | 4-methyl-pent-3-enyl | F |
| 211 | | 2-chloro, 4-fluoro, 5-methoxy | S | 4-methyl-pent-3-enyl | F |
| 212 | | 2,3,4,5-tetraiodo | S | 4-methyl-pent-3-enyl | F |
| 213 | | 2,3-diiodo, 5-methoxy | S | 4-methyl-pent-3-enyl | F |
| 214 | | 2,5-dichloro | S | 4-methyl-pent-3-enyl | F |
| 215 | | 2,5-dibromo | S | 4-methyl-pent-3-enyl | F |
| 216 | | 2-Iodo, 4-chloro, 5-methoxy | S | 4-methyl-pent-3-enyl | F |
| 217 | | 2-iodo, 4-bromo, 5-methoxy | S | 4-methyl-pent-3-enyl | F |
| 218 | 11.2 | 2,5-dimethoxy | S | Pentyl | H |
| 219 | 9.2 | 2,5-dimethoxy | S | Butyl | H |
| 220 | 11.1 | 2,5-dimethoxy | S | H | H |
| 221 | 11.3 | 2,5-dimethoxy | S | pent-4-ynyl | H |
| 222 | 11.4 | 2,5-dimethoxy | S | butyronitrile | H |
| 223 | 11.5 | 2,5-dimethoxy | S | 3,3,3-trifluoropropyl | H |
| 224 | 11.6 | 2,5-dimethoxy | S | 4-chlorobutyl | H |
| 225 | 11.7 | 2,5-dimethoxy | S | 4-acetoxybutyl | H |
| 226 | 11.8 | 2,5-dimethoxy | S | 5-bromopentyl | H |
| 227 | 11.9 | 2,5-dimethoxy | S | 2-[1,3]dioxolan-2-yl-ethyl | H |
| 228 | 11.10 | 2,5-dimethoxy | S | 4-methyl-pent-3-enyl | H |
| 229 | 11.11 | 2,5-dimethoxy | S | 4-pentene | H |
| 230 | 11.12 | 2,5-dimethoxy | S | 3-hydroxypropyl | H |
| 231 | 10.1 | 2,5-dimethoxy | S | 4-methyl-pent-3-enyl | NH$_2$ |
| 232 | 10.2 | 2,5-dimethoxy | S | 4-methyl-pent-3-enyl | F |
| 233 | 9.1 | 3-hydoxy | S | butyl | H |
| 234 | 9.3 | 3-methoxy | S | butyl | H |
| 235 | 9.4 | 2-iodo-5-methoxy | S | butyl | H |
| 236 | 9.5 | 4-iodo-5-methoxy | S | Butyl | H |
| 237 | | 2,5-dimethoxy | CH$_2$ | Pentyl | H |
| 238 | 1.1 | 2,5-dimethoxy | CH$_2$ | Butyl | H |
| 239 | 3.8 | 2,5-dimethoxy | CH$_2$ | 4-ethylaminobutyl | H |
| 240 | | 2,5-dimethoxy | CH$_2$ | pent-4-ynyl | H |
| 241 | | 2,5-dimethoxy | CH$_2$ | butyronitrile | H |
| 242 | | 2,5-dimethoxy | CH$_2$ | 3,3,3-trifluoropropyl | H |

TABLE 1-continued

| No. | Ex. | W | X | Y | Z |
|---|---|---|---|---|---|
| 243 | 3.1 | 2,5-dimethoxy | CH₂ | 4-chlorobutyl | H |
| 244 | 3.11 | 2,5-dimethoxy | CH₂ | 5-acetoxypentyl | H |
| 245 | 3.5 | 2,5-dimethoxy | CH₂ | 5-bromopentyl | H |
| 246 | 3.3 | 2,5-dimethoxy | CH₂ | 2-[1,3]dioxolan-2-yl-ethyl | H |
| 247 | 3.12 | 2,5-dimethoxy | CH₂ | 3,3,3-trifluoropropyl | H |
| 248 | 3.13 | 2,5-dimethoxy | CH₂ | 4-pentene | H |
| 249 | | 2,5-dimethoxy | CH₂ | 3-hydroxypropyl | H |
| 250 | | 2,5-dimethoxy | CH₂ | 4-methyl-pent-3-enyl | NH₂ |
| 251 | 2.2 | 2,5-dimethoxy | CH₂ | 4-methyl-pent-3-enyl | F |
| 252 | | 2,5-dimethoxy | CH₂ | hexyl | H |
| 253 | | 2,5-dimethoxy | CH₂ | heptyl | H |
| 254 | | 2,5-dimethoxy | CH₂ | 3-cyclopropylpropyl | H |
| 255 | | 2,5-dimethoxy | CH₂ | 3-N,N-dimethylpropyl | H |
| 256 | | 2,5-dimethoxy | CH₂ | pentyl | F |
| 257 | | 2,5-dimethoxy | CH₂ | butyl | F |
| 258 | | 2,5-dimethoxy | CH₂ | 4-ethylaminobutyl | F |
| 259 | 2.1 | 2,5-dimethoxy | CH₂ | pent-4-ynyl | F |
| 260 | | 2,5-dimethoxy | CH₂ | butyronitrile | F |
| 261 | | 2,5-dimethoxy | CH₂ | 3,3,3-trifluoropropyl | F |
| 262 | | 2,5-dimethoxy | CH₂ | 4-chlorobutyl | F |
| 263 | | 2,5-dimethoxy | CH₂ | 4-acetoxybutyl | F |
| 264 | 2.4 | 2,5-dimethoxy | CH₂ | 5-bromopentyl | F |
| 265 | | 2,5-dimethoxy | CH₂ | 2-[1,3]dioxolan-2-yl-ethyl | F |
| 266 | | 2,5-dimethoxy | CH₂ | 3,3,3-trifluoropropyl | F |
| 267 | | 2,5-dimethoxy | CH₂ | 4-pentene | F |
| 268 | | 2,5-dimethoxy | CH₂ | 3-hydroxypropyl | F |
| 269 | | 2,5-dimethoxy | CH₂ | 4-cyclopropylbutyl | F |
| 270 | | 2,5-dimethoxy | CH₂ | 4-ethyl-pent-3-enyl | F |
| 271 | | 2,5-dimethoxy | CH₂ | hexyl | F |
| 272 | | 2,5-dimethoxy | CH₂ | heptyl | F |
| 273 | | 2,5-dimethoxy | CH₂ | 3-cyclopropylpropyl | F |
| 274 | | 2,5-dimethoxy | CH₂ | 3-N,N-dimethylpropyl | F |
| 275 | | 2,5-dimethoxy | O | pentyl | F |
| 276 | | 2,5-dimethoxy | O | butyl | F |
| 277 | | 2,5-dimethoxy | O | H | F |
| 278 | | 2,5-dimethoxy | O | pent-4-ynyl | F |
| 279 | | 2,5-dimethoxy | O | butyronitrile | F |
| 280 | | 2,5-dimethoxy | O | 3,3,3-trifluoropropyl | F |
| 281 | | 2,5-dimethoxy | O | 4-chlorobutyl | F |
| 282 | | 2,5-dimethoxy | O | 4-acetoxybutyl | F |
| 283 | | 2,5-dimethoxy | O | 5-bromopentyl | F |
| 284 | | 2,5-dimethoxy | O | 2-[1,3]dioxolan-2-yl-ethyl | F |
| 285 | | 2,5-dimethoxy | O | 4-methyl-pent-3-enyl | F |
| 286 | | 2,5-dimethoxy | O | 4-pentene | F |
| 287 | | 2,5-dimethoxy | O | 3-hydroxypropyl | F |
| 288 | | 2,5-dimethoxy | O | 4-methyl-pent-3-enyl | F |
| 289 | | 2,5-dimethoxy | O | 4-ethyl-pent-3-enyl | F |
| 290 | | 2,5-dimethoxy | O | hexyl | F |
| 291 | | 2,5-dimethoxy | O | heptyl | F |
| 292 | | 2,5-dimethoxy | O | 3-cyclopropylpropyl | F |
| 293 | | 2,5-dimethoxy | O | 3-N,N-dimethylpropyl | F |
| 294 | | 2,5-dimethoxy | O | pentyl | H |
| 295 | | 2,5-dimethoxy | O | butyl | H |
| 296 | | 2,5-dimethoxy | O | H | H |
| 297 | | 2,5-dimethoxy | O | pent-4-ynyl | H |
| 298 | | 2,5-dimethoxy | O | butyronitrile | H |
| 299 | | 2,5-dimethoxy | O | 3,3,3-trifluoropropyl | H |
| 300 | | 2,5-dimethoxy | O | 4-chlorobutyl | H |
| 301 | | 2,5-dimethoxy | O | 4-acetoxybutyl | H |
| 302 | | 2,5-dimethoxy | O | 5-bromopentyl | H |
| 303 | | 2,5-dimethoxy | O | 2-[1,3]dioxolan-2-yl-ethyl | H |
| 304 | | 2,5-dimethoxy | O | 4-methyl-pent-3-enyl | H |
| 305 | | 2,5-dimethoxy | O | 4-pentene | H |
| 306 | | 2,5-dimethoxy | O | 3-hydroxypropyl | H |
| 307 | | 2,5-dimethoxy | O | 4-cyclopropylbutyl | H |
| 308 | | 2,5-dimethoxy | O | 4-ethyl-pent-3-enyl | H |
| 309 | | 2,5-dimethoxy | O | hexyl | H |
| 310 | | 2,5-dimethoxy | O | heptyl | H |
| 311 | | 2,5-dimethoxy | O | 3-cyclopropylpropyl | H |
| 312 | | 2,5-dimethoxy | O | 3-N,N-dimethylpropyl | H |
| 313 | | 2-iodo-5-methoxy | O | pentyl | F |
| 314 | | 2-iodo-5-methoxy | O | butyl | F |
| 315 | | 2-iodo-5-methoxy | O | H | F |
| 316 | | 2-iodo-5-methoxy | O | pent-4-ynyl | F |
| 317 | | 2-iodo-5-methoxy | O | butyronitrile | F |
| 318 | | 2-iodo-5-methoxy | O | 3,3,3-trifluoropropyl | F |
| 319 | | 2-iodo-5-methoxy | O | 4-chlorobutyl | F |
| 320 | | 2-iodo-5-methoxy | O | 4-acetoxybutyl | F |
| 321 | | 2-iodo-5-methoxy | O | 5-bromopentyl | F |
| 322 | | 2-iodo-5-methoxy | O | 2-[1,3]dioxolan-2-yl-ethyl | F |
| 323 | | 2-iodo-5-methoxy | O | 4-methyl-pent-3-enyl | F |
| 324 | | 2-iodo-5-methoxy | O | 4-pentene | F |
| 325 | | 2-iodo-5-methoxy | O | 3-hydroxypropyl | F |
| 326 | | 2-iodo-5-methoxy | O | 4-cyclopropylbutyl | F |
| 327 | | 2-iodo-5-methoxy | O | 4-ethyl-pent-3-enyl | F |
| 328 | | 2-iodo-5-methoxy | O | hexyl | F |
| 329 | | 2-iodo-5-methoxy | O | heptyl | F |
| 330 | | 2-iodo-5-methoxy | O | 3-cyclopropylpropyl | F |
| 331 | | 2-iodo-5-methoxy | O | 3-N,N-dimethylpropyl | F |
| 332 | | 2-iodo-5-methoxy | O | pentyl | H |
| 333 | | 2-iodo-5-methoxy | O | butyl | H |
| 334 | | 2-iodo-5-methoxy | O | H | H |
| 335 | | 2-iodo-5-methoxy | O | pent-4-ynyl | H |
| 336 | | 2-iodo-5-methoxy | O | butyronitrile | H |
| 337 | | 2-iodo-5-methoxy | O | 3,3,3-trifluoropropyl | H |
| 338 | | 2-iodo-5-methoxy | O | 4-chlorobutyl | H |
| 339 | | 2-iodo-5-methoxy | O | 4-acetoxybutyl | H |
| 340 | | 2-iodo-5-methoxy | O | 5-bromopentyl | H |
| 341 | | 2-iodo-5-methoxy | O | 2-[1,3]dioxolan-2-yl-ethyl | H |
| 342 | | 2-iodo-5-methoxy | O | 4-methyl-pent-3-enyl | H |
| 343 | | 2-iodo-5-methoxy | O | 4-pentene | H |
| 344 | | 2-iodo-5-methoxy | O | 3-hydroxypropyl | H |
| 345 | | 2-iodo-5-methoxy | O | 4-cyclopropylbutyl | H |
| 346 | | 2-iodo-5-methoxy | O | 4-ethyl-pent-3-enyl | H |
| 347 | | 2-iodo-5-methoxy | O | hexyl | H |
| 348 | | 2-iodo-5-methoxy | O | heptyl | H |
| 349 | | 2-iodo-5-methoxy | O | 3-cyclopropylpropyl | H |
| 350 | | 2-iodo-5-methoxy | O | 3-N,N-dimethylpropyl | H |
| 351 | | 2-iodo-5-methoxy | NH | pentyl | F |
| 352 | | 2-iodo-5-methoxy | NH | butyl | F |
| 353 | | 2-iodo-5-methoxy | NH | H | F |

TABLE 1-continued

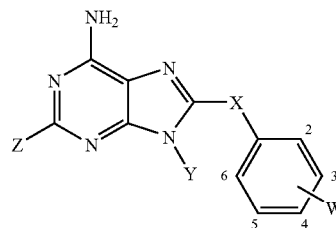

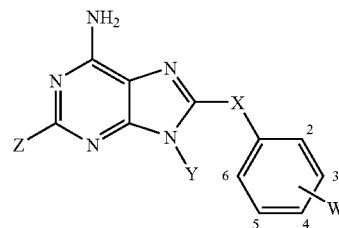

| No. | Ex. | W | X | Y | Z |
|---|---|---|---|---|---|
| 354 | | 2-iodo-5-methoxy | NH | pent-4-ynyl | F |
| 355 | | 2-iodo-5-methoxy | NH | butyronitrile | F |
| 356 | | 2-iodo-5-methoxy | NH | 3,3,3-trifluoropropyl | F |
| 357 | | 2-iodo-5-methoxy | NH | 4-chlorobutyl | F |
| 358 | | 2-iodo-5-methoxy | NH | 4-acetoxybutyl | F |
| 359 | | 2-iodo-5-methoxy | NH | 5-bromopentyl | F |
| 360 | | 2-iodo-5-methoxy | NH | 2-[1,3]dioxolan-2-yl-ethyl | F |
| 361 | | 2-iodo-5-methoxy | NH | 4-methyl-pent-3-enyl | F |
| 362 | | 2-iodo-5-methoxy | NH | 4-pentene | F |
| 363 | | 2-iodo-5-methoxy | NH | 3-hydroxypropyl | F |
| 364 | | 2-iodo-5-methoxy | NH | 4-cyclopropylbutyl | F |
| 365 | | 2-iodo-5-methoxy | NH | 4-ethyl-pent-3-enyl | F |
| 366 | | 2-iodo-5-methoxy | NH | hexyl | F |
| 367 | | 2-iodo-5-methoxy | NH | heptyl | F |
| 368 | | 2-iodo-5-methoxy | NH | 3-cyclopropylpropyl | F |
| 369 | | 2-iodo-5-methoxy | NH | 3-N,N-dimethylpropyl | F |
| 370 | | 2-iodo-5-methoxy | NH | pentyl | H |
| 371 | | 2-iodo-5-methoxy | NH | butyl | H |
| 372 | | 2-iodo-5-methoxy | NH | H | H |
| 373 | | 2-iodo-5-methoxy | NH | pent-4-ynyl | H |
| 374 | | 2-iodo-5-methoxy | NH | butyronitrile | H |
| 375 | | 2-iodo-5-methoxy | NH | 3,3,3-trifluoropropyl | H |
| 376 | | 2-iodo-5-methoxy | NH | 4-chlorobutyl | H |
| 377 | | 2-iodo-5-methoxy | NH | 4-acetoxybutyl | H |
| 378 | | 2-iodo-5-methoxy | NH | 5-bromopentyl | H |
| 379 | | 2-iodo-5-methoxy | NH | 2-[1,3]dioxolan-2-yl-ethyl | H |
| 380 | | 2-iodo-5-methoxy | NH | 4-methyl-pent-3-enyl | H |
| 381 | | 2-iodo-5-methoxy | NH | 4-pentene | H |
| 382 | | 2-iodo-5-methoxy | NH | 3-hydroxypropyl | H |
| 383 | | 2-iodo-5-methoxy | NH | 4-cyclopropylbutyl | H |
| 384 | | 2-iodo-5-methoxy | NH | 4-ethyl-pent-3-enyl | H |
| 385 | | 2-iodo-5-methoxy | NH | hexyl | H |
| 386 | | 2-iodo-5-methoxy | NH | heptyl | H |
| 387 | | 2-iodo-5-methoxy | NH | 3-cyclopropylpropyl | H |
| 388 | | 2-iodo-5-methoxy | NH | 3-N,N-dimethylpropyl | H |
| 389 | | 2,5-dimethoxy | NH | pentyl | F |
| 390 | | 2,5-dimethoxy | NH | butyl | F |
| 391 | | 2,5-dimethoxy | NH | H | F |
| 392 | | 2,5-dimethoxy | NH | pent-4-ynyl | F |
| 393 | | 2,5-dimethoxy | NH | butyronitrile | F |
| 394 | | 2,5-dimethoxy | NH | 3,3,3-trifluoropropyl | F |
| 395 | | 2,5-dimethoxy | NH | 4-chlorobutyl | F |
| 396 | | 2,5-dimethoxy | NH | 4-acetoxybutyl | F |
| 397 | | 2,5-dimethoxy | NH | 5-bromopentyl | F |
| 398 | | 2,5-dimethoxy | NH | 2-[1,3]dioxolan-2-yl-ethyl | F |
| 399 | | 2,5-dimethoxy | NH | 4-methyl-pent-3-enyl | F |
| 400 | | 2,5-dimethoxy | NH | 4-pentene | F |
| 401 | | 2,5-dimethoxy | NH | 3-hydroxypropyl | F |
| 402 | | 2,5-dimethoxy | NH | 4-cyclopropylbutyl | F |
| 403 | | 2,5-dimethoxy | NH | 4-ethyl-pent-3-enyl | F |
| 404 | | 2,5-dimethoxy | NH | hexyl | F |
| 405 | | 2,5-dimethoxy | NH | heptyl | F |
| 406 | | 2,5-dimethoxy | NH | 3-cyclopropylpropyl | F |
| 407 | | 2,5-dimethoxy | NH | 3-N,N-dimethylpropyl | F |
| 408 | | 2,5-dimethoxy | NH | pentyl | H |
| 409 | | 2,5-dimethoxy | NH | butyl | H |
| 410 | | 2,5-dimethoxy | NH | H | H |
| 411 | | 2,5-dimethoxy | NH | pent-4-ynyl | H |
| 412 | | 2,5-dimethoxy | NH | butyronitrile | H |
| 413 | | 2,5-dimethoxy | NH | 3,3,3-trifluoropropyl | H |
| 414 | | 2,5-dimethoxy | NH | 4-chlorobutyl | H |
| 415 | | 2,5-dimethoxy | NH | 4-acetoxybutyl | H |
| 416 | | 2,5-dimethoxy | NH | 5-bromopentyl | H |
| 417 | | 2,5-dimethoxy | NH | 2-[1,3]dioxolan-2-yl-ethyl | H |
| 418 | | 2,5-dimethoxy | NH | 4-methyl-pent-3-enyl | H |
| 419 | | 2,5-dimethoxy | NH | 4-pentene | H |
| 420 | | 2,5-dimethoxy | NH | 3-hydroxypropyl | H |
| 421 | | 2,5-dimethoxy | NH | 4-cyclopropylbutyl | H |
| 422 | | 2,5-dimethoxy | NH | 4-ethyl-pent-3-enyl | H |
| 423 | | 2,5-dimethoxy | NH | hexyl | H |
| 424 | | 2,5-dimethoxy | NH | heptyl | H |
| 425 | | 2,5-dimethoxy | NH | 3-cyclopropylpropyl | H |
| 426 | | 2,5-dimethoxy | NH | 3-N,N-dimethylpropyl | H |
| 427 | | 2,5-dimethoxy | S | pentyl | F |
| 428 | | 2,5-dimethoxy | S | 4-ethylaminobutyl | H |
| 429 | | 2,5-dimethoxy | S | 4-ethylaminobutyl | F |
| 430 | | 2,5-dimethoxy | S | pent-4-ynyl | F |
| 431 | | 2,5-dimethoxy | S | butyronitrile | F |
| 432 | | 2,5-dimethoxy | S | 3,3,3-trifluoropropyl | F |
| 433 | | 2,5-dimethoxy | S | 4-chlorobutyl | F |
| 434 | | 2,5-dimethoxy | S | 4-acetoxybutyl | F |
| 435 | | 2,5-dimethoxy | S | 5-bromopentyl | F |
| 436 | | 2,5-dimethoxy | S | 2-[1,3]dioxolan-2-yl-ethyl | F |
| 437 | | 2,5-dimethoxy | S | butyl | F |
| 438 | | 2,5-dimethoxy | S | 4-pentene | F |
| 439 | | 2,5-dimethoxy | S | 3-hydroxypropyl | F |
| 440 | | 2,5-dimethoxy | S | 4-methyl-pent-3-enyl | F |
| 441 | | 2,5-dimethoxy | S | 4-ethyl-pent-3-enyl | F |
| 442 | | 3-hydoxy | S | butyl | F |
| 443 | | 2,5-dimethoxy | S | 2-(dimethyl-bicyclo[3.1.1]hept-2-en-2-yl)-ethyl | F |
| 444 | | 2-Iodo-5-methoxy | S | butyl | F |
| 445 | | 4-Iodo-5-methoxy | S | butyl | F |
| 446 | | 2,5-dimethoxy | S | hexan-6-ol | H |
| 447 | | 2,5-dimethoxy | S | pentan-5-ol | H |
| 448 | | 2,5-dimethoxy | S | butan-4-ol | H |
| 449 | | 2,5-dimethoxy | S | hexan-6-ol | F |
| 450 | | 2,5-dimethoxy | S | pentan-5-ol | F |
| 451 | | 2,5-dimethoxy | S | butan-4-ol | F |
| 452 | | 2-iodo-5-methoxy | S | hexan-6-ol | H |
| 453 | | 2-iodo-5-methoxy | S | pentan-5-ol | H |
| 454 | | 2-iodo-5-methoxy | S | butan-4-ol | H |
| 455 | | 2-iodo-5-methoxy | S | hexan-6-ol | F |
| 456 | | 2-iodo-5-methoxy | S | pentan-5-ol | F |
| 457 | | 2-iodo-5-methoxy | S | butan-4-ol | F |
| 458 | | 2-iodo-5-methoxy | S | hexan-6-ol | H |
| 459 | | 2-iodo-5-methoxy | S | pentan-5-ol | H |
| 460 | | 2,5-dimethoxy | CH$_2$ | hexan-6-ol | H |
| 461 | | 2,5-dimethoxy | CH$_2$ | pentan-5-ol | H |
| 462 | | 2,5-dimethoxy | CH$_2$ | butan-4-ol | H |
| 463 | 3.9 | 2,5-dimethoxy | CH$_2$ | hexan-6-ol | F |
| 464 | | 2,5-dimethoxy | CH$_2$ | pentan-5-ol | F |
| 465 | | 2,5-dimethoxy | CH$_2$ | butan-4-ol | F |
| 466 | | 2-iodo-5-methoxy | CH$_2$ | hexan-6-ol | H |
| 467 | | 2-iodo-5-methoxy | CH$_2$ | pentan-5-ol | H |

TABLE 1-continued

| No. | Ex. | W | X | Y | Z |
|---|---|---|---|---|---|
| 468 | | 2-iodo-5-methoxy | CH₂ | butan-4-ol | H |
| 469 | | 2-iodo-5-methoxy | CH₂ | hexan-6-ol | F |
| 470 | | 2-iodo-5-methoxy | CH₂ | pentan-5-ol | F |
| 471 | | 2-iodo-5-methoxy | CH₂ | butan-4-ol | F |
| 472 | | 2-iodo-5-methoxy | CH₂ | hexan-6-ol | H |
| 473 | | 2-iodo-5-methoxy | CH₂ | pentan-5-ol | H |
| 474 | 2.3 | 2,5-dimethoxy | CH₂ | pent-4-enyl | F |
| 475 | 3.6 | 2,5-dimethoxy | CH₂ | 5-bromo-3-methyl-pentyl | H |
| 476 | 3.6 | 2,5-dimethoxy | CH₂ | 5-chloro-pentyl | H |
| 477 | 3.10 | 2,5-dimethoxy | CH₂ | dimethyl-bicyclo[3.1.1]hept-2-en-2-yl)-ethyl | H |
| 478 | | 2-iodo-5-methoxy | CH₂ | pentyl | H |
| 479 | 4.1 | 2-iodo-5-methoxy | CH₂ | butyl | H |
| 480 | | 2-iodo-5-methoxy | CH₂ | 4-ethylaminobutyl | H |
| 481 | | 2-iodo-5-methoxy | CH₂ | pent-4-ynyl | H |
| 482 | | 2-iodo-5-methoxy | CH₂ | butyronitrile | H |
| 483 | | 2-iodo-5-methoxy | CH₂ | 3,3,3-trifluoropropyl | H |
| 484 | | 2-iodo-5-methoxy | CH₂ | 4-chlorobutyl | H |
| 485 | | 2-iodo-5-methoxy | CH₂ | 5-acetoxypentyl | H |
| 486 | | 2-iodo-5-methoxy | CH₂ | 5-bromopentyl | H |
| 487 | | 2-iodo-5-methoxy | CH₂ | 2-[1,3]dioxolan-2-yl-ethyl | H |
| 488 | | 2-iodo-5-methoxy | CH₂ | 3,3,3-trifluoropropyl | H |
| 489 | | 2-iodo-5-methoxy | CH₂ | 4-pentene | H |
| 490 | | 2-iodo-5-methoxy | CH₂ | 3-hydroxypropyl | H |
| 491 | 4.2 | 5-iodo-2-methoxy | CH₂ | butyl | H |
| 492 | | 2-iodo-5-methoxy | CH₂ | 4-methyl-pent-3-enyl | F |
| 493 | | 2-iodo-5-methoxy | CH₂ | hexyl | H |
| 494 | | 2-iodo-5-methoxy | CH₂ | heptyl | H |
| 495 | | 2-iodo-5-methoxy | CH₂ | 3-cyclopropylpropyl | H |
| 496 | | 2-iodo-5-methoxy | CH₂ | 3-N,N-dimethylpropyl | H |
| 497 | 4.3 | 5-ethyl-2-methoxy | CH₂ | butyl | H |
| 498 | 4.4 | 2-bromo-5-methoxy | CH₂ | butyl | H |
| 499 | 4.5 | 2-bromo-5-methoxy | CH₂ | 4-methyl-pent-3-enyl | H |
| 500 | 4.6 | 2-bromo-5-methoxy | CH₂ | pent-4-ynyl | H |
| 501 | 5.1 | 5-ethyl-2-methoxy | CH₂ | butyl | H |
| 502 | 5.2 | 5-butyl-2-methoxy | CH₂ | butyl | H |
| 503 | 5.3 | 5-vinyl-2-methoxy | CH₂ | butyl | H |
| 504 | 6.1 | 2,5-dimethoxy-4-nitro | CH₂ | pent-4-ynyl | F |
| 505 | 6.2 | 3,5-dimethoxy-2-nitro | CH₂ | butyl | H |
| 506 | 6.3 | 3,5-dimethoxy-4-amino | CH₂ | 4-methyl-pent-3-enyl | H |
| 507 | 6.4 | 2,5-dimethoxy-4-amino | CH₂ | butyl | H |
| 508 | 6.5 | 3,5-dimethoxy-2-amino | CH₂ | butyl | H |
| 509 | 6.6 | 4-methoxy benzaldehyde-O-methyl-oxime | CH₂ | butyl | H |
| 510 | 7.1 | 4-methoxy benzaldehyde | CH₂ | butyl | H |
| 511 | 8.1 | 3,4-dichloro benzyl | CH₂ | butyl | H |
| 512 | | 2-iodo-5-methoxy | S | pentyl | H |
| 513 | | 2-iodo-5-methoxy | S | butyl | H |
| 514 | | 2-iodo-5-methoxy | S | 4-ethylaminobutyl | H |
| 515 | | 2-iodo-5-methoxy | S | pent-4-ynyl | H |
| 516 | | 2-iodo-5-methoxy | S | butyronitrile | H |
| 517 | | 2-iodo-5-methoxy | S | 3,3,3-trifluoropropyl | H |
| 518 | | 2-iodo-5-methoxy | S | 4-chlorobutyl | H |
| 519 | | 2-iodo-5-methoxy | S | 5-acetoxypentyl | H |
| 520 | | 2-iodo-5-methoxy | S | 5-bromopentyl | H |
| 521 | | 2-iodo-5-methoxy | S | 2-[1,3]dioxolan-2-yl-ethyl | H |
| 522 | | 2-iodo-5-methoxy | S | 3,3,3-trifluoropropyl | H |
| 523 | | 2-iodo-5-methoxy | S | 4-pentene | H |
| 524 | | 2-iodo-5-methoxy | S | 3-hydroxypropyl | H |
| 525 | | 2-iodo-5-methoxy | S | 4-methyl-pent-3-enyl | NH2 |
| 526 | | 2-iodo-5-methoxy | S | 4-methyl-pent-3-enyl | F |
| 527 | | 2-iodo-5-methoxy | S | hexyl | H |
| 528 | | 2-iodo-5-methoxy | S | heptyl | H |
| 529 | | 2-iodo-5-methoxy | S | 3-cyclopropylpropyl | H |
| 530 | | 2-iodo-5-methoxy | S | 3-N,N-dimethylpropyl | H |
| 531 | | 2-iodo-5-methoxy | S | pentyl | F |
| 532 | | 2-iodo-5-methoxy | S | butyl | F |
| 533 | | 2-iodo-5-methoxy | S | 4-ethylaminobutyl | F |
| 534 | | 2-iodo-5-methoxy | S | pent-4-ynyl | F |
| 535 | | 2-iodo-5-methoxy | S | butyronitrile | F |
| 536 | | 2-iodo-5-methoxy | S | 3,3,3-trifluoropropyl | F |
| 537 | | 2-iodo-5-methoxy | S | 4-chlorobutyl | F |
| 538 | | 2-iodo-5-methoxy | S | 4-acetoxybutyl | F |
| 539 | | 2-iodo-5-methoxy | S | 5-bromopentyl | F |
| 540 | | 2-iodo-5-methoxy | S | 2-[1,3]dioxolan-2-yl-ethyl | F |
| 541 | | 2-iodo-5-methoxy | S | 3,3,3-trifluoropropyl | F |
| 542 | | 2-iodo-5-methoxy | S | 4-pentene | F |
| 543 | | 2-iodo-5-methoxy | S | 3-hydroxypropyl | F |
| 544 | | 2-iodo-5-methoxy | S | 4-cyclopropylbutyl | F |
| 545 | | 2-iodo-5-methoxy | S | 4-ethyl-pent-3-enyl | F |
| 546 | | 2-iodo-5-methoxy | S | hexyl | F |
| 547 | | 2-iodo-5-methoxy | S | heptyl | F |
| 548 | | 2-iodo-5-methoxy | S | 3-cyclopropylpropyl | F |
| 549 | | 2-iodo-5-methoxy | S | 3-N,N-dimethylpropyl | F |
| 550 | | 2-iodo-5-methoxy | S | pentyl | Cl |
| 551 | | 2-iodo-5-methoxy | S | butyl | Cl |
| 552 | | 2-iodo-5-methoxy | S | 4-ethylaminobutyl | Cl |
| 553 | | 2-iodo-5-methoxy | S | pent-4-ynyl | Cl |
| 554 | | 2-iodo-5-methoxy | S | butyronitrile | Cl |
| 555 | | 2-iodo-5-methoxy | S | 3,3,3-trifluoropropyl | Cl |
| 556 | | 2-iodo-5-methoxy | S | 4-chlorobutyl | Cl |
| 557 | | 2-iodo-5-methoxy | S | 4-acetoxybutyl | Cl |
| 558 | | 2-iodo-5-methoxy | S | 5-bromopentyl | Cl |
| 559 | | 2-iodo-5-methoxy | S | 2-[1,3]dioxolan-2-yl-ethyl | Cl |
| 560 | | 2-iodo-5-methoxy | S | 3,3,3-trifluoropropyl | Cl |
| 561 | | 2-iodo-5-methoxy | S | 4-pentene | Cl |
| 562 | | 2-iodo-5-methoxy | S | 3-hydroxypropyl | Cl |
| 563 | | 2-iodo-5-methoxy | S | 4-cyclopropylbutyl | Cl |
| 564 | | 2-iodo-5-methoxy | S | 4-ethyl-pent-3-enyl | Cl |
| 565 | | 2-iodo-5-methoxy | S | hexyl | Cl |
| 566 | | 2-iodo-5-methoxy | S | heptyl | Cl |
| 567 | | 2-iodo-5-methoxy | S | 3-cyclopropylpropyl | Cl |
| 568 | | 2-iodo-5-methoxy | S | 3-N,N-dimethylpropyl | Cl |
| 569 | | 2-iodo-5-methoxy | S | 4-methyl-pent-3-enyl | NH₂ |
| 570 | | 2-iodo-5-methoxy | S | 4-methyl-pent-3-enyl | Cl |
| 571 | | 2-iodo-5-methoxy | S | pent-4-ynyl | Cl |
| 572 | 9.11 | 2,5-dichloro | S | butyl | H |
| 573 | | | | | |

TABLE 1-continued

| No. | Ex. | W | X | Y | Z |
|---|---|---|---|---|---|
| 574 | 9.12 | 2,4,5-trichloro | S | butyl | H |
| 575 | 2.5 | 2,5-dimethoxy | CH$_2$ | pent-4-ynyl | Cl |

Particularly preferred in Table 1 are compounds 1, 4, 31, 55, 58, 85, 113, 137, 140, 167, 191, 194, 221, 224, 226, 228, 232, 234, 235, 236, 239, 245, 248, 251, 259, 452, 453, 454, 455, 456, 457, 463, 469, 470, 471, 571 and 572, with the most preferred compounds being 1, 85, 113, 137, 140, 167, 191, 194, 221, 228, 239, 251, 259, 452, 453, 455, 571 and 572.

Other compounds of the invention are based on the following formula, having illustrative species as described in Table 2:

TABLE 2

| No. | Ex. | E | X | L | Z |
|---|---|---|---|---|---|
| 576 | 9.8 | H | S | S | H |
| 577 | 9.9 | 5-chloro | S | S | H |
| 578 | 9.10 | 5-methoxy | S | S | H |

The foregoing aspects and embodiments can also include tautomers of the compounds. For example, referring to structures I-IV, above, structure II is a tautomeric form of structure I when A is OH (OR$^3$ where R$^3$ is H), structure III is another tautomeric form of structure I (when Z is OH), and structure IV is yet another tautomeric form of structure I in the event that both A and Z are OH. All four tautomeric possibilities can be represented essentially as shown in structure I, except that dashed lines appear between atoms 1 and 6 and 2 and 3, and between A and 6 and Z and 2, e.g., as shown:

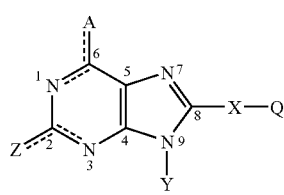

The foregoing aspects and embodiments can also include prodrugs and/or pharmaceutically acceptable salts of the compounds shown.

The foregoing aspects and embodiments can also include varying levels and types of substitution on one or more of entities A, B, Q, W, X, Y and Z, above, where that entity is not already solely hydrogen but rather is a multi-atom substituent that contains one or more hydrogens that can be substituted for, e.g., with a halogen or combination of other atoms or chemical group(s). In some embodiments, there may be a range of from 0 to 25 or more collective substitutions (for all of A, B, Q, W, X, Y and Z), and any range in between. The substitutions may be made or included at any point in the synthesis of the final compounds, as appropriate, including, e.g., in the starting reagents or intermediates of the reaction scheme(s) used, or following the synthesis of one final product to convert it into another. The following embodiments are illustrative:

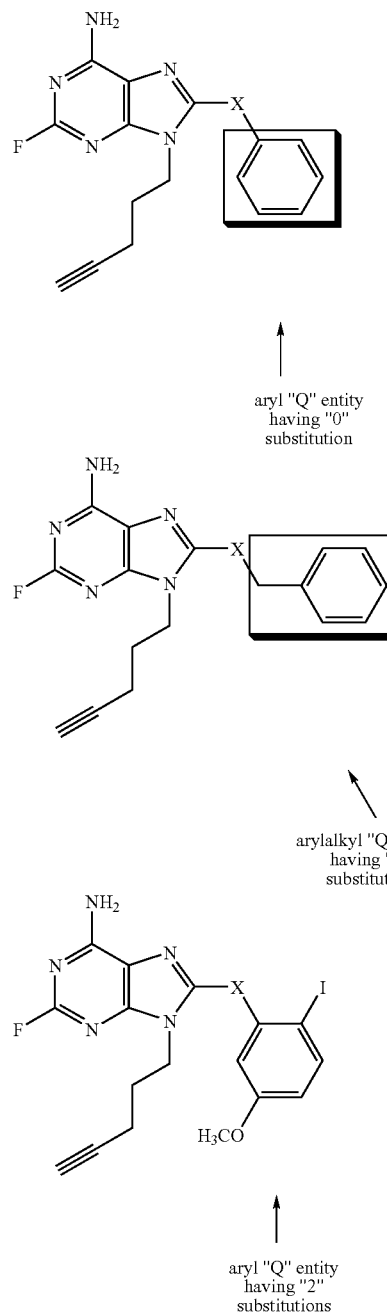

-continued

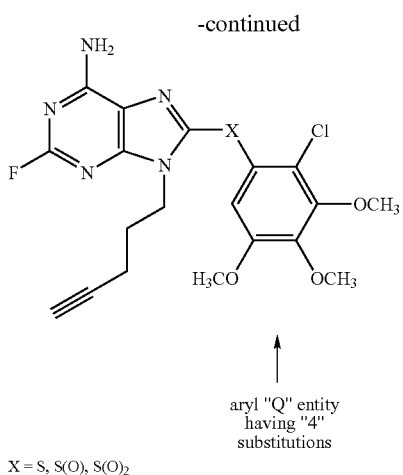

X = S, S(O), S(O)$_2$ aryl "Q" entity
having "4"
substitutions

In another aspect, the invention features pharmaceutical compositions containing one or more of the compounds or pharmaceutically acceptable salts thereof described for the preceding aspects. These additionally include one or more pharmaceutically acceptable carriers and/or excipients.

Another aspect of the invention features methods of making the compounds of the preceding aspects. These are described in greater detail in the next section and the examples to follow. Related aspects of the invention embrace intermediates of/in these synthetic methods to the extent they are novel, either alone or standing in the context of the specific synthesis objective.

In yet another aspect, the invention features methods of inhibiting an HSP90 molecule with a compound according to any of the previous aspects and embodiments. HSP90 proteins are highly conserved in nature (see, e.g., NCBI accession #'s P07900 and XM 004515 (human α and β HSP90, respectively), P11499 (mouse), AAB2369 (rat), P46633 (chinese hamster), JC1468 (chicken), AAF69019 (flesh fly), AAC21566 (zebrafish), AAD30275 (salmon), O02075 (pig), NP 015084 (yeast), and CAC29071 (frog). Grp94 and Trap-1 are related molecules falling within the definition of an HSP90- as used herein. There are thus many different HSP90s, all with expected similar effect and inhibition capabilities. The HSP90 inhibitors of the invention may be specifically directed against an HSP90 of the specific host patient or may be identified based on reactivity against an HSP90 homolog from a different species, or an HSP90 variant. The methods feature contacting a cell having an HSP90 with a pharmaceutically effective amount of a compound or pharmaceutical composition according to any one of the preceding aspects. The cell is preferably a mammalian cell, and more preferably a human cell, although any cell-type from any life-form that contains an HSP90, including non-mammalian lines, is contemplated for the invention. The method can be "in vitro", e.g., contacting a cell line in culture, or else can be "in vivo", e.g., contacting a cell inside a live organism. One type of in vivo administration is made "in situ", or directly to a specific cell or group of cells within an organism, e.g, intratumorally. "Ex vivo" procedures are also envisioned wherein the cells are first removed from a patient, treated by contacting them with the compounds or compositions of the invention, and then administered back to a patient or "the" patient. The compounds and compositions can be administered in a variety of ways, e.g., intravenously, parenterally, orally, bucally, intramuscularly, sublingually, topically, by aerosol, subcutaneously, intramuscularly, intraperitoneally, rectally, vaginally, intratumorally, or peritumorally.

In some aspects, the compounds or compositions are administered to treat or prevent a cancer, e.g., a breast cancer, melanoma, lung cancer, etc. In some embodiments, these compounds may be used in combination with or as an adjuvant/sensitizer for any chemotherapy regimen. Such regimens may include the use of other anti-cancer compounds, e.g., TAXOL®, HERCEPTIN®, GLEEVEC®, etc. The additions may be made simultaneously or sequentially and, if the latter, in any order.

In other aspects, the compounds or compositions are used for non-oncology applications, e.g., treating inflammation, infectious disease, autoimmune disease, and ischemia.

Any of the above described aspects and embodiments of the invention can be combined where practical. The individual methods prescribed do not preclude the utilization of other, unspecified steps, and those of ordinary skill in the art will appreciate that additional steps and compounds may also be usefully incorporated within the spirit of the invention.

Advantages of the invention depend on the specific aspect and embodiment and may include one or more of: ease of synthesis and/or formulation, solubility, and IC$_{50}$ relative to previously existing compounds in the same or different classes of HSP90 inhibitors. Other advantages, aspects, and embodiments will be apparent from the figures, the detailed description and claims to follow.

DETAILED DESCRIPTION OF THE INVENTION

Definitions

Figure 1:
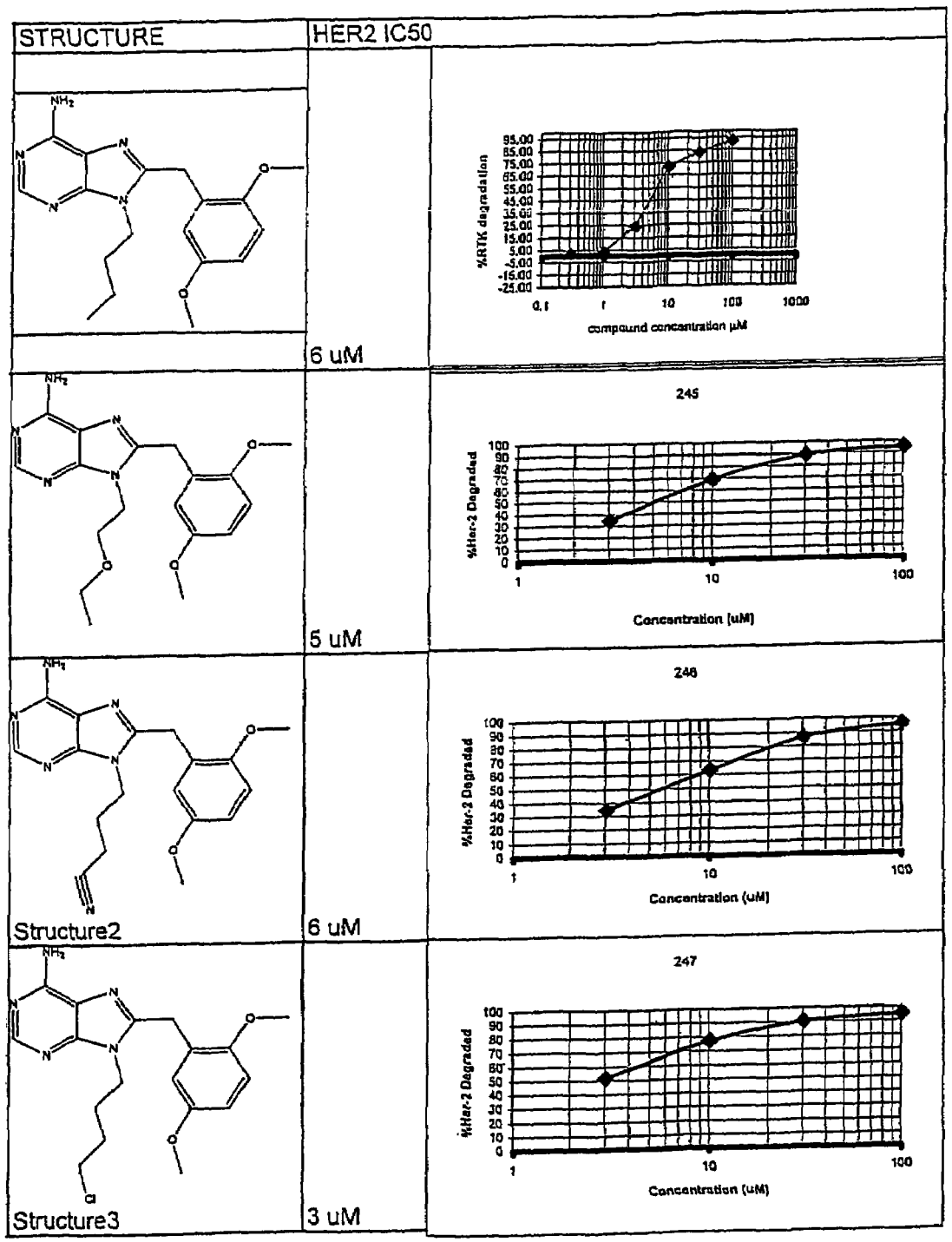
FIG. 1 shows IC$_{50}$ values for compounds of Table 3, Example 3, as measured using Her-2 degradation studies.
Figure 1:
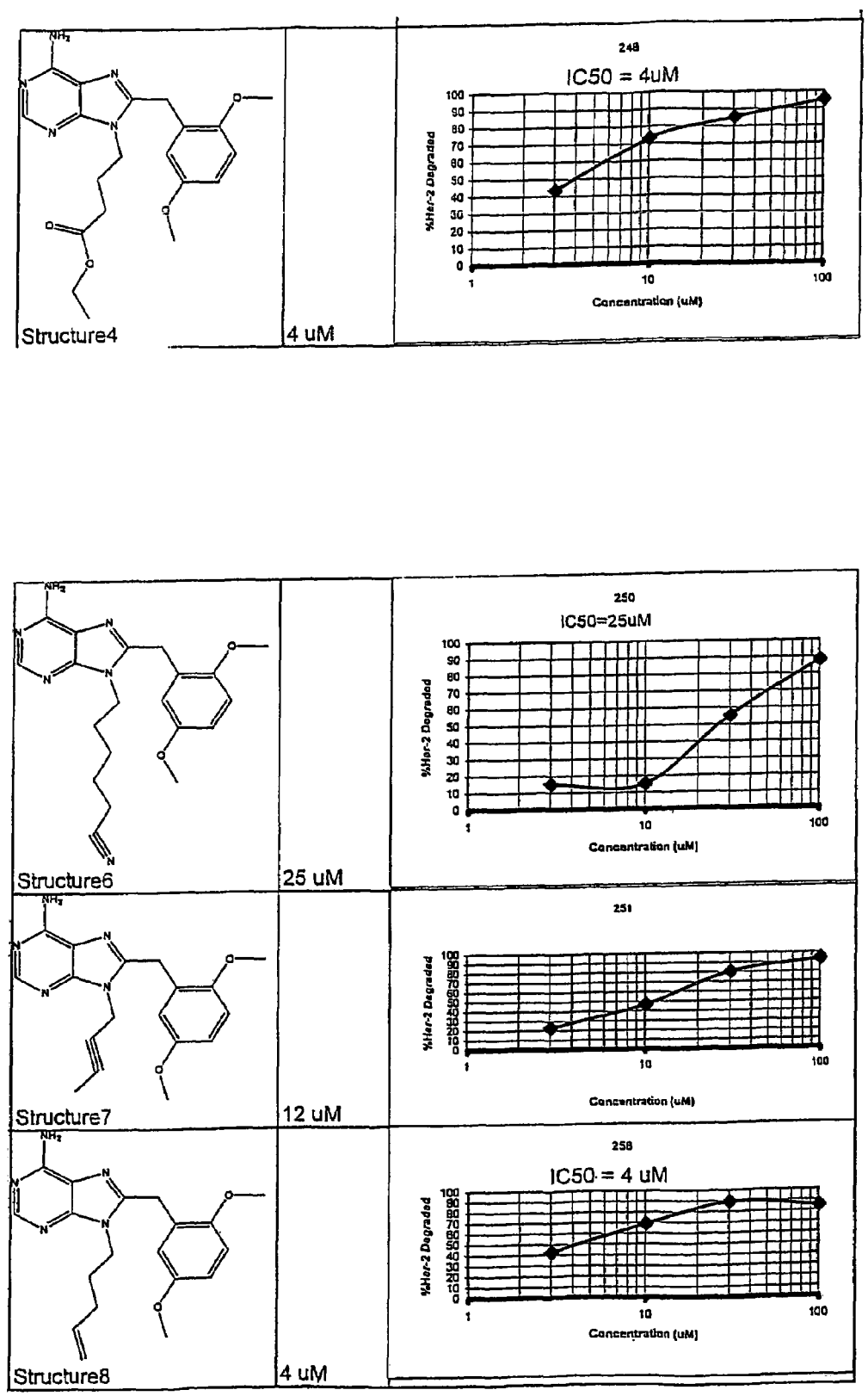

A "pharmaceutically acceptable salt" may be prepared for any compound of the invention having a functionality capable of forming a salt, for example an acid or base functionality. Pharmaceutically acceptable salts may be derived from organic or inorganic acids and bases.

Compounds of the invention that contain one or more basic functional groups, e.g., amino or alkylamino, are capable of forming pharmaceutically acceptable salts with pharmaceutically acceptable organic and inorganic acids. These salts can be prepared in situ during the final isolation and purification of the compounds of the invention, or by separately reacting a purified compound of the invention in its free base form with a suitable organic or inorganic acid, and isolating the salt thus formed. Examples of suitable acids include hydrochloric, hydrobromic, sulfuric, nitric, perchloric, fumaric, maleic, phosphoric, glycolic, gluconic, lactic, salicylic, succinic, toluene-p-sulfonic, tartaric, acetic, citric, methanesulfonic, formic, benzoic, malonic, naphthalene-2-sulfonic, benzenesulfonic, 1,2 ethanesulfonic acid (edisylate), galactosyl-d-gluconic acid, and the like. Other acids, such as oxalic acid, while not themselves pharmaceutically acceptable, may be employed in the preparation of salts useful as intermediates in obtaining the compounds of this invention and their pharmaceutically acceptable acid addition salts. See, e.g., Berge et al. "Pharmaceutical Salts", J. Pharm. Sci. 66:1-19 (1977).

Compounds of the present invention that contain one or more acidic functional groups are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Illustrative examples of some of the bases that can be used include sodium hydroxide, potassium hydroxide, choline hydroxide, sodium carbonate, and the like. Representative organic amines useful for the formation of base addition salts include ethylamine, diethylamine, ethylenediamine, ethanolamine, diethanolamine, piperazine and the like. See, for example, Berge et al., supra.

"Prodrugs" are derivative compounds derivatized by the addition of a group that endows greater solubility to the compound desired to be delivered. Once in the body, the prodrug is typically acted upon by an enzyme, e.g., an esterase, amidase, or phosphatase, to generate the active compound. Suitable positions for derivatization of the compounds of the invention to create "prodrugs" include but are not limited to the Y group, the phenyl ring of the purines, and the Q group. Those of ordinary skill in the art have the knowledge and means to accomplish this without undue experimentation.

"Tautomers" are compounds whose structures differ in arrangements of atoms, but which exist in equilibrium. By way of example, the structure shown below and designated T is in equilibrium with a second tautomeric form designated T'.

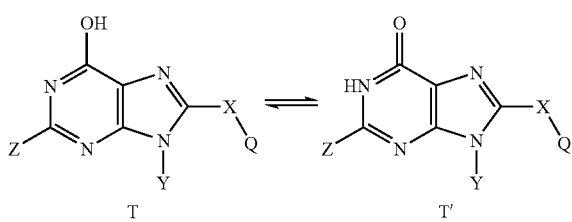

The predominance of one tautomer versus another is controlled by factors which include but are not limited to the nature of the solvent, temperature, pressure, the presence or absence of other molecules, and the nature of substituents on the molecule having tautomeric forms.

The term "alkyl," alone or in combination, refers to an optionally substituted straight-chain, optionally substituted branched-chain, or optionally substituted cyclic alkyl radical having from 1 to about 30 carbons, more preferably 1 to 12 carbons. Examples of alkyl radicals include methyl, ethyl, n-propyl, isopropyl, n-butyl, isobutyl, sec-butyl, tert-butyl, tert-amyl, pentyl, hexyl, heptyl, octyl and the like. The term "cycloalkyl" embraces cyclic configurations, is subsumed within the definition of alkyl and specifically refers to a monocyclic, bicyclic, tricyclic, and higher multicyclic alkyl radicals wherein each cyclic moiety has from 3 to about 8 carbon atoms. Examples of cycloalkyl radicals include cyclopropyl, cyclobutyl, cyclopentyl, cyclohexyl and the like. A "lower alkyl" is a shorter alkyl, e.g., one containing from 1 to about 6 carbon atoms.

The term "alkyl," alone or in combination, refers to an optionally substituted straight-chain, or optionally substituted branched-chain, alkyl radical having from 1 to about 30 carbons, more preferably 1 to 12 carbons. Examples of alkyl radicals include methyl, ethyl, n-propyl, isopropyl, n-butyl, isobutyl, sec-butyl, tert-butyl, tert-amyl, pentyl, hexyl, heptyl, octyl and the like. The term "cycloalkyl" embraces cyclic configurations, is subsumed within the definition of alkyl and specifically refers to a monocyclic, bicyclic, tricyclic, and higher multicyclic alkyl radicals wherein each cyclic moiety has from 3 to about 8 carbon atoms. Examples of cycloalkyl radicals include cyclopropyl, cyclobutyl, cyclopentyl, cyclohexyl and the like. A "lower alkyl" is a shorter alkyl, e.g., one containing from 1 about 6 carbon atoms.

The term "alkenyl," alone or in combination, refers to an optionally substituted straight-chain or optionally substituted branched-chain, alkenyl hydrocarbon radical having one or more carbon-carbon double-bonds and having from 2 to about 30 carbon atoms, more preferably 2 to about 18 carbons. Examples of alkenyl radicals include ethenyl, propenyl, butenyl, 1,4-butadienyl and the like. The term can also embrace cyclic alkenyl structures. A "lower alkenyl" refers to an alkenyl having from 2 to about 6 carbons.

The term "alkynyl," alone or in combination, refers to an optionally substituted straight-chain, or optionally substituted branched-chain, alkynyl hydrocarbon radical having one or more carbon-carbon triple-bonds and having from 2 to about 30 carbon atoms, more preferably 2 to about 12 carbon atoms. The term also includes optionally substituted straight-chain or optionally substituted branched-chain hydrocarbon radicals having one or more carbon-carbon triple bonds and having from 2 to about 6 carbon atoms as well as those having from 2 to about 4 carbon atoms. Examples of alkynyl radicals include ethynyl, propynyl, butynyl and the like.

The terms heteroalkyl, heteroalkenyl and heteroalkynyl include optionally substituted alkyl, alkenyl and alkynyl structures, as described above, and which have one or more skeletal chain atoms selected from an atom other than carbon, e.g., oxygen, nitrogen, sulfur, phosphorous or combinations thereof.

The term "carbon chain" may embrace any alkyl, alkenyl, alkynyl, or heteroalkyl, heteroalkenyl, or heteroalkynyl group, and may be linear, cyclic, or any combination thereof. If part of a linker and that linker comprises one or more rings as part of the core backbone, for purposes of calculating chain length, the "chain" only includes those carbon atoms that compose the bottom or top of a given ring and not both, and where the top and bottom of the ring(s) are not equivalent in length, the shorter distance shall be used in determining chain length. If the chain contains heteroatoms as part of the backbone, those atoms are not calculated as part of the carbon chain length.

The term "alkoxy," alone or in combination, refers to an alkyl ether radical, alkyl-O—, wherein the term alkyl is defined as above. Examples of alkoxy radicals include methoxy, ethoxy, n-propoxy, isopropoxy, n-butoxy, iso-butoxy, sec-butoxy, tert-butoxy and the like.

The term "aryloxy," alone or in combination, refers to an aryl ether radical wherein the term aryl is defined as below. Examples of aryloxy radicals include phenoxy, benzyloxy and the like.

The term "alkylthio," alone or in combination, refers to an alkyl thio radical, alkyl-S—, wherein the term alkyl is defined as above.

The term "arylthio," alone or in combination, refers to an aryl thio radical, aryl-S—, wherein the term aryl is defined as below.

The term "oxo" refers to =O.

The term "aryl," alone or in combination, refers to an optionally substituted aromatic ring system. The term aryl includes monocyclic aromatic rings, polyaromatic rings and polycyclic aromatic ring systems containing from six to about twenty carbon atoms. The term aryl also includes monocyclic aromatic rings, polyaromatic rings and polycyclic ring systems containing from 6 to about 12 carbon atoms, as well as those containing from 6 to about 10 carbon atoms. The polyaromatic and polycyclic aromatic rings systems may contain from two to four rings. Examples of aryl groups include, without limitation, phenyl, biphenyl, naphthyl and anthryl ring systems.

The term "heteroaryl" refers to optionally substituted aromatic ring systems containing from about five to about 20 skeletal ring atoms and having one or more heteroatoms such as, for example, oxygen, nitrogen, sulfur, and phosphorus. The term heteroaryl also includes optionally substituted aromatic ring systems having from 5 to about 12 skeletal ring atoms, as well as those having from 5 to about 10 skeletal ring atoms. The term heteroaryl may include five- or six-membered heterocyclic rings, polycyclic heteroaromatic ring systems and polyheteroaromatic ring systems where the ring system has two, three or four rings. The terms heterocyclic, polycyclic heteroaromatic and polyheteroaromatic include ring systems containing optionally substituted heteroaromatic rings having more than one heteroatom as described above (e.g., a six membered ring with two nitrogens), including polyheterocyclic ring systems of from two to four rings. The term heteroaryl includes ring systems such as, for example, furanyl, benzofuranyl, chromenyl, pyridyl, pyrrolyl, indolyl, quinolinyl, N-alkyl pyrrolyl, pyridyl-N-oxide, pyrimidoyl, pyrazinyl, imidazolyl, pyrazolyl, oxazolyl, benzothiophenyl, purinyl, indolizinyl, thienyl and the like.

The term "heteroarylalkyl" refers to a C1-C4 alkyl group containing a heteroaryl group, each of which may be optionally substituted.

The term "heteroarylthio" refers to the group —S-heteroaryl.

The term "acyloxy" refers to the ester group —OC(O)—R, where R is H, alkyl, alkenyl, alkynyl, aryl, or arylalkyl, wherein the alkyl, alkenyl, alkynyl and arylalkyl groups may be optionally substituted.

The term "carboxy esters" refers to —C(O)OR where R is alkyl, aryl or arylalkyl, wherein the alkyl, aryl and arylalkyl groups may be optionally substituted.

The term "carboxamido" refers to

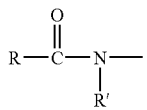

where each of R and R' are independently selected from the group consisting of H, alkyl, aryl and arylalkyl, wherein the alkyl, aryl and arylalkyl groups may be optionally substituted.

The term "arylalkyl," alone or in combination, refers to an alkyl radical as defined above in which one H atom is replaced by an aryl radical as defined above, such as, for example, benzyl, 2-phenylethyl and the like.

The term "alkylaryl," alone or in combination, refers to an aryl radical as defined above in which one H atom is replaced by an alkyl radical as defined above, such as, for example, tolyl, xylyl and the like.

The terms haloalkyl, haloalkenyl, haloalkynyl and haloalkoxy include alkyl, alkenyl, alkynyl and alkoxy structures, as described above, that are substituted with one or more fluorines, chlorines, bromines or iodines, or with combinations thereof.

The terms cycloalkyl, aryl, arylalkyl, heteroaryl, alkyl, alkynyl, alkenyl, haloalkyl and heteroalkyl include optionally substituted cycloalkyl, aryl, arylalkyl, heteroaryl, alkyl, alkynyl, alkenyl, haloalkyl and heteroalkyl groups.

The term "carbocycle" includes optionally substituted, saturated or unsaturated, three- to eight-membered cyclic structures in which all of the skeletal atoms are carbon.

The term "heterocycle" includes optionally substituted, saturated or unsaturated, three- to eight-membered cyclic structures in which one or more skeletal atoms is oxygen, nitrogen, sulfur, phosphorus or combinations thereof. Illustrative examples include pyridine, pyran, thiophane, pyrrole, furan, thiophene, pentatomic and hexatomic lactam rings, and the like.

The term "membered ring" can embrace any cyclic structure, including carbocycles and heterocycles as described above. The term "membered" is meant to denote the number of skeletal atoms, that constitute the ring. Thus, for example, pyridine, pyran, and thiophane are 6 membered rings and pyrrole, furan, and thiophene are 5 membered rings.

The term "acyl" includes alkyl, aryl, heteroaryl, arylalkyl or heteroarylalkyl substituents attached to a compound via a carbonyl functionality (e.g., —CO-alkyl, —CO-aryl, —CO-arylalkyl or —CO-heteroarylalkyl, etc.).

"Optionally substituted" groups may be substituted or unsubstituted. The substituents of an "optionally substituted" group may include, without limitation, one or more substituents independently selected from the following groups or designated subsets thereof: alkyl, alkenyl, alkynyl, heteroalkyl, haloalkyl, haloalkenyl, haloalkynyl, cycloalkyl, aryl, heteroaryl, arylalkyl, heteroarylalkyl, alkoxy, aryloxy, haloalkoxy, amino, alkylamino, dialkylamino, alkylthio, arylthio, heteroarylthio, oxo, carboxyesters, carboxamido, acyloxy, halogens, CN, $NO_2$, $NH_2$, $N_3$, $NHCH_3$, $N(CH_3)_2$, SH, $SCH_3$, OH, $OCH_3$, $OCF_3$, $CH_3$, $CF_3$, $C(O)CH_3$, $CO_2CH_3$, $CO_2H$, $C(O)NH_2$, pyridinyl, thiophene, furanyl, indole, indazol, esters, amides, phosphonates, phosphates, phosphoramides, sulfonates, sulfates, sulphonamides, carbamates, ureas, thioureas, thioamides, thioalkyls. An optionally substituted group may be unsubstituted (e.g., —$CH_2CH_3$), fully substituted (e.g., —$CF_2CF_3$), monosubstituted (e.g., —$CH_2CH_2F$) or substituted at a level anywhere in-between fully substituted and monosubstututed (e.g., —$CH_2CF_3$).

The term "halogen" includes F, Cl, Br and I.

The term sulfide refers to a sulfur atom covalently linked to two atoms; the formal oxidation state of said sulfur is (II). The term "thioether" may used interchangebly with the term "sulfide".

The term "sulfoxide" refers to a sulfur atom covalently linked to three atoms, at least one of which is an oxygen atom; the formal oxidation state of said sulfur atom is (IV).

The term "sulfone" refers to a sulfur atom covalently linked to four atoms, at least two of which are oxygen atoms; the formal oxidation state of said sulfur atom is (VI).

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well. Further, it is possible using well known techniques to separate the various forms, and some embodiments of the invention may feature purified or enriched species of a given enantiomer or diasteriomer.

A "pharmacological composition" refers to a mixture of one or more of the compounds described herein, or pharmaceutically acceptable salts thereof, with other chemical components, such as pharmaceutically acceptable carriers and/or excipients. The purpose of a pharmacological composition is to facilitate administration of a compound to an organism.

The phrase "pharmaceutically acceptable carrier" as used herein means a pharmaceutically-acceptable material, composition or vehicle, such as a liquid or solid filler, diluent, excipient, solvent or encapsulating material, involved in carrying or transporting the subject agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. A physiologically acceptable carrier should not cause significant irritation to an organism and does not abrogate the biological activity and properties of the administered compound.

An "excipient" refers to an inert substance added to a pharmacological composition to further facilitate administration of a compound. Examples of excipients include but are not limited to calcium carbonate, calcium phosphate, various sugars and types of starch, cellulose derivatives, gelatin, vegetable oils and polyethylene glycols.

A "pharmaceutically effective amount" means an amount which is capable of providing a therapeutic and/or prophylactic effect. The specific dose of compound administered according to this invention to obtain therapeutic and/or prophylactic effect will, of course, be determined by the particular circumstances surrounding the case, including, for example, the specific compound administered, the route of administration, the condition being treated, and the individual being treated. A typical daily dose (administered in single or divided doses) will contain a dosage level of from about 0.01 mg/kg to about 50-100 mg/kg of body weight of an active compound of the invention. Preferred daily doses generally will be from about 0.05 mg/kg to about 20 mg/kg and ideally from about 0.1 mg/kg to about 10 mg/kg. Factors such as clearance rate and half-life and maximum tolerated dose (MTD) have yet to be determined but one of ordinary skill in the art can determine these using standard procedures.

In some method embodiments, the preferred therapeutic effect is the inhibition, to some extent, of the growth of cells characteristic of a proliferative disorder, e.g., breast cancer. A therapeutic effect will also normally, but need not, relieve to some extent one or more of the symptoms other than cell growth or size of cell mass. A therapeutic effect may include, for example, one or more of 1) a reduction in the number of cells; 2) a reduction in cell size; 3) inhibition (i.e., slowing to some extent, preferably stopping) of cell infiltration into peripheral organs, e.g., in the instance of cancer metastasis; 3) inhibition (i.e., slowing to some extent, preferably stopping) of tumor metastasis; 4) inhibition, to some extent, of cell growth; and/or 5) relieving to some extent one or more of the symptoms associated with the disorder.

In some method embodiments of the invention, the "$IC_{50}$" value of a compound of the invention can be greater for normal cells than for cells exhibiting a proliferative disorder, e.g., breast cancer cells. The value depends on the assay used.

By a "standard" is meant a positive or negative control. A negative control in the context of HER-2 expression levels is, e.g., a sample possessing an amount of HER-2 protein that correlates with a normal cell. A negative control may also include a sample that contains no HER-2 protein. By contrast, a positive control does contain HER-2 protein, preferably of an amount that correlates with overexpression as found in proliferative disorders, e.g., breast cancers. The controls may be from cell or tissue samples, or else contain purified ligand (or absent ligand), immobilized or otherwise. In some embodiments, one or more of the controls may be in the form of a diagnostic "dipstick."

By "selectively targeting" is meant affecting one type of cell to a greater extent than another, e.g., in the case of cells with high as opposed to relatively low or normal Her-2 levels.

Synthesis of the Compounds of the Invention

The following synthesis scheme 1 is applicable to various of the compounds, compositions, methods, and formulations of the invention:

Scheme 1

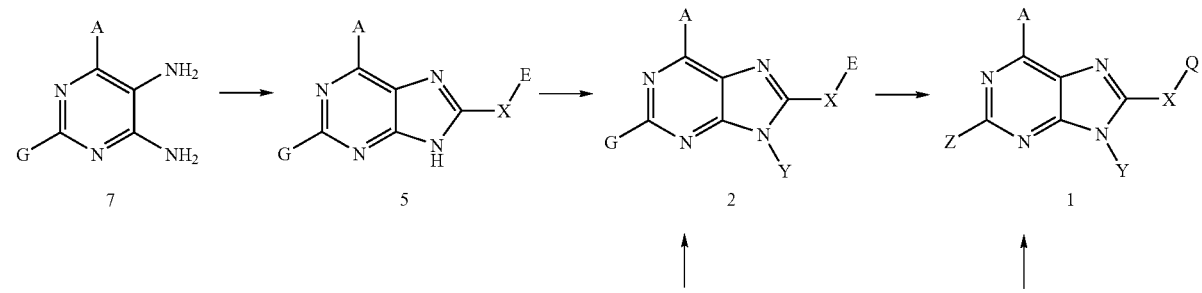

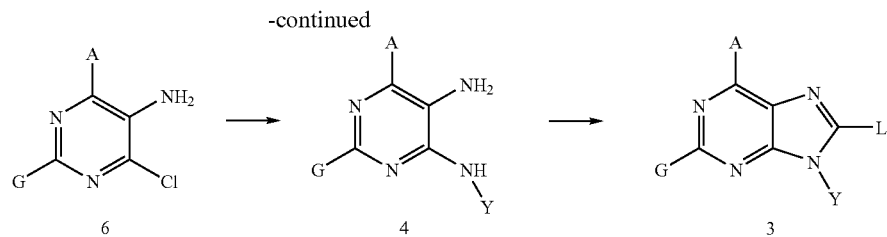

Synthesis of compounds of formula 1 (when X=C) in scheme 1 may include some or all of the following general steps. The 8-substituted purine analogs of formula 5 or 2 can be prepared from 4,5-diaminopyrimidines and the carboxylates or their derivatives, such as amides, esters, nitrites, orthoesters, imidates etc (see, e.g.,Townsend Chemistry of Nucleosides and Nucleotides, Vol. 1; Plenum Press, New York and London, page 148-158; Tetrahedron Lett. 36, 4249, 1995). Substituted 4,5-diaminopyrimidines can be obtained commercially or from substituted 2-chloro-3-amino pyrimidine or 2-chloro-3-nitropyrimidines as known in the art. See, e.g., Tetrahedron, 40, 1433 (1984); J. Am. Chem. Soc., 118, 135 (1975); Synthesis 135 (1975); J. Med. Chem. 39, 4099 (1996).

Compounds of formula 5 can be converted to compounds of formula 2 by simple alkylation with alkylhalides, alkyltosylates, mesolates or triflates in polar solvents like THF, DMF or DMSO using bases like NaH, $Cs_2CO_3$ or $K_2CO_3$, or by the well-known Mitsunobu alkylation method.

Compounds of formula 2 can be further modified to give compounds of formula 1 or the intermediates to prepare compounds of formula 1, e.g., substitution of 6-chloropurine by ammonia or alkylamines. C-2 substitution of purines, e.g., halogenation with F, Cl or Br can be introduced via 2-aminopurines as described by Eaton et al., J. Org. Chem. 34(3), 747-8 (1969) or by nucleophilic substitution as described, e.g., in. J. Med. Chem. 36, 2938 (1993) and Heterocycles, 30, 435, (1990). These C-2 substitutions also can be introduced via metalation as described, e.g., in J. Org. Chem. 62(20), 6833 (1997), followed by addition of desired electrophile. General purine substitution can be accomplished as described in J. Med. Chem. 42, 2064 (1999).

Alternatively, intermediates of formula 2 can be prepared from chloroaminopyrimidines such as formula 6 by the following two steps: (1) treatment of the compounds of formula 6 with corresponding amine (Y—NH2), e.g., butylamine, in presence of base such as triethyl amine or N,N-diisopropyl amine in polar solvents such as n-BuOH to give the substituted diamine compounds of formula 4; (2) treatment of the compounds of formula 4 using the same methods as described earlier going from formula 7 to formula 5. Similar methods as described earlier can be used to introduce the C-2 substitution (point at which Z or G moiety attaches).

Compounds of formula 1 where A is other than $NH_2$, e.g., halogen, methoxy, alkyl, or trifluoro alkyl, can be prepared starting with the corresponding substituent in place (if it can withstand the transformations), or, for halogen or substituted amines, these can be prepared from the 6-amine.

The compounds of formula 1 can also be prepared from formula 3, where L is halogen, using Negishi-type couplings (e.g., as described in J. Org. Chem. 2001, 66, 7522; J. Org. Chem. 1991, 56,1445).

Compounds of formula 1 wherein X is a heteroatom such as S, O or N can be prepared by the following scheme 2. In general, these compounds are linked via their C-8 to one of the heteroatoms X=S, O, or N and can be prepared from the corresponding 8-halo (e.g., bromo, iodo or chloro) compounds such as formula 10 using nucleophiles such as sulfides, alkyl or arylthiols, amines, azides, and alcohols.

Scheme 2

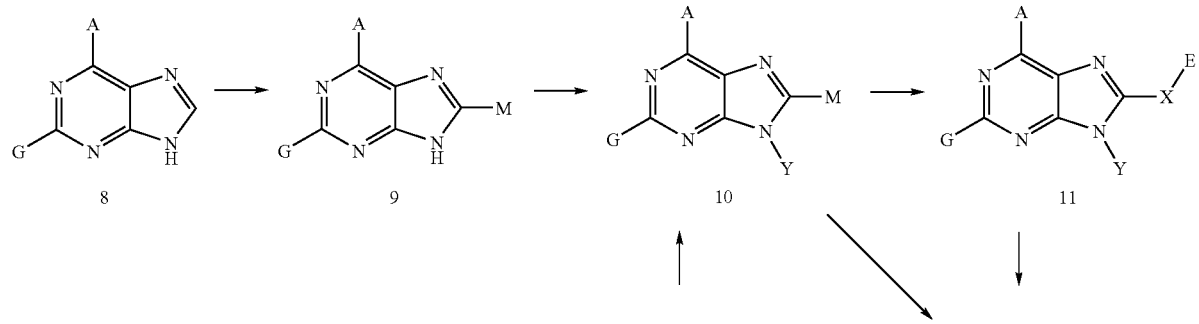

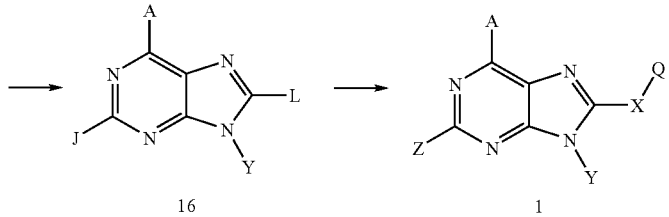

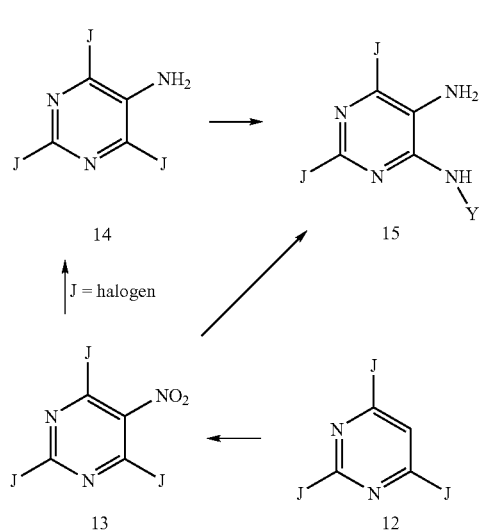

With reference to scheme 2, substituted adenines or purines of formula 8 can be treated with halogenating agents such as bromine or iodine, followed by alkylation at N-9 to give compounds of formula 10, wherein M is halogen such as bromine or iodine (Dang et. al. PCT, WO 98/39344). Compounds of formula 16 can be prepared from trihalopyrimidines such as those of formula 12 by nitration to give compounds of formula 13. Subsequent displacement of the halogen with amine (YNH$_2$) and reduction of the nitrogroup gives the diamines of formula 15. Alternatively, reduction of the nitrogroup may precede halogen displacement. Diamines of formula 15 can be readily cyclized to the imidazole ring of the compounds of formula 16, wherein L is H, SH, OH or NH$_2$ (Org. Syn. Collective Vol. 2, 65; Org. Syn. Collective Vol. 4, 569). The compounds of formula 1 can also be synthesized from the compounds of formula 16, wherein L is SH, OH, or NH$_2$, by reacting with aromatic halides, boronic acids, triflates, or their equivalents in presence of a catalyst such as palladium or copper Buchwald, S. L. et. al. J. Am. Chem. Soc., 1998, 120, 213-214; Buchwald, S. L. et. al. Acc. Chem. Res. 1998, 31, 805; Buchwald, S. L. et. al Org. Lett., 2002, 4, 3517-3520).

Alternately, compounds of formulae 1 and 11 (wherein X=S or O) can be synthesized by coupling of the diazonium salts of the compounds of formulae 10 or 16 (wherein M or L is N$_2$.BF$_4$, N$_2$.HCl, N$_2$.H$_2$SO$_4$ etc.) with HXE or HXQ (wherein X=S or O) in the presence of base such as t-BuOK, NaH, etc. in solvents such as DMF, MeOH, etc.

Z-groups of formula 1 can be introduced by modifying existing 2-substituents such as G. For example, 2-halopurines of formula 1 can be prepared from 2-aminopurines (G=NH$_2$) via chemistry well described in the literature. Other substitutions such as S-alkyl or aryl, O-alkyl can be made from nucleophilic substitution reactions; metal-catalysed reactions, etc. (see, e.g., Aerschot et. al., J. Med. Chem. 36:2938 (1993); Buchwald, S. L. et. al., Heterocycles, 30: 435 (1990).

The E component (aromatic or heteroaromatic or alkyl) of the compounds of formula 11 can be further modified as needed using well known procedures including, e.g., nucleophilic additions, electrophilic additions, halogenations, etc. to give Q (see, e.g., Advanced Organic Chemistry, March. J. Wiley Interscience).

Compounds of formula 1, wherein X is S(O) or S(O)$_2$ can be prepared by the oxidation of the compounds of formula 1, wherein X=S, using reagents such as MCPBA, H$_2$O$_2$, NaIO$_4$, Oxone, etc. in solvents such as CHCl$_3$, CH$_2$Cl$_2$ etc. Also, these sulfone compounds can be made by coupling of sulfonyl salts such as Li, Na, K (ArS(O)$_2$Li) and compounds of formulae 10 or 16 (wherein M or L is halogen such as Br or I) in polar solvents such as DMF. (Chem. Abstr. 1952, 4549). With controlled reduction of these sulfones, one can make compounds of formula 1 where X is S(O) and S(O)$_2$.

Pharmaceutical Compositions, Dosaging and Modes of Administration

Those of ordinary skill in the art are familiar with formulation and administration techniques that can be employed with the compounds and methods of the invention, e.g., as discussed in Goodman and Gilman's, *The Pharmacological Basis of Therapeutics*, current edition; Pergamon Press; and Remington's Pharmaceutical Sciences (current edition.) Mack Publishing Co., Easton, Pa.

The compounds utilized in the methods of the instant invention may be administered either alone or in combination with pharmaceutically acceptable carriers, excipients or diluents, in a pharmaceutical composition, according to standard pharmaceutical practice. The compounds can be administered orally or parenterally, including the intravenous, intramuscular, intraperitoneal, subcutaneous, rectal and topical routes of administration.

For example, the therapeutic or pharmaceutical compositions of the invention can be administered locally to the area in need of treatment. This may be achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. The administration can also be by direct injection at the site (or former site) of a tumor or neoplastic or pre-neoplastic tissue.

Still further, the compounds or compositions of the invention can be delivered in a vesicle, e.g., a liposome (see, for example, Langer, 1990, Science, 249:1527-1533; Treat et al., 1989, Liposomes in the Therapy of Infectious Disease and Cancer, Lopez-Bernstein and Fidler (eds.), Liss, N.Y., pp. 353-365).

The compounds and pharmaceutical compositions used in the methods of the present invention can also be delivered in a controlled release system. In one embodiment, a pump may be used (see, Sefton, 1987, CRC Crit. Ref. Biomed. Eng. 14:201; Buchwald et al., 1980, Surgery, 88:507; Saudek et al., 1989, N. Engl. J. Med., 321:574). Additionally, a controlled release system can be placed in proximity of the therapeutic target. (see, Goodson, 1984, Medical Applications of Controlled Release, Vol. 2, pp. 115-138).

The pharmaceutical compositions used in the methods of the instant invention can also contain the active ingredient in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions, and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, such as microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be un-coated or coated by known techniques to mask the taste of the drug or delay disintegration and absorption in the gastrointestinal tract and thereby provide a sustained action over a longer period. For example, a water soluble taste masking material such as hydroxypropylmethyl-cellulose or hydroxypropylcellulose, or a time delay material such as ethyl cellulose, or cellulose acetate butyrate may be employed as appropriate.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending a gent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The compounds and pharmaceutical compositions used in the methods of the instant invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening agents, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The Compounds of the present invention used in the methods of the present invention may also be administered in the form of suppositories for rectal administration of the drug. These compositions can be prepared by mixing the inhibitors with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing an compound or composition of the invention can be used. As used herein, topical application can include mouth washes and gargles.

The compounds used in the methods of the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The methods, compounds and compositions of the instant invention may also be used in conjunction with other well known therapeutic agents that are selected for their particular usefulness against the condition that is being treated. For example, the instant compounds may be useful in combination with known anti-cancer and cytotoxic agents. Further, the instant methods and compounds may also be useful in combination with other inhibitors of parts of the signaling pathway that links cell surface growth factor receptors to nuclear signals initiating cellular proliferation.

The methods of the present invention may also be useful with other agents that inhibit angiogenesis and thereby inhibit the growth and invasiveness of tumor cells, including, but not limited to VEGF receptor inhibitors, including ribozymes and antisense targeted to VEGF receptors, angiostatin and endostatin.

Examples of antineoplastic agents that can be used in combination with the compounds and methods of the present invention include, in general, and as appropriate, alkylating agents, anti-metabolites; epidophyllotoxin; an antineoplastic enzyme; a topoisomerase inhibitor; procarbazine; mitoxantrone; platinum coordination complexes; biological response modifiers and growth inhibitors; hormonal/anti-hormonal therapeutic agents and haematopoietic growth factors. Exemplary classes of antineoplastics include the anthracycline family of drugs, the vinca drugs, the mitomycins, the bleomycins, the cytotoxic nucleosides, the epothilones, discodermolide, the pteridine family of drugs, diynenes and the podophyllotoxins. Particularly useful members of those classes include, for example, carminomycin, daunorubicin, aminopterin, methotrexate, methopterin, dichloromethotrexate, mitomycin C, porfiromycin, 5-fluorouracil, 6-mercaptopurine, gemcitabine, cytosine arabinoside, podophyllotoxin or podo-phyllotoxin derivatives such as etoposide, etoposide phosphate or teniposide, melphalan, vinblastine, vincristine, leurosidine, vindesine, leurosine, paclitaxel and the like. Other useful antineoplastic-agents include estramustine, carboplatin, cyclophosphamide, bleomycin, gemcitibine, ifosamide, melphalan, hexamethyl melamine, thiotepa, cytarabin, idatrexate, trimetrexate, dacarbazine, L-asparaginase, camptothecin, CPT-11, topotecan, ara-C, bicalutamide, flutamide, leuprolide, pyridobenzoindole derivatives, interferons and interleukins.

When a compound or composition of the invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for cancer, for example, breast cancer. Administration typically occurs in an amount of between about 0.01 mg/kg of body weight to about 100 mg/kg of body weight per day (administered in single or divided doses), more preferably at least about 0.1 mg/kg of body weight per day. A particular therapeutic dosage can include, e.g., from about 0.01 mg to about 1000 mg of compound, and preferably includes, e.g., from about 1 mg to about 1000 mg. The quantity of active compound in a unit dose of preparation may be varied or adjusted from about 0.1 mg to 1000 mg, preferably from about 1 mg to 300 mg, more preferably 10 mg to 200 mg, according to the particular application. The amount administered will vary depending on the particular IC50 value of the compound used and the judgment of the attending clinician taking into consideration factors such as health, weight, and age. In combinational applications in which the compound is not the sole active ingredient, it may be possible to administer lesser amounts of compound and still have therapeutic or prophylactic effect.

Preferably, the pharmaceutical preparation is in unit dosage form. In such form, the preparation is subdivided into unit doses containing appropriate quantities of the active component, e.g., an effective amount to achieve the desired purpose.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

The amount and frequency of administration of the compounds and compositions of the present invention used in the methods of the present invention, and if applicable other chemotherapeutic agents and/or radiation therapy, will be regulated according to the judgment of the attending clinician (physician) considering such factors as age, condition and size of the patient as well as severity of the disease being treated.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

Also, in general, the compounds of the invention need not be administered in the same pharmaceutical composition as a chemotherapeutic agent, and may, because of different physical and chemical characteristics, be administered by a different route. For example, the compounds/compositions may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The particular choice of compound (and where appropriate, chemotherapeutic agent and/or radiation) will depend upon the diagnosis of the attending physicians and their judgment of the condition of the patient and the appropriate treatment protocol.

The compounds/compositions of the invention (and where appropriate chemotherapeutic agent and/or radiation) may be administered concurrently (e.g., simultaneously, essentially simultaneously or within the same treatment protocol) or sequentially, depending upon the nature of the proliferative disease, the condition of the patient, and the actual choice of chemotherapeutic agent and/or radiation to be administered in conjunction (i.e., within a single treatment protocol) with the compound/composition.

In combinational applications and uses, the compound/composition and the chemotherapeutic agent and/or radiation are not administered simultaneously or essentially simultaneously, then the initial order of administration of the compound/composition, and the chemotherapeutic agent and/or radiation, may not be important. Thus, the compounds/compositions of the invention may be administered first followed by the administration of the chemotherapeutic agent and/or radiation; or the chemotherapeutic agent and/or radiation may be administered first followed by the administration of the compounds/compositions of the invention. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent and/or radiation may be administered first, especially if it is a cytotoxic agent, and then the treatment continued with the administration of the compounds/compositions of the invention followed, where determined advantageous, by the administration of the chemotherapeutic agent and/or radiation, and so on until the treatment protocol is complete.

Thus, in accordance with experience and knowledge, the practicing physician can modify each protocol for the administration of a compound/composition for treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

Assays to Determine HSP90 Binding and Downstream Effect

A variety of in vitro and in vivo assays are available to test the effect of the compounds of the invention on HSP90. HSP90 competitive binding assays and functional assays can be performed as known in the art substituting in the compounds of the invention. Chiosis et al., Chemistry & Biology 8:289-299 (2001), describe some of the known ways in which this can be done. For example, competition binding assays using, e.g., geldanamycin or 17-AAG as a competitive binding inhibitor of HSP90 can be used to determine relative HSP90 affinity of the compounds of the invention by immobilizing the compound of interest or other competitive inhibitor on a gel or solid matrix, preincubating HSP90 with the other inhibitor, passing the preincubated mix over the gel or matrix, and then measuring the amount of HSP90 that sticks or does not stick to the gel or matrix.

Downstream effects can also be evaluated based on the known effect of HSP90 inhibition on function and stability of various steroid receptors and signaling proteins including, .e.g., Raf1 and Her2. Compounds of the present invention induce dose-dependent degradation of these molecules, which can be measured using standard techniques. Inhibition of HSP90 also results in up-regulation of HSP90 and related chaperone proteins that can similarly be measured. Antiproliferative activity on various cancer cell lines can also be measured, as can morphological and functional differentiation related to HSP90 inhibition.

Many different types of methods are known in the art for determining protein concentrations and measuring or predicting the level of proteins within cells and in fluid samples. Indirect techniques include nucleic acid hybridization and amplification using, e.g., polymerase chain reaction (PCR). These techniques are known to the person of skill and are discussed, e.g., in Sambrook, Fritsch & Maniatis, Molecular Cloning: A Laboratory Manual, Second Edition (1989) Cold Spring Harbor Laboratory Press, Cold Spring Harbor, N.Y., Ausubel, et al., Current Protocols in Molecular Biology, John Wiley & Sons, NY, 1994, and, as specifically applied to the quantification, detection, and relative activity of Her-2/neu in patient samples, e.g., in U.S. Pat. Nos. 4,699,877, 4,918,162, 4,968,603, and 5,846,749. A brief discussion of two generic techniques that can be used follows.

The determination of whether cells overexpress or contain elevated levels of HER-2 can be determined using well known antibody techniques such as immunoblotting, radio-immunoassays, western blotting, immunoprecipitation, enzyme-linked immunosorbant assays (ELISA), and derivative techniques that make use of antibodies directed against HER-2. As an example, HER-2 expression in breast cancer cells can be determined with the use of an immunohistochemical assay, such as the Dako Hercep™ test (Dako Corp., Carpinteria, Calif.). The Hercep™ test is an antibody staining assay designed to detect HER-2 overexpression in tumor tissue specimens. This particular assay grades HER-2 expression into four levels: 0, 1, 2, and 3, with level 3 representing the highest level of HER-2 expression. Accurate quantitation can be enhanced by employing an Automated Cellular Imaging System (ACIS) as described, e.g., by Press, M, et al, (2000), Modern Pathology 13:225A.

Antibodies, polyclonal or monoclonal, can be purchased from a variety of commercial suppliers, or may be manufactured using well-known methods, e.g., as described in Harlow et al., Antibodies: A Laboratory Manual, 2nd Ed; Cold Spring Harbor Laboratory Press, Cold Spring Harbor, N.Y. (1988).

HER-2 overexpression can also be determined at the nucleic acid level since there is a reported high correlation between overexpression of the HER-2 protein and amplification of the gene that codes for it. One way to test this is by using RT-PCR. The genomic and cDNA sequences for HER-2 are known. Specific DNA primers can be generated using standard, well-known techniques, and can then be used to amplify template already present in the cell. An example of this is described in Kurokawa, H et al, Cancer Res. 60: 5887-5894 (2000). PCR can be standardized such that quantitative differences are observed as between normal and abnormal cells, e.g., cancerous and noncancerous cells. Well Known methods employing, e.g. densitometry, can be used to quantitate and/or compare nucleic acid levels amplified using PCR.

Similarly, fluorescent in situ hybridization (FISH) assays and other assays can be used, e.g., Northern and/or Southern blotting. These rely on nucleic acid hybridization between the HER-2 gene or MRNA and a corresponding nucleic acid probe that can be designed in the same or a similar way as for PCR primers, above. See, e.g., Mitchell MS, and Press MF., 1999, Semin. Oncol., Suppl. 12:108-16. For FISH, this nucleic acid probe can be conjugated to a fluorescent molecule, e.g., fluorescein and/or rhodamine, that preferably does not interfere with hybridization, and which fluorescence can later be measured following hybridization. See, e.g., Kurokawa, H et al, Cancer Res. 60: 5887-5894 (2000) (describing a specific nucleic acid probe having sequence 5'-FAM-NucleicAcid-TAMRA-p-3' sequence). ACIS-based approaches as described above can be employed to make the assay more quantitative (de la Torre-Bueno, J, et al, 2000, Modern Pathology 13:221A).

Immuno and nucleic acid detection can also be directed against proteins other than HSP90 and Her-2, which proteins are nevertheless affected in response to HSP90 inhibition.

The following examples are offered by way of illustration only and are not intended to be limiting of the full scope and spirit of the invention.

EXAMPLES

The chemical reagents used below are all available commercially, e.g., from Aldrich Chemical Co., Milwaukee, Wis., USA, and/or their facile preparation known to one of ordinary skill in the art, or otherwise described or referenced herein.

Carbon Linker Compounds:

Example 1

Synthesis of 8-(2,5-dimethoxybenzyl)-N9-butyladenine

Step 1. A solution of 5-amino-4,6-dichloropyrimidine (1 mmol) in n-BuOH was treated with $Et_3N$ (1.2 mmol) and n-Butylamine (1.0 mmol) at 80 C. After 16 h, solvent was removed under reduced pressure. The residue was dissolved in EtOAc, the organic layer washed with water and then dried ($MgSO_4$). Filtration and removal of solvent gave 6-chloro-5-amino-4-butyl pyrimidine as a brown solid. $R_f$=0.5 in 1:1 EtOAc:hexane. $^1H$ NMR ($CDCl_3$) δ 8.07 (s, 1H), 4.88 (br s, 1H), 3.49 (m, 2H), 3.35 (br s, 2H), 1.6 (m, 2H), 1.44 (m, 2), 0.95 (t, 3H).

Step 2: To a solution of 2,5-dimethoxyphenylacetic acid (1 mmol) and $Et_3N$ (1 mmol) in $CH_2Cl_2$ was added p-toluenesulfonyl chloride (1 mmol) at rt. After 1 h, the mixture was treated with a solution of the product of step 1, 6-chloro-5-amino-4-butyl pyrimidine (1 mmol in $CH_2Cl_2$), followed by addition of $Et_3N$ (2 mmol). The resultant mixture was refluxed for 20 h. Solvent was removed and the residue dissolved into EtOAc, the organic layer washed with water and dried. The crude compound was taken into acetone, and precipitated product filtered out and washed with a small amount of acetone to give N-(4-butylamino-6-chloro-pyrimidin-5-yl)-2-(2,5-dimethoxyphenyl) acetamide. $R_f$=0.45 in 1:1 EtOAc:hexane. $^1H$ NMR (DMSO-$d_6$) δ 9.37 (s, 1H), 8.17 (s, 1H), 7.11 (t, 1H), 6.9 (d, 1H), 6.88 (d, 1H), 6.78 (dd, 1H), 3.73 (s, 3H), 3.69 (s, 3H), 3.63 (s, 3H), 3.35 (m, 2H), 1.48 (m, 2H), 1.29 (m, 2H), 0.88 (t, 3H).

Step 3: A mixture of N-(4-butylamino-6-chloro-pyrimidin-5-yl)-2-(2,5-dimethoxyphenyl) acetamide (1 mmol) and p-TSA (0.5 mmol) in toluene was refluxed for 72 h. Solvent was removed, diluted with EtOAc and washed with water, bicarbonate and dried. Purification on a silica gel column (200-400 mesh, Fisher Scientific, Tustin, Calif., USA) gave 6-chloro-8-(2,5-dimethoxybenzyl)-N9-butyl purine. $R_f$=0.65 in 1:1 EtOAc:hexane. $^1H$ NMR (DMSO-$d_6$) δ 8.7 (s, 1H), 6.96 (d, 1H), 6.84 (m, 1H), 6.8 (dd, 1H), 4.28 (s, 2H), 4.23 (t, 2H), 3.69 (s, 3H), 3.67 (s, 3H), 1.62 (m, 2H), 1.25 (m, 2H), 0.88 (t, 3H).

Step 4: To a solution of 6-chloro-8-(2,5-dimethoxybenzyl)-N9-butyl purine (1 mmol) in dioxane was added 28% $NH_4OH$ (50 mmol) and the mixture was then heated at 100 C in a seal tube for 48 h. Solvent was removed by azeotrope distillation with toluene. Purification on a silica gel column (see above) gave pure 8-(2,5-dimethoxybenzyl)-9-butyl adenine, 1.1. $R_f$=0.35 in 5% MeOH in EtOHAc. $^1H$ NMR (DMSO-$d_6$) δ 8.08 (s, 1H), 7.04 (br s, 2H), 6.94 (d, 1H), 6.80 (dd, 1H), 6.66 (d, 1H), 4.14 (s, 2H), 4.04 (t, 2H), 3.72 (s, 3H), 3.63 (s, 3H), 1.52 (m, 2H), 1.22 (m, 2H), 0.82 (t, 3H).

Alternatively, 8-(2,5-dimethoxybenzyl)-9-butyl adenine can also be prepared from N-(4-butylamino-6-chloro-pyrimidin-5-yl)-2-(2,5-dimethoxyphenyl) acetamide according to the following procedure: A solution of N-(4-butylamino-6-chloro-pyrimidin-5-yl)-2-(2,5-dimethoxyphenyl) acetamide (1 mmol) is taken into 7M $NH_3$ in MeOH (70 mmol) and the mixture heated at 120 C in a steel bomb for 72 h. Solvent is removed by azeotrope distillation with toluene. Purification on the silica gel column gave pure 8-(2,5-dimethoxybenzyl)-9-butyl adenine.

Example 2

Synthesis of 8-(2,5-dimethoxybenzyl)-N9-pentynyl-2-fluoro adenine

Step 1: 2-(2,5-Dimethoxy-phenyl)-N-(2,5,6-triamino-pyrimidin-4-yl)-acetamide, HCl A solution of 2,4,5,6-tetraaminopyrimidine (52.8 g, 378 mmol) in NMP (750 ml) was treated at 70° C. with 2,5-dimethoxyphenyl acetyl chloride (90 g, 419 mmol). After cooling to r.t., the precipitate was collected by filtration and washed with EtOAc to give the title compounds as a pale yellow powder (127 g, 95%). 1H NMR (DMSO-d₆) δ 9.12 (s, 1H), 7.80-7.40 (m, 3H), 6.22 (s, 2H), 6.04 (s, 4H), 4.41 (s, 3H), 4.29 (s, 3H), 4.25 (s, 2H); MS 319 (M+1).

Step 2: 8-(2,5-Dimethoxy-benzyl)-9H-purine-2,6-diamine

Sodium metal (2.3 g, 100 mmol) was dissolved in n-BuOH (50 ml) at 70° C. To this was added the acetamide of step 1, above (5.0 g, 14.1 mmol), and the mixture was heated to reflux for 1.5 h. Neutralization with 6N HCl to pH 8-9, extraction with EtOAc, drying, and evaporation gave the title compound as a pale yellow powder (3.2 g, 76%). $R_f$=0.45 in 1:3 MeOH:EtOAc. 1H NMR (DMSO-d₆) δ 12.3-11.7 (br. s, 1H), 6.92 (d, J=10.0 Hz, 1H), 6.82 (dd, J=10.0 & 3.0 Hz, 1H), 6.73 (s, 1H), 6.70-6.50 (br. s, 2H), 5.85-5.70 (br. s, 2H), 3.95 (s, 2H), 3.74 (s, 3H), 3.67 (s, 3H); MS 301 (M+1).

Step 3: 8-(2,5-Dimethoxy-benzyl)-9-pent-4-ynyl-9H-purine-2,6-diamine

A mixture of the purine 8-(2,5-Dimethoxy-benzyl)-9H-purine-2,6-diamine (19.0 g, 63 mmol), 5-chloro-pent-1-yne (12.3 ml, 116 mmol), and Cs₂CO₃ (37.8 g, 116 mmol) in DMF (180 g) was heated to 50° C. for 16 h. Filtration and washing (2×200 ml H₂O) afforded some desired product (5.8 g, 25%). The mother liquor was concentrated, diluted with EtOAc, and heated to reflux for 1 h to yield additional product (6.0 g, 26%). After cooling to room temperature, addition of 1 volume hexane to the EtOAc mother liquor gave additional product (2.6 g, 11%). Final work-up (CH₂Cl₂:MeOH 4:1—water) yielded additional product (5.3 g, containing 1 equivalent penty-4-yn-1-ol, 18%). $R_f$=0.65 in 1:10 MeOH:EtOAc. 1H NMR (DMSO-d₆) δ 6.92 (d, J=8.9 Hz, 1H), 6.98 (dd, J=8.9 & 3.0 Hz, 1H), 6.59 (s, J=2.9 Hz, 1H), 6.58-6.53 (br. s, 2H), 5.72-5.68 (br. s, 2H), 4.02 (s, 2H), 3.92 (t, J=7.4 Hz, 2H), 3.73 (s, 3H), 3.62 (s, 3H), 2.84 (t, J=2.5 Hz, 1H), 2.13 (td, J=7.0 & 1.7 Hz, 2H), 1.74 (quint., J=7.3 Hz, 2H); MS 367 (M+1).

Step 4: 8-(2,5-Dimethoxy-benzyl)-2-fluoro-9-pent-4-ynyl-9H-purin-6-ylamine

A solution of the above purine-2,6-diamine (11.8 g, 32.2 mmol) in 48% aq. HBF₄ (250 ml) was treated at −10° C. with iso-amyl nitrite (5.20 ml, 38.8 mmol), and warmed to r.t over 2.5 h. The reaction mixture was diluted with MeOH (400 ml) and CH₂Cl₂ (1500 ml), and carefully neutralized with a solution of K₂CO₃ (125 g) in water (500 ml). Caution: vigorous gas evolution. The aqueous layer was re-extracted with MeOH:CH₂Cl₂ (500 ml, 1:5). Concentration of the organic phase and two flash chromatography purifications (CH₂Cl₂:EtOAc:hexane:MeOH:Et₃N 1500:750:750:50:10→1500:750:750:150:10) yielded 8-(2, 5-Dimethoxy-benzyl)-2-fluoro-9-pent-4-ynyl-9H-purin-6-ylamine (4.5 g, 38%), 2.1 as a colorless powder. $R_f$=0.45 in 1:1 EtOAc:hexane. ¹H NMR (DMSO-d₆) δ 6.82 (d, J=8.9 Hz, 1H), 6.75 (dd, J=8.9 & 3.0 Hz, 1H), 6.68 (d, J=2.9 Hz, 1H), 6.25-6.10 (br. s, 2H), 4.20 (s, 2H), 4.13 (t, J=7.4 Hz, 2H), 3.79 (s, 3H), 3.70 (s, 3H), 2.16 (td, J=7.0 & 2.6 Hz, 2H), 1.97 (t, J=2.6 Hz, 1H), 1.95 (quint., J=7.3 Hz, 2H); MS 370 (M+1).

The following compounds, 2.2-2.4, were prepared using essentially the same procedures described for Example 2, except that in step 3 the electrophiles 1-bromo-4-methyl-pent-3-ene, 1-chloro-pent-4-ene, and 1,5-bromopentane were used in place of 5-chloro-pent-1-yne:

2.2  8-(2,5-Dimethoxy-benzyl)-2-fluoro-9-(4-methyl-pent-3-enyl)-9H-purin-6-ylamine isolated as solid, retention time=7.70.

2.3  8-(2,5-Dimethoxy-benzyl)-2-fluoro-9-pent-4-enyl-9H-purin-6-ylamine isolated as solid, retention time=7.61.

2.4  8-(2,5-Dimethoxy-benzyl)-2-fluoro-9-(5-bromo-pentyl)-9H-purin-6-ylamine isolated as solid, retention time=7.86.

Similarly, 2-Cl compound was prepared analogously to the method described in Step 4 using HCl and CuCl in place of HBF₄.

2.5  8-(2,5-Dimethoxy-benzyl)-2-chloro-9-pent-4-ynyl-9H-purin-6-ylamine; Rt=8.02 ¹H NMR (CDCl3) d 6.83 (d, J=8.9 Hz, 1H), 6.77 (dd, J=8.9 & 3.0 Hz, 1H), 6.68 (d, J=3.0 Hz, 1H), 6.18-6.00 (s, 2H), 4.20 (s, 2H), 4.18 (t, J=7.4 Hz, 2H), 3.78 (s, 3H), 4.93 (s, 3H), 2.20 (td, J=7.0 & 2.4 Hz, 2H), 2.63 (t, 2.4 Hz, 1H), 1.97 (quint., J=7.3 Hz, 2H).

HPLC method: Agilent Zorbax 300 SB C18, 4.6×150 mm, 5 μm; Column Temperature: Ambient; Flow Rate: 1.0 ml/min, Gradient: 10% acetonitrile (0.05% TFA) in water (0.1% TFA) to 100% acetonitrile (0.05% TFA) in 10 minutes, hold at 100% for 1 minutes); Retention times are measured in minutes.

Example 3

The above procedures can similarly be applied to produce compounds wherein Z is H by starting with 4,5,6, triaminopyrimidine sulfate and using electrophiles as shown in Table 3:

TABLE 3

| Ex. # | Electrophile | Final Compound/Structure/Name/ HPLC RT (min.)/CF# |
|---|---|---|
| 3.1 | 1-bromo-4-chlorobutane | 9-(4-Chloro-butyl)-8-(2,5-dimethoxy-benzyl)-9H-purin-6-ylamine isolated as solid; rt = 6.34. |
| 3.2 | 1-chloro-pent-4-yne | 8-(2,5-Dimethoxy-benzyl)-9-pent-4-ynyl-9H-purin-6-ylamine isolated as solid rt = 5.88 min. |
| 3.3 | 1-chloro-3-[1,3]dioxolan-2-yl]propane | 8-(2,5-Dimethoxy-benzyl)-9-(2-[1,3]dioxolan-2-yl-ethyl)-9H-purin-6-ylamine isolated as solid, rt = 5.36. |
| 3.4 | 1-bromo-4-methyl-pent-3-ene | 8-(2,5-Dimethoxy-benzyl)-9-(4-methyl-pent-3-enyl)-9H-purin-6-ylamine isolated as solid., rt = 6.60. |
| 3.5 | 1,5-dibromopentane | 9-(5-Bromo-pentyl)-8-(2,5-dimethoxy-benzyl)-9H-purin-6-ylamine isolated as solid, rt = 6.94. |
| 3.6 | 1,5-dibromo-3-methylpentane | 9-(5-Bromo-3-methyl-pentyl)-8-(2,5-dimethoxy-benzyl)-9H-purin-6-ylamine isolated as solid, rt = 7.32. |
| 3.7 | 1-bromo-5-Chloropentane | 9-(5-Chloro-pentyl)-8-(2,5-dimethoxy-benzyl)-9H-purin-6-ylamine isolated as solid, rt = 6.34. |
| 3.8 | 1-bromo-4-chlorobutane alkylation followed by treatment with ethylamine gave 4-ethylaminobutyl | 8-(2,5-Dimethoxy-benzyl)-9-(4-ethylamino-butyl)-9H-purin-6-ylamine isolated as solid, rt = 3.9. |
| 3.9 | 1-bromohexan-6-ol | 6-[6-Amino-8-(2,5-dimethoxy-benzyl)-purin-9-yl]-hexan-1-ol isolated as solid. |
| 3.10 | 2-(dimethyl-bicyclo[3.1.1]hept-2-en-2-yl)-3-bromopropane | 8-(2,5-Dimethoxy-benzyl)-9-[2-(dimethyl-bicyclo[3.1.1]hept-2-en-2-yl)-ethyl]-9H-purin-6-ylamine isolated as solid. |
| 3.11 | 1-bromo-5acetyloxypentane | Acetic acid 5-[6-amino-8-(2,5-dimethoxy-benzyl)-purin-9-yl]-pentyl ester isolated as solid; rt = 6.06. |
| 3.12 | 1-bromo-3,3,3-trifluoropropane | 8-(2,5-Dimethoxy-benzyl)-9-(3,3,3-trifluoro-propyl)-9H-purin-6-ylamine isolated as solid; |

TABLE 3-continued

| Ex. # | Electrophile | Final Compound/Structure/Name/ HPLC RT (min.)/CF# |
|---|---|---|
| 3.13 | 1-chloro-pent-4-yne | 8-(2,5-Dimethoxy-benzyl)-9-pent-4-ynyl-9H-purin-6-ylamine isolated as solid; rt = 5.88. |

Example 4

Halogenation of Benzene Ring 4.1 To a solution of 9-butyl-8-(3-methoxy-benzyl)-9H-purin-6-ylamine (1.24 g, 4 mmol) in AcOH (6 ml) was added N-iodo-succinamide (NIS) (1.8 g, 8 mmol). After 3 h at r.t., additional NIS (1.8 g, 8 mmol) was added, and the mixture was stirred for another 24 h. The reaction mixture was diluted with $CH_2Cl_2$ (500 ml), and carefully neutralized with a solution of sat. aq. $K_2CO_3$ (2×100 ml), then washed with 0.1 N $Na_2S_2O_3$ (3×100 ml), brine (3×100 ml), dried ($Na_2SO_4$), evaporated, and purified by flash chromatography ($CH_2Cl_2$:MeOH=100:5) to give the 9-Butyl-8-(2-iodo-5-methoxy-benzyl)-9H-purin-6-ylamine (4.1), as a colorless powder (0.53 g, 30%); rt=7.7 min.; 1HNMR (CDCl3-d) δ 8.36 (s, 1H), 7.77 (d, J=7.9 Hz, 1H), 6.68 (s, 1H), 6.61 (d, J=7.9 Hz, 1H), 5.62 (s, 2H), 4.33 (s, 2H), 4.06 (t, J=7.7 Hz, 2H), 3.72 (s, 3H), 1.67 (quint., J=7.7 Hz, 2H), 1.36 (sext., J=7.5 Hz, 2H), 0.92 (t, J=7.4 Hz, 3H).

Bromo and chloro derivatives were made using the same procedure, substituting NBS and NCS for NIS as appropriate. The following compounds were also synthesized according to essentially the same procedure, using as appropriate NIS, NCS or NBS:

4.2 9-Butyl-8-(5-iodo-2-methoxy-benzyl)-9H-purin-6-ylamine was made from 9-Butyl-8-(2-methoxy-benzyl)-9H-purin-6-ylamine as starting material in 48% yield $^1$H NMR (CDCl$_3$) δ 8.32 (s, 1H), 7.55 (dd, J=8.7, 2.2 Hz, 1H), 7.37 (d, J=2.2 Hz, 1H), 6.68 (d, J=8.7 Hz, 1H), 6.05-5.85 (br. s, 2H), 4.17 (s, 2H), 4.07 (t, J=7.6 Hz, 2H), 3.82 (s, 3H), 1.62 (quint., J=7.5 Hz, 2H), 1.30 (sext., J=7.5 Hz, 2H),0.89 (t, J=7.4 Hz, 3H).

4.3 9-Butyl-8-(5-ethyl-2-methoxy-benzyl)-9H-purin-6-ylamine; Rt=7.59; $^1$HNMR (CDCl3-d) δ 8.35 (s, 1H), 7.34 (d, J=8.8 Hz, 1H), 6.79 (dd, J=8.7, 2.8 Hz, 1H), 6.69 (d, J=2.7 Hz, 1H), 5,64 (s, 2H), 4.36 (s, 2H), 4.07 (t, J=7.7 Hz, 2H), 3.73 (s, 3H), 1.64 (quint., J=7.7 Hz, 2H), 1.32 (sext., J=7.5 Hz, 2H), 0.90 (t, J=7.4 Hz, 3H).

4.4 8-(2-Bromo-5-methoxy-benzyl)-9-butyl-9H-purin-6-ylamine; Rt=7.66; $^1$HNMR (CDCl3-d) δ 8.36 (s, 1H), 7.52 (d, J=8.7 Hz, 1H), 6.74 (dd, J=8.7, 3.0 Hz, 1H), 6.89 (d, J=3.0 Hz, 1H), 5,64 (s, 2H), 4.36 (s, 2H), 4.07 (t, J=7.7 Hz, 2H), 3.72 (s, 3H), 1.64 (quint., J=7.6 Hz, 2H), 1.34 (sext., J=7.5 Hz, 2H), 0.90 (t, J=7.4 Hz, 3H).

9-Butyl-8-(2-methoxy-benzyl)-9H-purin-6-ylamine and 9-butyl-8-(3-methoxy-benzyl)-9H-purin-6-ylamine were prepared from 4,5,6-triaminopyrimidine sulfate and, respectively 2-methoxyphenyl acetyl chloride or 3-methoxyphenyl acetic acid, by procedures analogous to the one described above. 2-Fluoro purine analogs were also prepared from 2,4,5,6-tetraaminopyrimidine, by procedures analogous to those described above. See Example 2, step 4.

For the following compounds, in which the N9 substituent (Y) is sensitive to halogenation, addition of the N9 substituent (Y) was done as a final step:

4.5 8-(2-Bromo-5-methoxy-benzyl)-9-(4-methyl-pent-3-enyl)-9H-purin-6-ylamine; Rt=8.22; $^1$HNMR (CDCl3-d) δ 8.37 (s, 1H), 7.51 (d, J=8.7 Hz, 1H), 6.73 (dd, J=8.7, 3.0 Hz, 1H), 6.65 (d, J=3.0 Hz, 1H), 5.53 (s, 2H), 5.12 (t, J=7.1 Hz, 2H), 4.35 (s, 2H), 4.07 (t, J=7.1 Hz, 2H), 3.72 (s, 3H), 2.43 (quart., J=7.1 Hz, 2H), 1.65 (s, 3H), 1.40 (s, 3H).

4.6 8-(2-Bromo-5-methoxy-benzyl)-9-pent-4-ynyl-9H-purin-6-ylamine; Rt=8.17; $^1$HNMR (CDCl3-d) δ 8.35 (s, 1H), 7.52 (d, J=8.8 Hz, 1H), 6.74 (dd, J=8.8, 2.9 Hz, 1H), 6.66 (d, J=2.9 Hz, 1H), 5.61 (s, 2H), 4.39 (s, 2H), 4.21 (t, J=7.4 Hz, 2H), 3.73 (s, 3H), 2.24 (td, J=6.8, 2.5 Hz, 2H), 2.03 (t, J=2.5 Hz, 1H), 1.99 (quint., J=7.2 Hz, 2H).

4.7 8-(2-Iodo-5-methoxy-benzyl)-9-pent-4-ynyl-9H-purin-6-ylamine; Rt=7.35; $^1$HNMR (CDCl3-d) δ 8.36 (s, 1H), 7.77 (d, J=8.5 Hz, 1H), 6.64-6.60 (m, 2H), 5.56 (s, 2H), 4.35 (s, 2H), 4.20 (t, J=7.4 Hz, 2H), 3.73 (s, 3H), 2.26 (td, J=6.9 Hz, 2.7 Hz, 2H), 2.03 (t, J=2.7 Hz, 1H), 2.02 (quint., J=7.0 Hz, 2H).

4.8 8-(2-Iodo-5-methoxy-benzyl)-9-(4-methyl-pent-3-enyl)-9H-purin-6-ylamine; Rt=8.17; $^1$HNMR (CDCl3-d) δ 8.58 (s, 1H), 8.33 (d, J=8.6 Hz, 1H), 6.60 (d, J=2.9 Hz, 1H), 6.57 (dd, J=8.6, 2.9 Hz, 1H), 6.15 (s, 2H), 5.12 (t, J=7.4 Hz, 2H), 4.29 (s, 2H), 4.04 (t, J=7.3 Hz, 2H), 3.67 (s, 3H), 2.42 (quart., J=7.2 Hz, 2H), 1.65 (s, 3H), 1.39 (s, 3H).

4.9 2-Fluoro-8-(2-iodo-5-methoxy-benzyl)-9-(4-methyl-pent-3-enyl)-9H-purin-6-ylamine; Rt=10.04; 1HNMR (CDCl3-d) δ 7.76 (d. J=8.6 Hz, 1H), 6.65 (d, J=2.5 Hz, 1H), 6.60 (dd, J=8.6, 2.5 Hz, 1H), 6.14 (s, 2H), 5.13 (t, J=6.9 Hz, 1H), 4.26 (s, 2H), 4.01 (t, J=7.0 Hz, 2H), 3.72 (s, 31), 2.43 (quint., J=7.0 Hz, 2H), 1.68 (s, 3H), 1.42 (s, 3H).

4.10 2-Fluoro-8-(2-iodo-5-methoxy-benzyl)-9-pent-4-ynyl-9H-purin-6-ylamine; Rt=8.75; $^1$HNMR (CDCl3-d) δ 7.77 (d, J=8.7 Hz, 1H), 6.67 (d, J=2.7 Hz, 1H), 6.62 (dd, J=8.7, 2.7 Hz, 1H), 5.99 (s, 2H), 4.32 (s, 2H), 4.16 (t, J=7.2 Hz, 2H), 3.74 (s, 3H), 2.26 (td, J=6.7, 2.6 Hz, 2H), 2.02 (t, J=2.4 Hz, 1H), 1.99 (quint., J=6.9 Hz, 2H); MP: 172-177° C.

Example 5

General Procedure for Palladium-mediated Couplings

A mixture of 9-Butyl-8-(5-iodo-2-methoxy-benzyl)-9H-purin-6-ylamine (50 mg, 0.1 mmol) and Pd(PPh$_3$)$_4$ (12 mg, 0.01 mmol) was treated under N$_2$ at r.t. with a 1M solution of the organometallic coupling partner (0.5 ml, 0.5 mmol). Reactions were performed typically in THF at r.t. for 10 min with organomagnesium compounds in THF at r.t. for 16 h with organozinc compounds, or in DMF at 80° C. for 3 h with organostannanes. After work-up, the product was purified by chromatography on preparative plates (1000 uM, SiO$_2$), eluting with CH$_2$Cl$_2$:EtOAc:hexane:MeOH:Et$_3$N 1500:750:750:50:10.

The following compounds were prepared using the corresponding commercially available organozinc compound; the skilled artisan will recognize that equivalent organnostannane, and organoboron, and organomagnesium coupling partners may be used in place of organozinc compounds. A general review of appropriate methodologies may be found in "Palladium Reagents in Organic Synthesis" Richard F. Heck, Academic Press, 1990.

5.1 9-Butyl-8-(5-ethyl-2-methoxy-benzyl)-9H-purin-6-ylamine; Rt=8.23; $^1$H NMR (CDCl3) δ 8.30 (s, 1H), 7.07 (dd, J=8.4 & 2.0 Hz, 1H), 6.91 (d, J=2.0 Hz, 1H), 6.83 (d, J=8.4 Hz, 1H), 5.65-5.55 (s, 2H), 4.23 (s, 2H), 4.04 (t, J=7.6

Hz, 2H), 3.83 (s, 3H), 2.51 (q, J=7.6 Hz, 2H) 1.65-1.55 (m, 2H), 1.30-1.25 (m, 2H), 1.41 (t, J=7.6 Hz, 3H), 0.86 (t, J=7.3 Hz, 3H).

5.2  9-Butyl-8-(5-butyl-2-methoxy-benzyl)-9H-purin-6-ylamine; Rt=9.24; $^1$H NMR (CDCl3) δ 8.33 (s, 1H), 7.05 (dd, J=8.4 & 1.9 Hz, 1H), 6.88 (d, J=1.8 Hz, 1H), 6.82 (d, J=8.3 Hz, 1H), 5.58-5.48 (s, 2H), 4.23 (s, 2H), 4.04 (t, J=7.6 Hz, 2H), 3.83 (s, 3H), 2.47 (q, J=7.6 Hz, 2H), 1.57 (quint., J=7.5 Hz, 2H), 1.48 (quint., J=7.6 Hz, 2H), 1.32-1.22 (m, 4H), 0.87 (t, J=7.3 Hz, 3H), 0.86 (t, J=7.3 Hz, 3H).

5.3  9-Butyl-8-(2-methoxy-5-vinyl-benzyl)-9H-purin-6-ylamine; Rt=7.91; $^1$H NMR (CDCl3) δ 8.31 (s, 1H), 7.31 (dd, J=8.5 & 2.3 Hz, 1H), 7.16 (d, J=2.2 Hz, 1H), 6.87 (d, J=8.5 Hz, 1H), 6.59 (dd, J=17.6 & 10.9 Hz, 1H), 5.82-5.72 (s, 2H), 5.53 (dd, J=17.6 & 0.7 Hz, 1H), 5.09 (dd, J=10.9 & 0.7 Hz, 1H), 4.22 (s, 2H), 4.06 (t, J=7.6 Hz, 2H), 3.85 (s, 3H), 1.62 (quint., J=7.7 Hz, 2H), 1.30 (sext., J=7.4 Hz, 2H), 0.87 (t, J=7.4 Hz, 3H).

Example 6

General Procedure for the Nitration of Benzene Ring and Derivatizations

A solution of purine in $H_2SO_4$ or in $H_2SO_4$:AcOH 1:4 was treated at 0° C. with 1 equiv $HNO_3$. The mixture was diluted with EtOAc, neutralized with $NaHCO_3$ and purified by chromatography on $SiO_2$ preparative plates (1000 uM) with $CH_2Cl_2$:EtOAc:hexane: MeOH:$Et_3$N 1500:750:750:50:10.

Nitro derivatives (20 mg) are reduced with 10% Pd/C (Aldrich) (20 mg) under $H_2$ atmosphere in THF at r.t. over 16 h. The resulting aniline can be further monoalkylated (Acetylchloride, $CH_2Cl_2$) or reductively alkylated (RCHO, NaBH(OAc)$_3$, 1,2-dichloroethane, r.t.).

The following compounds were prepared by this method:

6.1  8-(2,5-Dimethoxy-4-nitro-benzyl)-2-fluoro-9-pent-4-ynyl-9H-purin-6-ylamine (CF310), Rt=8.05; $^1$H NMR (CDCl3) δ 7.94 (s, 1H), 6.85 (s, 1H), 6.37-6.27 (s, 2H), 4.06 (s, 2H), 4.01 (t, J=7.3 Hz, 2H), 3.69 (s, 3H), 3.66 (s, 3H), 2.13 (td, J=7.0 & 2.6 Hz, 2H), 1.87 (t, J=2.6 Hz, 1H), 1.82 (quint., J=7.3 Hz, 2H).

6.2  9-Butyl-8-(3,5-dimethoxy-2-nitro-benzyl)-9H-purin-6-ylamine; sulfuric acid salt; Rt=7.33; $^1$H NMR (DMSO-d6) δ 8.27 (s, 1H), 8.15-7.90 (br. s, 2H), 6.78 (d, J=2.4 Hz, 1H), 6.55 (d, J=2.4 Hz, 1H), 4.32 (s, 2H), 4.12 (t, J=7.3 Hz, 2H), 3.88 (s, 3H), 3.81 (s, 3H), 1.58 (quint., J=7.5 Hz, 2H), 1.21 (sext., J=7.5 Hz, 2H), 0.84 (t, J=7.4 Hz, 3H).

6.3  8-(4-Amino-3,5-dimethoxy-benzyl)-9-butyl-9H-purin-6-ylamine; Rt=805; $^1$H NMR (CDCl3) δ 8.31 (s, 1H), 7.31 (dd, J=8.5 & 2.3 Hz, 1H), 7.16 (d, J=2.2 Hz, 1H), 6.87 (d, J=8.5 Hz, 1H), 6.59 (dd, J=17.6 & 10.9 Hz, 1H), 5.82-5.72 (s, 2H), 5.53 (dd, J=17.6 & 0.7 Hz, 1H), 5.09 (dd, J=10.9 & 0.7 Hz, 1H), 4.22 (s, 2H), 4.06 (t, J=7.6 Hz, 2H), 3.85 (s, 3H), 1.62 (quint., J=7.7 Hz, 2H), 1.30 (sext., J=7.4 Hz, 2H), 0.87 (t, J=7.4 Hz, 3H).

6.4  8-(4-Amino-2,5-dimethoxy-benzyl)-9-butyl-9H-purin-6-ylamine; Rt=6.95; 1H NMR (CDCl3) δ 8.33 (s, 1H), 6.57 (s, 1H), 6.33 (s, 1H), 6.37-6.27 (s, 2H), 4.20 (s, 2H), 4.01 (t, J=7.3 Hz, 2H), 3.74 (s, 3H), 3.68 (s, 3H), 1.59 (quint., J=7.5 Hz, 2H), 1.32 (sext., J=7.5 Hz, 2H), 0.86 (t, J=7.4 Hz, 3H).

6.5  8-(2-Amino-3,5-dimethoxy-benzyl)-9-butyl-9H-purin-6-ylamine; $^1$H NMR (CDCl3) δ 8.28 (s, 1H), 6.40 (d, J=2.5 Hz, 1H), 6.30 (d, J=2.5 Hz, 1H), 5.85-5.75 (s, 2H), 4.14 (s, 2H), 4.13 (t, J=7.6 Hz, 2H), 3.80 (s, 3H), 3.73 (s, 3H), 1.62 (quint., J=7.5 Hz, 2H), 1.48 (quint., J=7.5 Hz, 2H), 0.91 (t, J=7.4 Hz, 3H).

6.6  2-(6-Amino-9-butyl-9H-purin-8-ylmethyl)-4-methoxy-benzaldehyde-O-methyl-oxime; Rt=7.69; $^1$H NMR (CDCl3) δ 8.88 (s, 1H), 8.31 (s, 1H), 7.72 (d, J=7.9 Hz, 1H), ), 6.80 (d, J=8.0 Hz, 1H), 6.74 (s, 1H), 5.80-5.76 (s, 2H), 4.24 (s, 2H), 4.00 (t, J=7.7 Hz, 2H), 3.94 (s, 3H),3.76 (s, 3H), 1.58 (quint., J=7.7 Hz, 2H), 1.28 (sext., J=7.5 Hz, 2H), 0.86 (t, J=7.3 Hz, 3H).

Example 7

Formylation of Benzene Ring and Derivatization

A solution of 9-butyl-8-(3-methoxy-benzyl)-9H-purin-6-ylamine (100 mg, 0.32 mmol), 1,1-dichlorodimethyl ether (40 mg, 0.35 mmol) and TiCl$_4$ (133 mg, 0.70 mmol) in $CH_2Cl_2$ (10 ml) was prepared at 0° C. and stirred at r.t. overnight. Dilution with $CH_2Cl_2$, washing ($Na_2SO_4$, $NH_4Cl$), drying, and preparative thin layer chromatography gave the title aldehyde as a yellow glass (47 mg, 43%).

Standard procedures gave the corresponding alcohol ($NaBH_4$, MeOH, r.t.), tosyl hydrazone (TsNHNH$_2$, EtOH, reflux), oximes (RONH$_2$.HCl, DMF, 60° C.), amines (R$_1$R$_2$NH, NaBH(OAc)$_3$, Cl—(CH$_2$)$_2$—Cl r.t.), homoallylic alcohol (AllSiMe$_3$, TiCl$_4$), $CH_2Cl_2$, −78° C.), or alkenes.

7.1  2-(6-Amino-9-butyl-9H-purin-8-ylmethyl)-4-methoxy-benzaldehyde; Rt=6.52; $^1$HNMR (CDCl3-d) δ 10.39 (s, 1H), 8.32 (s, 1H), 7.76 (d, J=7.8 Hz, 1H), 6.87 (m, 2H), 6.22 (s, 2H), 4.28 (s, 2H), 4.03 (t, J=7.6 Hz, 2H), 3.85 (s, 3H), 1.61 (quint., J=7.3 Hz, 2H), 1.29 (sext., J=7.4 Hz, 2H), 0.86 (t, J=7.2 Hz, 3H).

Example 8

Negishi Couplings

A mixture of 3,4-dichlorobenzyl bromide (0.47 g, 1.96 mmol) and Rieke Zinc (3.0 ml, 5 g/100 ml THF, 2.35 mmol) was stirred overnight at r.t. in a flame-dried Schlenk tube and decanted to provide a 0.65M stock solution of 3,4-dichlorobenzyl zinc bromide. A solution of 8-bromo-9-butyl-9H-purin-6-ylamine (42.7 mg, 0.158 mol), Pd(dppf)Cl$_2$ (16.8 mg, 0.020 mmol), and 3,4-dichlorobenzyl zinc bromide (0.61 ml, 0.65M in THF) was stirred in a flame-dried Schlenk tube at 66° C. overnight, quenched with sat. aq. NH$_4$Cl and sat. aq. EDTA., extracted into EtOAc, dried and concentrated. Preparative TLC purification (EtOAc/CH$_2$Cl$_2$/MeOH 14:14:2) provided the title compound as a colorless oil (approx. 15 mg, 20%).

8.1  9-Butyl-8-(3,4-dichloro-benzyl)-9H-purin-6-ylamine, compound isolated as solid, Rt=7.98.

S-Linker Compounds

Example 9

9-Butyl-8-(2-iodo, 5-methoxy-phenylsulfanyl)-9H-purin-6-ylamine

Step 1: Adenine (47 g, 0.35 mole) was suspended in 200 ml of CHCl3 before adding bromine (180 ml, 3.5 mole) in one portion. The suspension was left stirring at room temperature for 72 hours in a closed system that was vented by a 20 G needle. The reaction was worked up by adding shaved ice into the suspension before slowly neutralizing with aqueous ammonia to pH 8-9, followed by precipitation of the desired product with acetic acid. The crude product was dried under reduced pressure for 2 days to give 8-Bromoadenine as a light brown powder (45 g, 60% yield). $^1$H NMR (DMSO-d$_6$) δ 8.12 (s, 1H), 7.22 (s, 2H). Rf(75% EtOAc/Hex)=0.4.

Step 2: 8-Bromopurine (2.2 g, 10 mmole) was dissolved in 50 ml of DMF before adding 1-bromo-butane (2.2 ml, 20 mmol) and cesium carbonate (6.7 g, 20 mmol) into the solution. The reaction mixture was left stirring at room temperature for 16 hours before quenching with water and extracting with EtOAc. The organic layer was washed with water and dried with MgSO$_4$ before removing solvent under reduced pressure. A white powder (0.9 g, 33%) of 8-Bromo-9-butyl-9H-purin-6-ylamine was isolated using silica gel column chromatography (50% EtOAc/Hexanes). $^1$H NMR (CDCl$_3$) δ 8.32, (s, 1H), 5.81 (s, 2H), 4.20 (t, 2H), 1.82 (m, 2H), 1.40 (m, 2H), 0.96 (t, 3H). Rf (75% EtOAc/Hex)=0.6.

Step 3: To a mixture of sodium hydride (96 mg, 4 mmol) in DMF (4 ml) was added 3-methoxy-benzenethiol (1.12 g, 8 mmol). After 30 min, a solution of 8-bromo-9-butyl-9H-purin-6-ylamine (0.54 g, 2 mmol) in DMF (6 ml) was added and stirred for 12 h at 70° C. The reaction mixture was quenched by addition of MeOH (4 ml), diluted with EtOAc (400 ml), washed with Na$_2$CO$_3$ (3×100 ml), brine (3×100 ml), dried (Na$_2$SO$_4$), evaporated, purified with flash chromatography (CH$_2$Cl$_2$:MeOH=100:5) to give the title sulfide as a colorless powder (0.59 g, 89%).

HPLC method used for these compounds: Agilent Zorbax 300 SB C18, 4.6×150 mm, 5 µm; Column Temperature: Ambient; Flow Rate: 1.0 ml/min, Gradient: 5% acetonitrile (0.05% TFA) in water (0.1% TFA) to 100% acetonitrile (0.05% TFA) in 15 minutes, hold at 100% for 2 minutes).

The following compounds were prepared using the corresponding thiol in place of the 3-methoxybenzene thiol used in step 3:

9.1 3-(6-Amino-9-butyl-9H-purin-8-ylsulfanyl)-phenol; Rt=6.75 min $^1$HNMR (DMSO-d6): δ 9.69 (s, 1H), 8.17 (s, 1H), 7.45 (s, 2H), 7.17 (t, J=7.9 Hz, 1H), 6.76 (d, J=7.4 Hz, 1H), 6.68 (d, J=8.2 Hz, 1H), 6.62 (s, 1), 4.11 (t, J=7.0 Hz, 2H), 1.57 (quint., J=7.3 Hz, 2H), 1.19 (sext., J=6.8 Hz, 2H), 0.81 (t, J=7.4 Hz, 3H).

9.2 9-Butyl-8-(3-methoxy-phenylsulfanyl)-9H-purin-6-ylamine; Rt=8.6 min; $^1$H NMR (DMSO-d6) δ 0.80 (t, J=7.4 Hz, 3H, CH$_3$), 1.20 (m, 2H, CH$_2$), 1.61 (m, m, 2H, CH$_2$), 3.60 (s, 3H, OCH$_3$), 3.76 (s, 3H, OCH$_3$), 4.13 (t, J=7.4 Hz, 2H, CH$_2$), 6.46 (s, 1H, Ar—H), 6.85 (d, J=8.9 Hz, 1H, Ar—H), 7.02 (d, J=8.9 Hz, 1H, Ar—H), 7.41 (bs, 2H, NH$_2$), 8.15 (s, 1H, purine-H).

9.3 9-Butyl-8-(2,5-dimethoxy-phenylsulfanyl)-9H-purin-6-ylamine); Rt=7.62 min; $^1$HNMR (CDCl$_3$-d): δ 8.30 (s, 1H), 7.18 (t, J=8.2 Hz, 1H), 6.90 (m, 2H), 6.77 (m, 3H), 4.17 (t, J=7.6 Hz, 2H), 3.70 (s, 3H), 1.67 (quint., J=7.5 Hz, 2H), 1.28 (sext., J=7.5 Hz, 2H), 0.86 (t, J=7.4 Hz, 3H).

Step 4: To a solution of 9-butyl-8-(3-methoxy-phenylsulfanyl)-9H-purin-6-ylamine (0.26 g, 0.73 mmol) in AcOH (4 ml) was added NIS (0.53 g, 2.19 mmol) in portions. The mixture was stirred for 24 h at r.t. The reaction mixture was diluted with EtOAc (200 ml), and carefully neutralized with a solution of K$_2$CO$_3$ (2×50 ml), them washed with Na$_2$S$_2$O$_3$ (3×50 ml), brine (3×50 ml), dried (Na$_2$SO$_4$), evaporated, purified by preparative TLC chromatography (CH$_2$Cl$_2$:MeOH=100:5) to give the 2-iodo isomer (60 mg), and the 4-iodo isomer (65 mg).

9.4 9-Butyl-8-(2-iodo-5-methoxy-phenylsuffanyl)-9H-purin-6-ylamine; Rt=8.45 min; $^1$HNMR (CDCl$_3$-d): δ 8.38 (s, 1H), 7.73 (d, J=8.7 Hz, 1H), 6.71 (d, J=2.7 Hz, 1H), 6.58 (dd, J=8.1, 1.8 Hz, 1H), 5.91 (s, 2H), 4.22 (t, J=7.4 Hz, 2H), 3.68 (s, 3H), 1.75 (quint., J=7.7 Hz, 2H), 1.34 (sext., J=7.5 Hz, 2H), 0.93 (t, J=7.4 Hz, 3H).

9.5 9-Butyl-8-(4-iodo-3-methoxy-phenylsulfanyl)-9H-purin-6-ylamine; Rt=8.63 min; $^1$HNMR (CDCl$_3$-d): δ 8.38 (s, 1H), 7.72 (d, J=8.1 Hz, 1H), 6.92 (d, J=1.8 Hz, 1H), 6.58 (dd, J=8.1, 1.8 Hz, 1H), 5.82 (s, 2H), 4.22 (t, J=7.4 Hz, 2H), 3.85 (s, 3H), 1.75 (quint., J=7.7 Hz, 2H), 1.37 (sext., J=7.5 Hz, 2H), 0.93 (t, J=7.4 Hz, 3H).

For compounds in which the N9 substituent (Y) is sensitive to halogenation conditions, these may be prepared using iodide already present in the benzenethiol moiety:

To a suspension of sodium hydride (96 mg, 4 mmol) in DMF (3 ml) was added 2-iodo-5-methoxy-benzenethiol (1.06 g, 4 mmol; J Org. Chem, 2001, 66(13), 4525-4542). After 30 min, a solution of 8-bromo-9-(4-methyl-pent-3-enyl)-9H-purin-6-ylamine (296 mg, 1 mmol) in DMF (3 ml) was added, and the mixture was stirred for 12 h at 70° C. The reaction was quenched by addition of MeOH (2 ml), diluted with EtOAc (200 ml), washed with Na$_2$CO$_3$ (3×50 ml), brine (3×50 ml), dried (Na$_2$SO$_4$), evaporated, and purified by flash chromatography (CH$_2$Cl$_2$: MeOH=100:5) to give 8-(2-Iodo-5-methoxy-phenylsulfanyl)-9-(4-methyl-pent-3-enyl)-9H-purin-6-ylamine as a colorless powder (280 mg, 58%).

The following compounds were prepared by this method using, respectively, the electrophiles 1-bromo-4-methyl-pent-3-ene and 1-chloro-pent-4-yn:

9.6 8-(2-Iodo-5-methoxy-phenylsulfanyl)-9-(4-methyl-pent-3-enyl)-9H-purin-6-ylamine; Rt=9.14 min; $^1$HNMR (CDCl$_3$-d): δ 8.39 (s, 1H), 7.72 (d, J=8.7 Hz, 1H), 6.72 (d, J=2.7 Hz, 1H), 6.58 (dd, J=8.7, 2.7 Hz, 1H), 5.81 (s, 2H), 5.15 (t, J=7.3 Hz, 1H), 4.25 (t, J=7.4 Hz, 2H), 3.69 (s, 3H), 2.50 (quint., J=7.3 Hz, 2H), 1.66 (s, 3H), 1.44 (s, 3H); MP: 167-167.5° C.

9.7 8-(2-Iodo-5-methoxy-phenylsulfanyl)-9-pent-4-ynyl-9H-purin-6-ylamine; Rt=7.93 min; $^1$HNMR (CDCl$_3$-d): δ 8.38 (s, 1H), 7.75 (d, J=8.7 Hz, 1H), 6.74 (d, J=2.7 Hz, 1H), 6.60 (dd, J=8.7, 2.7 Hz, 1H), 5.72 (s, 2H), 4.32 (t, J=7.3 Hz, 2H), 3.70 (s, 3H), 2.28 (td, J=6.8, 2.6 Hz, 2H), 2.06 (quint., J=7.3 Hz, 2H), 2.00 (t, J=2.4 Hz, 1H); MP: 168-169° C.

The following compounds were prepared using the corresponding thiol in place of the 3-methoxybenzene thiol and base t-BuOK in place of NaH used in step 3:

9.8 8-(Benzothiazole-2-ylsulfanyl)-9-butyl-9H-purin-6-ylamine; Rt=6.53 min; $^1$H NMR (CDCl$_3$) 8.41 (s, 1H), 7.94 (d, 1H), 7.74 (d, 1H), 7.47 (t, 1H), 7.38 (t, 1H), 6.01 (s, 2H), 4.32 (t, 2H), 1.79 (m, 2H), 1.35 (m, 2H), 0.89 (t, 3H).

9.9 9-Butyl-8-(5-chloro-benzothiazole-2-ylsulfanyl)-9H-purin-6-ylamine; Mass (M+1)=391.8 et (M+3)=393.8; $^1$H NMR (CDCl$_3$) 8.43 (s, 1H), 7.92 (s, 1H), 7.65 (d, 1H), 7.35 (d, 1H), 6.01 (s, 2H), 4.32 (t, 2H), 1.79 (m, 2H), 1.35 (m, 2H), 0.89 (t, 3H).

9.10 9-Butyl-8-(5-methoxy-benzothiazole-2-ylsulfanyl)-9H-purin-6-ylamine; $^1$H NMR (CDCl$_3$) 8.42 (s, 1H), 7.60 (d, 1H), 7.43 (s, 1H), 7.02 (d, 1H), 5.82 (s, 2H), 4.33 (t, 2H), 3.99 (s, 3H), 1.80 (m, 2H), 1.35 (m, 2H), 0.89 (t, 3H).

9.11 9-Butyl-8-(2,5-dichloro-phenylsulfanyl)-9H-purin-6-ylamine; $^1$H NMR (CDCl$_3$) 8.37 (s, 1H), 7.35 (d, 1H), 7.20 (dd, 1H), 7.14 (d, 1H), 5.72 (s, 2H), 4.24 (t, 2H), 1.79 (m, 2H), 1.35 (m, 2H), 0.89 (t, 3H).

9.12 9 Butyl-8-(2,4,5-trichloro-phenylylsulfanyl)-9H-purin-6-ylamine; Rt=7.8 min; $^1$H NMR (CDCl$_3$) 8.37 (s, 1H), 7.62 (s, 1H), 7.35 (s, 1H), 5.98 (s, 2H), 4.27 (t, 2H), 1.80 (m, 2H), 1.36 (m, 2H), 0.92 (t, 3H).

Example 10

8-(2,5-dimethoxy-phenylsulfanyl)-2-fluoro-9(4-methyl-pent-3-enyl)-9H-purin-6-ylamine and 8-(2,5-dimethoxy-phenylsulfanyl)-2-amino-9(4-methyl-pent-3-enyl)-9H-purin-6-ylamine were prepared from 2,6-diaminopurine by procedures analogous to the one described above in Example 9. The final conversion of amino to fluoro was done by method similar to that reported in Example 2, step 4.

10.1 8-(2,5-dimethoxy-phenylsulfanyl)-2-amino-9(4-methyl-pent-3-enyl)-9H-purin-6-ylamine; $^1$H NMR (DMSO-d6) δ 1.28 (s, 3H, CH$_3$), 1.58 (s, 3H, CH$_3$), 2.35 (m, 2H, CH$_2$), 3.60 (s, 3H, OCH$_3$), 3.76 (s, 3H, OCH$_3$), 4.12 (t, J=7.0 Hz, 2H, CH$_2$), 5.05 (t, J=7 Hz, 1H, CH=), 6.50 (s, 1H, Ar—H), 6.91 (d, J=8.9 Hz, 1H, Ar—H), 7.05 (d, J=8.9 Hz, 1H, Ar—H).

10.2 8-(2,5-dimethoxy-phenylsulfanyl)-2-fluoro-9(4-methyl-pent-3-enyl)-9H-purin-6-ylamine; $^1$H NMR (DMSO-d6) δ 1.30 (s, 3H, CH$_3$), 1.55 (s, 3H, CH$_3$), 2.35 (m, 2H, CH$_2$), 3.60 (s, 3H, OCH$_3$), 3.76 (s, 3H, OCH$_3$), 4.10 (t, J=7.0 Hz, 2H, CH$_2$), 5.05 (t, J=7 Hz, 1H, CH=), 6.47 (s, 1H, Ar—H), 6.86 (d, J=8.9 Hz, 1H, Ar—H), 7.02 (d, J=8.9 Hz, 1H, Ar—H); MS (m/z) 426 (M+Na).

Example 11

The compounds in this example were prepared analogously to the method described above in Example 9 using various electrophiles to generate a library of N9 substituted compounds. N9 alkylation was done as a final step after the bromine displacement of 8-bromopurine with 2,5-dimethoxy thiophenol.

11.1 8-(2,5-dimethoxy-phenylsulfanyl)-9H-purin-6-ylamine; $^1$H NMR (DMSO-d$_6$) δ 3.62 (s, 3H, OCH$_3$), 3.76 (s, 3H, OCH$_3$), 6.61 (s, 1H, Ar—H), 6.85 (d, J=8.9 Hz, 1H, Ar—H), 7.02 (d, J=8.9 Hz, 1H, Ar—H), 7.24 (bs, 2H, NH$_2$), 8.13 (s, 1H, purine-H) 13.33 (s, 1H, purine-NH); electrophile: No substitution on N9.

11.2 8-(2,5-dimethoxy-phenylsulfanyl)-9-pentyl-9H-purin-6-ylamine; $^1$H NMR (DMSO-d$_6$) δ 0.80 (t, J=7.4 Hz, 3H, CH$_3$), 1.20 (m, 4H; 2CH$_2$,) 1.61 (m, 2H, CH$_2$), 3.60 (s, 3H, OCH$_3$), 3.76 (s, 3H, OCH$_3$), 4.13 (t, J=7.4 Hz, 2H, CH$_2$), 6.46(s, 1H, Ar—H), 6.85 (d, J=8.9 Hz, 1H, Ar—H), 7.02 (d, J=8.9 Hz, 1H, Ar—H), 7.41 (bs, 2H, NH$_2$), 8.15 (s, 1H, purine-H); electrophile: 1-bromopentyl.

11.3 8-(2,5-dimethoxy-phenylsulfanyl)-9-pent-4-ynyl-9H-purin-6-ylamine; $^1$H NMR (DMSO-d$_6$) δ 1.89 (m, 2H, CH$_2$), 2.20 (t, J=8.0 Hz, 2H, CH$_2$), 2.78 (s, 1H, CH≡), 3.62 (s, 3H, OCH$_3$), 3.76 (s, 3H, OCH$_3$), 4.23 (t, J=7.4 Hz, 2H, CH$_2$), 6.46 (s, 1H, Ar—H), 6.85 (d, J=8.9 Hz, 1H, Ar—H), 7.02 (d, J=8.9 Hz, 1H, Ar—H), 7.41 (bs, 2H, NH$_2$), 8.15 (s, 1H, purine-H); electrophile: 1-chloro-pent-4-yne.

11.4 4-[6-Amino-8(2,5-dimethoxysulfanyl)-purin-9-yl]-butyronitrile; $^1$H NMR (DMSO-d$_6$) δ 1.89 (m, 2H, CH$_2$), 2.20 (t, J=8.0 Hz, 2H, CH$_2$), 3.62 (s, 3H, OCH$_3$), 3.76 (s, 3H, OCH$_3$), 4.23 (t, J=7.4 Hz, 2H, CH$_2$), 6.46 (s, 1H, Ar—H), 6.85 (d, J=8.9 Hz, 1H, Ar—H), 7.02 (d, J=8.9 Hz, 1H, Ar—H), 7.41 (bs, 2H, NH$_2$), 8.15 (s, 1H, purine-H); electrophile: 1-bromobutyronitrile.

11.5 8-(2,5-dimethoxy-phenylsulfanyl)-9(3,3,3-trifluoromethylpropyl)-9H-purin-6-ylamine; $^1$H NMR (DMSO-d$_6$) δ2.54 (t, J=8.0 Hz, 2H, CH$_2$), 3.62 (s, 3H, OCH$_3$), 3.74 (s, 3H, OCH$_3$), 4.46 (t, J=8.0 Hz, 2H, CH$_2$), 6.46 (s, 1H, Ar—H), 6.85 (d, J=8.9 Hz, 1H, Ar—H), 7.02 (d, J=8.9 Hz, 1H, Ar—H), 7.41 (bs, 2H, NH$_2$), 8.30 (s, 1H, purine-H); electrophile: 1-bromo-3,3,3-trifluoro-propane.

11.6 8-(2,5-dimethoxy-phenylsulfanyl)-9(4-chlorobutyl)-9H-purin-6-ylamine; $^1$H NMR (DMSO-d$_6$) δ 1.82 (m, 2H, CH$_2$), 1.98 (m, 2H, CH$_2$), 3.56 (t, J=6.4 Hz, 2H, CH$_2$), 3.75 (s, 3H, OCH$_3$), 3.78 (s, 3H, OCH$_3$), 4.23 (t, J=7.4 Hz, 2H, CH$_2$), 6.46 (s, 1H, Ar—H), 6.85 (d, J=8.9 Hz, 1H, Ar—H), 7.02 (d, J=8.9 Hz, 1H, Ar—H), 7.41 (bs, 2H, NH$_2$), 8.15 (s, 1H, purine-H); electrophile: 1-bromo-4-chlorobutane.

11.7 8-(2,5-dimethoxy-phenylsulfanyl)-9(4-acetyloxybutyl)-9H-purin-6-ylamine; $^1$H NMR (DMSO-d$_6$) δ1.70 (m, 2H, CH$_2$), 1.90 (m, 2H, CH$_2$), 2.02 (s, 3H, CH$_3$), 3.75 (s, 3H, OCH$_3$), 3.78 (s, 3H, OCH$_3$), 4.10 (t, J=6.4 Hz, 2H, CH$_2$), 4.30 (t, J=7.4 Hz, 2H, CH$_2$), 6.46 (s, 1H, Ar—H), 6.85 (d, J=8.9 Hz, 1H, Ar—H), 7.02 (d, J=8.9 Hz, 1H, Ar—H), 7.41 (bs, 2H, NH$_2$), 8.15 (s, 1H, purine-H); electrophile: 1-bromo-4-acetyloxybutane.

11.8 8-(2,5-dimethoxy-phenylsulfanyl)-9(5-bromophentyl)-9H-purin-6-ylamine; $^1$H NMR (DMSO-d$_6$) δ1.46 (m, 2H, CH$_2$), 1.85 (m, 4H, 2CH$_2$), 3.36 (t, J=6.7 Hz, 2H, CH$_2$), 3.72 (s, 3H, OCH$_3$), 3.80 (s, 3H, OCH$_3$), 4.30 (t, J=7.4 Hz, 2H, CH$_2$), 6.46 (s, 1H, Ar—H), 6.85 (d, J=8.9 Hz, 1H, Ar—H), 7.02 (d, J=8.9 Hz, 1H, Ar—H), 7.41 (bs, 2H, NH$_2$), 8.15 (s, 1H, purine-H); electrophile: 1,5-dibromopentane.

11.9 8-(2,5-dimethoxy-phenylsulfanyl)-9(2-[1,3]dioxolan-2-yl-ethyl)-9H-purin-6-ylamine; $^1$H NMR (DMSO-d$_6$) δ 2.26 (m, 2H, CH$_2$), 3.75 (s, 3H, OCH$_3$), 3.77 (s, 3H, OCH$_3$), 3.85 (t, J=7.0 Hz, 2H, CH$_2$), 3.98 (t, J=7.0 Hz, 2H, CH$_2$), 4.46 (t, J=7.4 Hz, 2H, CH$_2$), 4.96 (t, J=4.1 Hz, 1H, CH), 6.46 (s, 1H, Ar—H), 6.85 (d, J=8.9 Hz, 1H, Ar—H), 7.02 (d, J=8.9 Hz, 1H, Ar—H), 7.41 (bs, 2H, NH$_2$), 8.15 (s, 1H, purine-H); electrophile: 2-(2-Chloro-ethyl)-[1,3]dioxolane.

11.10 8-(2,5-dimethoxy-phenylsulfanyl)-9-(4-methyl-pent-3-enyl)-9H-purin-6-ylamine; $^1$H NMR (DMSO-d$_6$) δ 1.28 (s, 3H, CH$_3$), 1.54 (s, 3H, CH$_3$), 2.35 (m, 2H, CH$_2$), 3.60 (s, 3H, OCH$_3$), 3.76 (s, 3H, OCH$_3$), 4.15 (t, J=7.0 Hz, 2H, CH$_2$), 5.05 (t, J=7 Hz, 1H, CH=), 6.46 (s, 1H, Ar—H), 6.86 (d, J=8.9 Hz, 1H, Ar—H), 7.02 (d, J=8.9 Hz, 1H, Ar—H), 7.42 (bs, 2H, NH$_2$), 8.17 (s, 1 H, purine-H); electrophile: 1-bromo-4-methyl-pent-3-ene; MP: 148-150° C.

11.11 8-(2,5-dimethoxy-phenylsulfanyl)-9-(pent-4-enyl)-9H-purin-6-ylamine; $^1$H NMR (DMSO-d$_6$) δ 1.89 (m, 2H, CH$_2$), 2.19 (t, J=8.0 Hz, 2H, CH$_2$), 3.62 (s, 3H, OCH$_3$), 3.76 (s, 3H, OCH$_3$), 4.23 (t, J=7.4 Hz, 2H, CH$_2$), 5.05 (m, 2H, CH$_2$=), 5.82 (m, 1H, CH=), 6.46 (s, 1H, Ar—H), 6.85 (d, J=8.9 Hz, 1H, Ar—H), 7.02 (d, J=8.9 Hz, 1H, Ar—H), 7.41 (bs, 2H, NH$_2$), 8.15 (s, 1H, purine-H); electrophile: 1-chloro-pent-4-yne.

11.12 8-(2,5-dimethoxy-phenylsulfanyl)-9-(3-hydroxypropyl)-9H-purin-6-ylamine; $^1$H NMR (DMSO-d$_6$) δ 1.82 (m, 2H, CH$_2$), 3.60 (s, 3H, OCH$_3$), 3.76 (s, 3H, OCH$_3$), 4.12 (m, 2H, CH$_2$), 4.21 (t, J=7.0 Hz, 2H, CH$_2$), 6.47 (s, 1H, Ar—H), 6.86 (d, J=8.9 Hz, 1H, Ar—H), 7.02 (d, J=8.9 Hz, 1H, Ar—H); 8.15 (s, 1H, purine-H); electrophile: 1-bromo-3-hydroxypropane.

Example 12

The compounds in this example were prepared using diazonium salts and thiols as coupling partners.

12.1 9-Butyl-8-(2-iodo-5-methoxy-phenylsulfanyl)-9H-purin-6-ylamine

Step 1: A suspension of 8-bromo-9-butyl-9H-purin-6-ylamine (0.50 g, 1.85 mmol) and thiourea (1.49 g, 19.6 mmol) in n-butanol (10 ml) was heated to reflux for 14 h. Dilution with CH$_2$Cl$_2$ (70 ml), washing with water and concentration afforded 6-amino-9-butyl-7,9-dihydro-purine-8-thione as a white powder (0.42 g, 1.87 mmol, 100%). $^1$H NMR (DMSO-d$_6$) δ 12.35-12.25 (br. s, 1H), 8.13 (s, 1H), 6.92-6.72 (br. s., 2H), 4.09 (t, J=7.6 Hz, 2H), 1.71 (quint., J=7.5 Hz, 2H), 1.29 (sext., J=7.5 Hz, 2H), 0.87 (t, J=7.4 Hz, 3H).

Step 2: A solution of the above thione (30.8 mg, 0.138 mmol) and t-BuOK (15.5 mg, 0.138 mmol) in MeOH (0.55 ml) was treated portion-wise with crude 2-iodo-5-methoxybenzenediazonium tetrafluoroborate (48 mg, 0.138 mmol). The vigorous N$_2$ evolution ceased after 2 min. Work-up and preparative TLC (MeOH:CH$_2$Cl$_2$ 5:95) yielded the title sulfide.

9-Butyl-8-(2-iodo-5-methoxy-benzyl)-9H-purin-6-ylamine; Rt=8.45 min; $^1$HNMR (CDCl$_3$-d): δ 8.38 (s, 1H), 7.73 (d, J=8.7 Hz, 1H), 6.71 (d, J=2.7 Hz, 1H), 6.58 (dd, J=8.7, 2.7 Hz, 1H), 5.91 (s, 2H), 4.22 (t, J=7.4 Hz, 2H), 3.68 (s, 3H), 1.75 (quint., J=7.7 Hz, 2H), 1.34 (sext., J=7.5 Hz, 2H), 0.93 (t, J=7.4 Hz, 3H).

Example 13

Fluorescence-Based Competitive Binding Assay for Biotinylated-Geldanamycin to Purified Hsp90

This assay directly measures the binding of biotinylated-geldanamycin (biotin-GM) to purified Hsp90 and thus tests the ability of compounds to compete for binding to Hsp90.

Purified native Hsp90 protein (mixture of alpha and beta) from HeLa cells (Stressgen Biotechnologies Corp., San Diego, Calif., USA) was coated onto 96-well plates by incubating for 1 hr at 37° C. Uncoated Hsp90 was removed and the wells washed twice in 1×PBS (phosphate-buffered saline) buffer. Biotin-GM was then added to the wells, and the reaction was further incubated for 1 hr 37° C. The wells were washed twice with 1×PBS, before the addition of 20 ug/ml streptavidin-phycoerythrin, and incubated for 1 hr at 37° C. The wells were again washed twice with 1×PBS. The fluorescence was then measured in a Gemini spectrofluorometer (Molecular Devices) using an excitation of 485 nm and emission of 580 nm.

The compounds in Table 4 were synthesized and evaluated for HSP90 binding ability based on the above assay:

TABLE 4

| Example # | IC50 μM | Example # | IC50 μM |
|---|---|---|---|
| 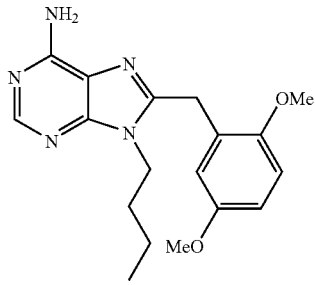 1.1 | 10 | 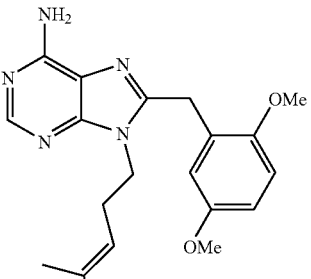 3.4 | 2.8 |
| 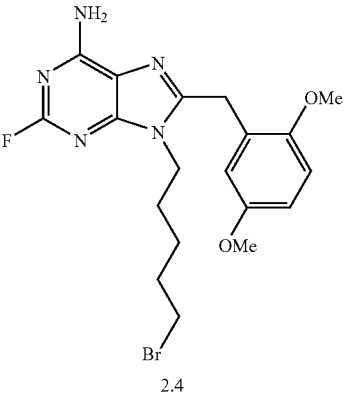 2.4 | 2.0 | 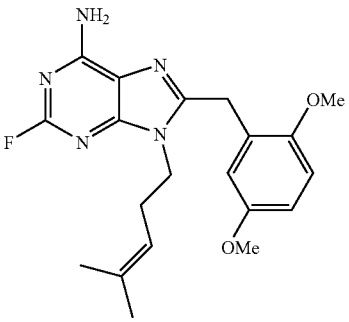 2.2 | 1.1 |
| 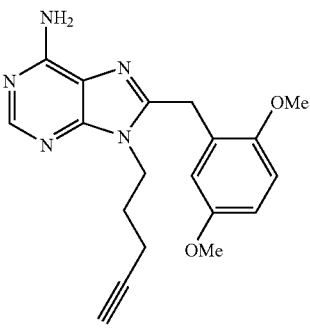 3.2 | 6 | 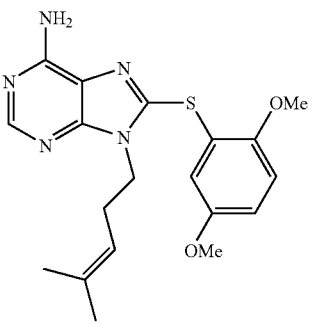 11.10 | 1.3 |

TABLE 4-continued

| Example # | IC50 μM | Example # | IC50 μM |
|---|---|---|---|
| 2.1 | 2 | 4.7 | 1.1 |
| 4.8 | 0.9 | 4.9 | 2.3 |
| 9.4 | 1.5 | 4.10 | 0.9 |
| 9.5 | 1.8 | 9.6 | 0.9 |

TABLE 4-continued

| Example # | IC50 μM | Example # | IC50 μM |
|---|---|---|---|
| 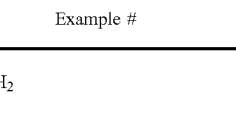<br>11.3 | 4.0 | 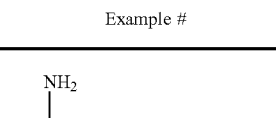<br>9.7 | 0.8 |

Example 14

HER₂ Inhibition Assay

MCF-7 cells are seeded in 24 well plates at a density of approximately 30,000 cells/well and allowed to grow for 16 hours in DMEM supplemented with 10% FBS. Drug is then added at a concentration range of 100 uM to 0.01 uM. Cells are incubated for an additional 24. Drug treated cells and untreated control cells are trypsinized, and incubated at room temperature for 15 minutes with anti Her-2 neu Ab conjugated with phycoerythrin (Becton Dickinson, San Jose Calif.; Cat no. 340552) at a concentration of 0.25 ug/ml, or non-specific control IgG1 conjugated with phycoerythrin (Becton Dickinson, San Jose Calif.; Cat no. 340761). Samples were analyzed using a FACS Calibur flow cytometer (Becton Dickinson) equipped with Argon-ion laser that which emits 15 mW of 488 nm light for excitation of the phycoerythrin fluorochrome. 10,000 events were collected per sample. A fluorescence histogram was generated and the mean fluorescence intensity (mfi) of each sample was determined using Cellquest software. The background was defined as the mfi generated from cells incubated with control IgG, and was subtracted from each sample stained with the HER-2/neu Ab. Percent degradation of Her-2 was calculated as follows:

% Her-2 degradation=($mfi$ HER-2 sample)/($mfi$ HER-2 untreated cells)×100

Table 5 summarizes the Her-2 degradation ability of various compounds of the invention:

TABLE 5

| Example # | IC50 μM | Example # | IC50 μM |
|---|---|---|---|
| 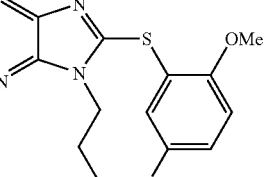<br>1.1 | 6.0 | 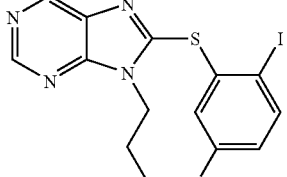<br>3.4 | 1.5 |

TABLE 5-continued
| Example # | IC50 μM | Example # | IC50 μM |
|---|---|---|---|
| 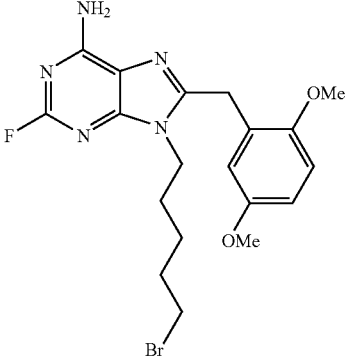 2.4 | 1.0 | 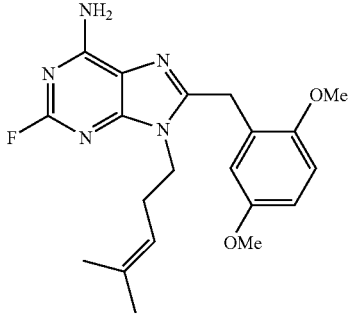 2.2 | 0.5 |
| 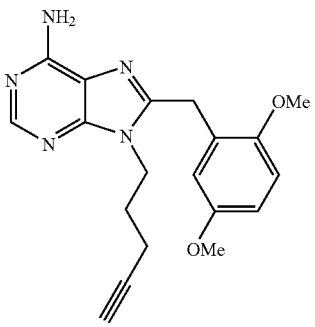 3.2 | 1.5 | 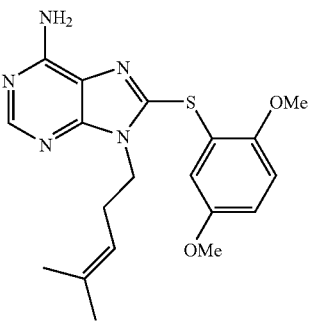 11.10 | 0.7 |
| 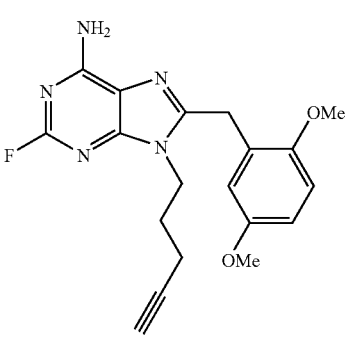 2.1 | 0.6 | 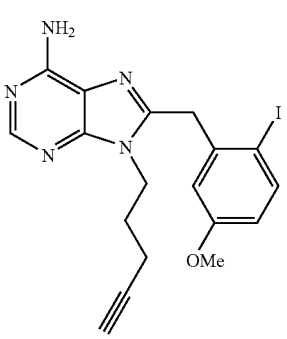 4.7 | 1.5 |
| 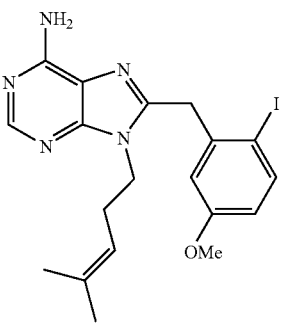 4.8 | 0.8 | 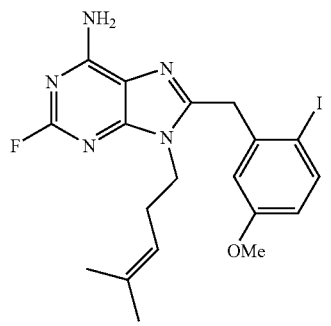 4.9 | 1.0 |

TABLE 5-continued

| Example # | IC50 μM | Example # | IC50 μM |
|---|---|---|---|
| 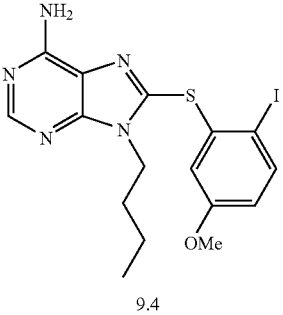 9.4 | 1.5 | 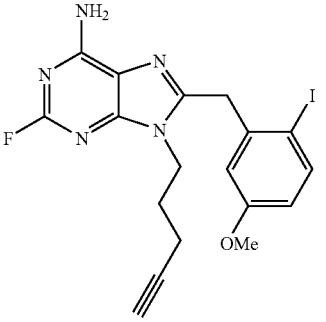 4.10 | 0.8 |
| 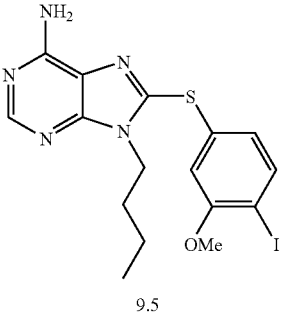 9.5 | 2.0 | 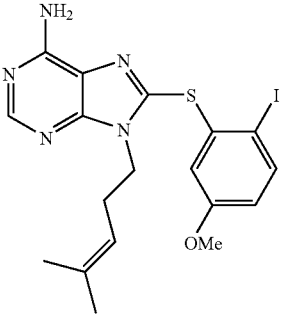 9.6 | 0.3 |
| 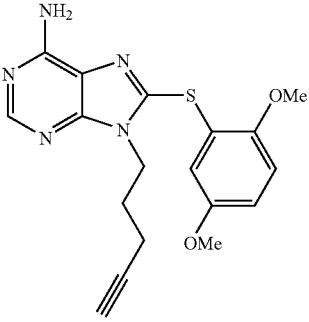 11.3 | 1.4 | 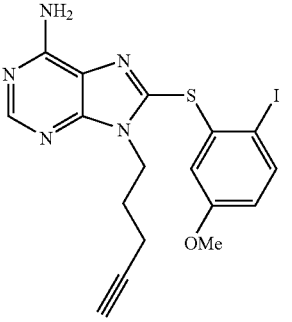 9.7 | 0.3 |

Inhibitory Concentration 50 (IC$_{50}$) for this assay is the concentration necessary to degrade 50% of Her 2 expression (protein).

The foregoing examples are not limiting and merely illustrative of various aspects and embodiments of the present invention. All documents cited herein are indicative of the levels of skill in the art to which the invention pertains and are incorporated by reference herein in their entireties. None, however, is admitted to be prior art.

One skilled in the art will readily appreciate that the present invention is well adapted to carry out the objects and obtain the ends and advantages mentioned, as well as those inherent therein. The methods and compositions described illustrate preferred embodiments, are exemplary, and are not intended as limitations on the scope of the invention. Certain modifications and other uses will occur to those skilled in the art, and are encompassed within the spirit of the invention, as defined by the scope of the claims.

The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described, or portions thereof. It is recognized that various modifications are possible within the scope of the invention claimed. Thus, it should be understood that although the present invention has been specifically disclosed by preferred embodiments, optional features, modifications and variations of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group, and exclusions of individual members as appropriate, or by proviso.

Other embodiments are within the following claims.

We claim:

1. A compound of formula:

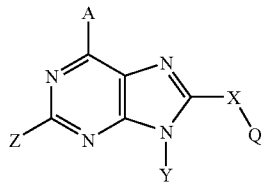

wherein,
X is S;
A is NH$_2$ or CH$_3$;
Z is selected from the group of F, Cl, Br and CF$_3$;
Y is selected from the group of optionally substituted C$_2$-C$_8$ alkyl, optionally substituted C$_3$-C$_8$ alkenyl, optionally substituted C$_3$-C$_8$ alkynyl, optionally substituted C$_6$-C$_{10}$ aryl, and optionally substituted C$_3$-C$_{10}$ alicyclic;
Q is a member selected from the group of:

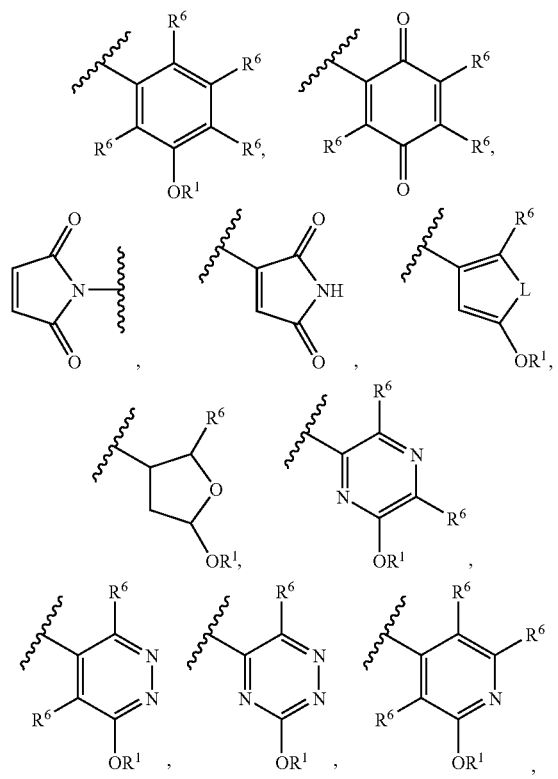

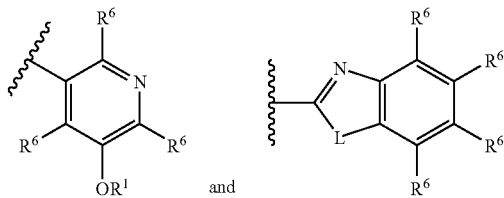

L is O, S or NR$^1$;
R$^1$ is independently selected from the group of H, optionally substituted C$_1$-C$_6$ alkyl, optionally substituted C$_3$-C$_{10}$ cycloalkyl, optionally substituted aryl, optionally substituted heterocyclic, C(O)R$^2$, C(O)OR$^2$, C(O)NR$^4$$_2$, C(S)OR$^2$, C(S)NR$^4$$_2$, and S(O)$_2$R$^2$;
R$^2$ is independently selected from the group of C$_1$-C$_6$ alkyl, C$_3$-C$_{10}$ cycloalkyl, heterocyclic, heteroaryl, and aryl, all optionally substituted;
R$^3$ is independently selected from the group of H, optionally substituted C$_1$-C$_6$ alkyl, optionally substituted C$_3$-C$_{10}$ cycloalkyl, optionally substituted aryl, optionally substituted heterocyclic and C(O)NR$^4$$_2$;
R$^4$ is independently selected from the group of H, optionally substituted C$_1$-C$_6$ alkyl, optionally substituted C$_3$-C$_{10}$ cycloalkyl, optionally substituted aryl, and optionally substituted heterocyclic; and
each R$^6$ is independently selected from the group of H, optionally substituted C$_1$-C$_6$ alkyl, lower cycloalkyl, OR$^3$, SR$^3$, NHR$^3$, C(O)N(R$^4$)$_2$, NO$_2$, CN, halogen, and S(O)$_2$R$^2$;
or a tautomer or a pharmaceutically acceptable salt or prodrug thereof.

2. A compound of formula:

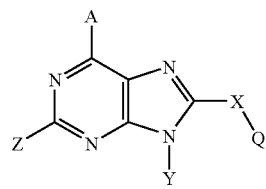

wherein,
X is S;
A is NH$_2$ or CH$_3$;
Z is selected from the group of H, F, Cl, Br and CF$_3$;
Y is selected from the group of optionally substituted C$_2$-C$_8$ alkyl, optionally substituted C$_3$-C$_8$ alkenyl, optionally substituted C$_3$-C$_8$ alkynyl, optionally substituted C$_6$-C$_{10}$ aryl, and optionally substituted C$_3$-C$_{10}$ alicyclic;
Q is a member selected from the group of:

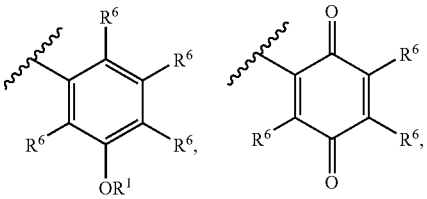

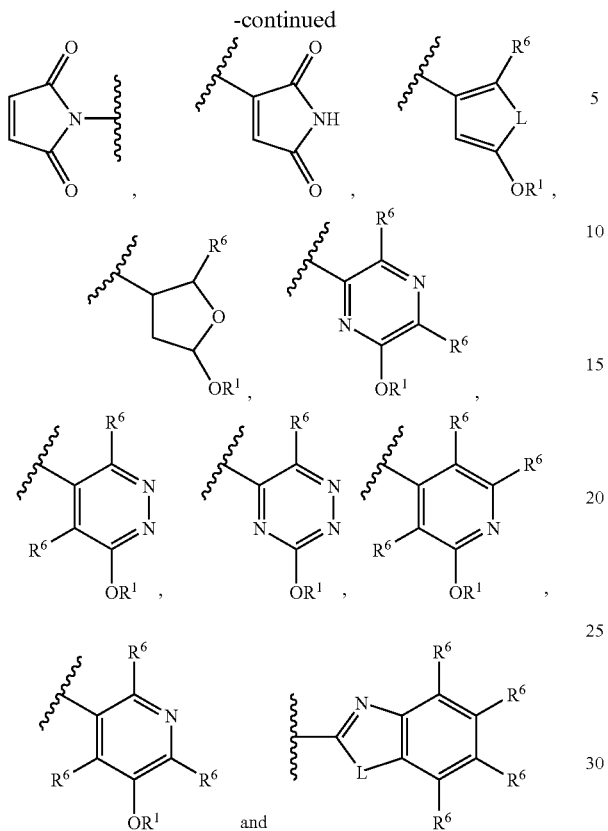

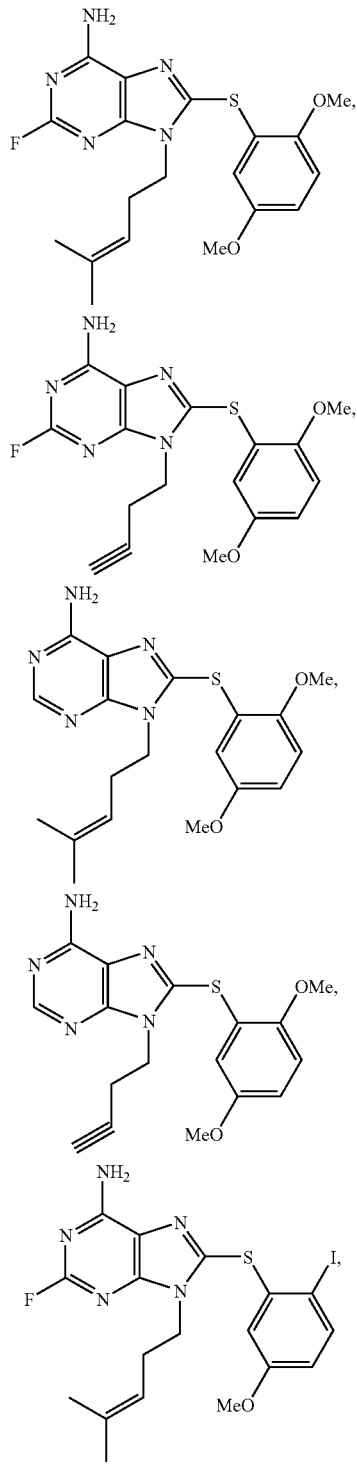

Q is selected from the group of 2,5-dimethoxyphenyl, 2-iodo-5-methoxyphenyl, 4-iodo-5-methoxyphenyl, 2-iodo-4-fluoro-5-methoxyphenyl, 2-bromo-5-methoxyphenyl, 2-chloro-5-methoxyphenyl, 2,4-diiodo-5-methoxyphenyl, 2-iodo-4-bromo-5-methoxyphenyl, 2-iodo-4-chloro-5-methoxyphenyl, and 2-chloro-3,4,5-trimethoxyphenyl.

4. A compound selected from the group of:

L is O, S or $NR^1$;

$R^1$ is independently selected from the group of H, optionally substituted $C_1$-$C_6$ alkyl, optionally substituted $C_3$-$C_{10}$ cycloalkyl, optionally substituted aryl, optionally substituted heterocyclic, $C(O)R^2$, $C(O)OR^2$, $C(O)NR^4{}_2$, $C(S)OR^2$, $C(S)NR^4{}_2$, and $S(O)_2R^2$;

$R^2$ is independently selected from the group of $C_1$-$C_6$ alkyl, $C_3$-$C_{10}$ cycloalkyl, heterocyclic, heteroaryl, and aryl, all opiionally substituted;

$R^3$ is independently selected from the group of H, optionally substituted $C_1$-$C_6$ alkyl, optionally substituted $C_3$-$C_{10}$ cycloalkyl, optionally substituted aryl, optionally substituted heterocyclic and $C(O)NR^4{}_2$;

$R^4$ is independently selected from the group of H, optionally substituted $C_1$-$C_6$ alkyl, optionally substituted $C_3$-$C_{10}$ cycloalkyl, optionally substituted aryl, and optionally substituted heterocyclic; and each $R^6$ is independently selected from the group of H, optionally substituted $C_1$-$C_6$ alkyl, lower cycloalkyl, $OR^3$, $SR^3$, $NHR^3$, $C(O)N(R^4)_2$, $NO_2$, CN, halogen, and $S(O)_2R^2$, provided that at least one $R^6$ is OMe or halogen;

or a tautomer or a pharmaceutically acceptable salt or prodrug thereof.

3. A compound according to claim 2, wherein

A is $NH_2$;

Z is selected from the group of H, Cl and F;

Y is selected from the group of —$(CH_2)_2CH$=$C(CH_3)_2$, —$(CH_2)_3CCH$; —$(CH_2)_4Br$, —$(CH_2)_4Cl$, —$(CH_2)_4OAc$, —$(CH_2)_4NHEt$, —$(CH_2)_4OH$, —$(CH_2)_5Br$, —$(CH_2)_5Cl$, —$(CH_2)_5OAc$, —$(CH_2)_2$—$O(CH)(CH_3)_2$, and —$(CH_2)_5OH$; and -continued

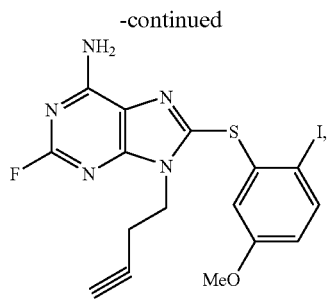

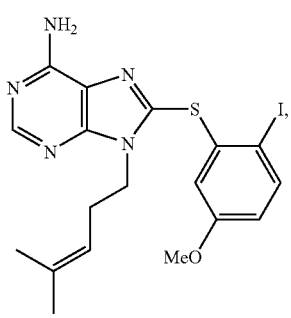

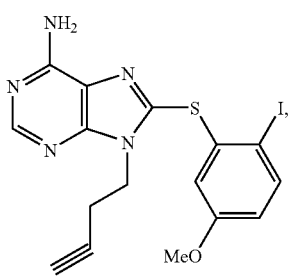

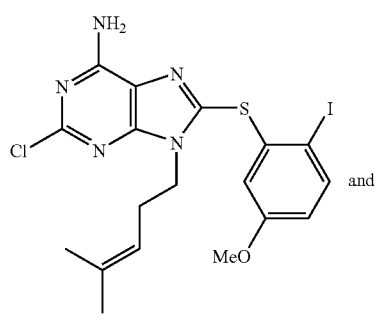 and

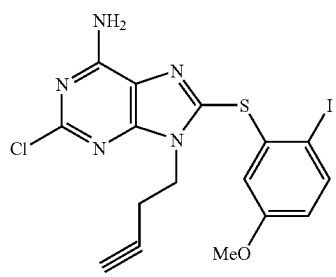

wherein Me is a methyl group.

5. A compound of formula:

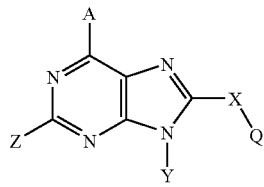

wherein,

X is S;

A is NH$_2$ or CH$_3$;

Z is selected from the group of H, F, Cl, Br and CF$_3$;

Y is selected from the group of optionally substituted C$_2$-C$_8$ alkyl, optionally substituted C$_3$-C$_8$ alkenyl, optionally substituted C$_3$-C$_8$ alkynyl, optionally substituted C$_6$-C$_{10}$ aryl, and optionally substituted C$_3$-C$_{10}$ alicyclic; wherein the optional substituent of Y is selected from alkyl, alkenyl, alkynyl, haloalkyl, haloalkenyl, haloalkynyl, cycloalkyl, alkoxy, haloalkoxy, amino, alkylamino, dialkylamino, alkylthio, oxo, carboxyester, carboxamido, acyloxy, halogen, CN, NO$_2$, NH$_2$, N$_3$, NHCH$_3$, N(CH$_3$)$_2$, SH, SCH$_3$, OH, OCH$_3$, OCF$_3$, CH$_3$, $CF_3$, C(O)CH$_3$, CO$_2$CH$_3$, CO$_2$H, C(O)NH$_2$;

Q is a member selected from the group of:

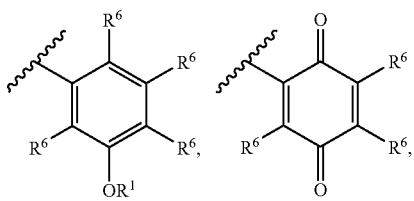

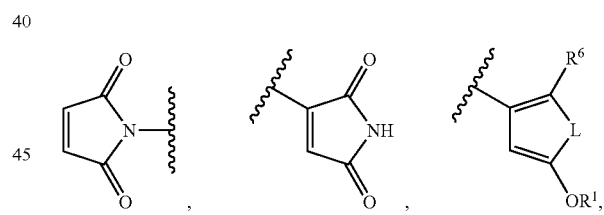

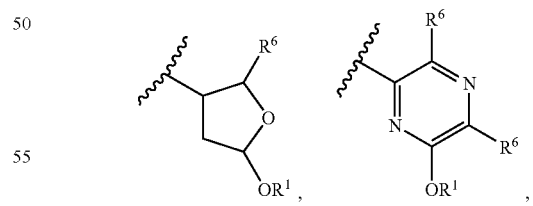

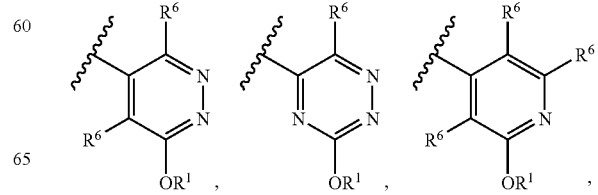

-continued

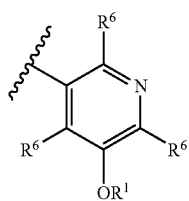 and 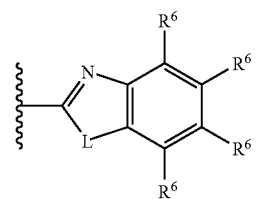

L is O, S or NR$^1$;

R$^1$ is independently selected from the group of H, optionally substituted C$_1$-C$_6$ alkyl, optionally substituted C$_3$-C$_{10}$ cycloalkyl, optionally substituted aryl, optionally substituted heterocyclic, C(O)R$^2$, C(O)OR$^2$, C(O)NR$^4_2$, C(S)OR$^2$, C(S)NR$^4_2$, and S(O)$_2$R$^2$;

R$^2$ is independently selected from the group of C$_1$-C$_6$ alkyl, C$_3$-C$_{10}$ cycloalkyl, heterocyclic, heteroaryl, and aryl, all optionally substituted;

R$^3$ is independently selected from the group of H, optionally substituted C$_1$-C$_6$ alkyl, optionally substituted C$_3$-C$_{10}$ cycloalkyl, optionally substituted aryl, optionally substituted heterocyclic and C(O)NR$^4_2$;

R$^4$ is independently selected from the group of H, optionally substituted C$_1$-C$_6$ alkyl, optionally substituted C$_3$-C$_{10}$ cycloalkyl, optionally substituted aryl, and optionally substituted heterocyclic; and each R$^6$ is independently selected from the group of H, optionally substituted C$_1$-C$_6$ alkyl, lower cycloalkyl, OR$^3$, SR$^3$. NHR$^3$, C(O)N(R$^4$)$_2$, NO$_2$, CN, halogen, and S(O)$_2$R$^2$;

or a tautomer or a pharmaceutically acceptable salt or prodrug thereof.

\* \* \* \* \*